US009320473B2

(12) United States Patent
Shuler

(10) Patent No.: US 9,320,473 B2
(45) Date of Patent: *Apr. 26, 2016

(54) METHOD AND SYSTEM FOR MONITORING OXYGENATION LEVELS OF A COMPARTMENT FOR DETECTING CONDITIONS OF A COMPARTMENT SYNDROME

(71) Applicant: J&M SHULER INC., Athens, GA (US)

(72) Inventor: Michael Simms Shuler, Athens, GA (US)

(73) Assignee: J&M SHULER, INC., Athens, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,739

(22) Filed: Dec. 14, 2013

(65) Prior Publication Data

US 2014/0309501 A1    Oct. 16, 2014

Related U.S. Application Data

(63) Continuation of application No. 13/279,298, filed on Oct. 23, 2011, now Pat. No. 8,694,068, and a continuation of application No. 11/831,954, filed on Jul. 31, 2007, now Pat. No. 8,100,834.

(60) Provisional application No. 60/903,632, filed on Feb. 27, 2007.

(51) Int. Cl.
*A61B 5/0205* (2006.01)
*A61B 5/00* (2006.01)
(Continued)

(52) U.S. Cl.
CPC ............... *A61B 5/7282* (2013.01); *A61B 5/021* (2013.01); *A61B 5/022* (2013.01); *A61B 5/0205* (2013.01);
(Continued)

(58) Field of Classification Search
CPC ..... A61B 5/02; A61B 5/02028; A61B 5/0205; A61B 5/021; A61B 5/1455
See application file for complete search history.

(56) References Cited

U.S. PATENT DOCUMENTS

| 4,380,240 A | 4/1983 | Jobsis et al. |
| 4,423,736 A | 1/1984 | DeWitt et al. |

(Continued)

FOREIGN PATENT DOCUMENTS

| WO | WO94/27493 | 12/1994 |
| WO | 9620638 A1 | 7/1996 |

(Continued)

OTHER PUBLICATIONS

Tsien, Christine. "Reducing False Alarms in the Intensive Care Unit: A Systematic Comparison of Four Algorithms." Proceedings of the AMIA Annual Fall Symposium (1997). vol. 4, Issue: Suppl., Publisher: American Medical Informatics Association, p. 894.*

(Continued)

*Primary Examiner* — Jacqueline Cheng
*Assistant Examiner* — Meredith Weare
(74) *Attorney, Agent, or Firm* — Smith Tempel; Steven P. Wigmore

(57) ABSTRACT

A method and system for continually monitoring oxygenation levels in real-time in compartments of an animal limb, such as in a human leg or a human thigh or a forearm, can be used to assist in the diagnosis of a compartment syndrome. The method and system can include one or more near infrared compartment sensors in which each sensor can be provided with a compartment alignment mechanism and a central scan depth marker so that each sensor may be precisely positioned over a compartment of a living organism. The method and system can include a device for displaying oxygenation levels corresponding to respective compartment sensors that are measuring oxygenation levels of a compartment of interest. The method and system can also monitor the relationship between blood pressure and oxygenation levels and activate alarms based on predetermined conditions relating to the oxygenation levels or blood pressure or both.

19 Claims, 23 Drawing Sheets

(51) Int. Cl.
  *A61B 5/0215*  (2006.01)
  *A61B 5/022*   (2006.01)
  *A61B 5/1455*  (2006.01)
  *A61B 5/021*   (2006.01)
  *A61B 5/145*   (2006.01)

(52) U.S. Cl.
  CPC .......... *A61B 5/0215* (2013.01); *A61B 5/1455* (2013.01); *A61B 5/14507* (2013.01); *A61B 5/14542* (2013.01); *A61B 5/14557* (2013.01); *A61B 5/4519* (2013.01); *A61B 5/6824* (2013.01); *A61B 5/6828* (2013.01); *A61B 5/7246* (2013.01); *A61B 5/742* (2013.01); *A61B 5/7405* (2013.01); *A61B 5/746* (2013.01)

(56) References Cited

U.S. PATENT DOCUMENTS

| | | | |
|---|---|---|---|
| 5,139,025 A | 8/1992 | Lewis et al. | |
| 5,217,013 A | 6/1993 | Lewis et al. | |
| 5,465,714 A | 11/1995 | Scheuing | |
| 5,482,034 A | 1/1996 | Lewis et al. | |
| 5,485,848 A | 1/1996 | Jackson et al. | 600/485 |
| 5,492,118 A | 2/1996 | Gratton et al. | |
| 5,584,296 A | 12/1996 | Cui et al. | |
| 5,680,857 A | 10/1997 | Pelikan et al. | 600/323 |
| 5,766,127 A | 6/1998 | Pologe et al. | |
| 5,782,757 A | 7/1998 | Diab et al. | |
| 5,853,370 A | 12/1998 | Chance et al. | |
| 6,050,951 A | 4/2000 | Friedman et al. | 600/485 |
| 6,070,092 A | 5/2000 | Kazama et al. | |
| 6,192,261 B1 | 2/2001 | Gratton et al. | |
| 6,308,088 B1 | 10/2001 | MacFarlane et al. | |
| 6,458,109 B1 | 10/2002 | Henley et al. | |
| 6,498,942 B1 | 12/2002 | Esenaliev et al. | |
| 6,549,795 B1 | 4/2003 | Chance | |
| 6,615,065 B1 | 9/2003 | Barrett et al. | |
| 6,801,799 B2 | 10/2004 | Mendelson | 600/330 |
| 6,819,950 B2 | 11/2004 | Mills | |
| 6,948,942 B1 | 9/2005 | Chih | |
| 7,030,749 B2 | 4/2006 | Al-Ali | 340/511 |
| 7,047,054 B2 | 5/2006 | Benni | |
| 7,097,625 B2 | 8/2006 | Steinberg | |
| 7,184,809 B1 | 2/2007 | Sterling et al. | |
| 7,221,970 B2 | 5/2007 | Parker | |
| 7,236,813 B2 | 6/2007 | Parker | |
| 7,491,169 B2 | 2/2009 | Yost et al. | |
| 7,596,397 B2* | 9/2009 | Ortner et al. | 600/344 |
| 8,100,834 B2* | 1/2012 | Shuler | 600/483 |
| 8,116,852 B2 | 2/2012 | Baker et al. | 600/476 |
| 8,639,309 B2* | 1/2014 | Shuler | 600/324 |
| 8,694,068 B2* | 4/2014 | Shuler | 600/324 |
| 2001/0003793 A1 | 6/2001 | Steuer et al. | |
| 2002/0058865 A1 | 5/2002 | Cheng et al. | 600/323 |
| 2003/0060808 A1 | 3/2003 | Wilk | |
| 2004/0024297 A1 | 2/2004 | Chen et al. | |
| 2004/0054290 A1 | 3/2004 | Chance | 600/473 |
| 2004/0109163 A1 | 6/2004 | Bambot et al. | |
| 2005/0033127 A1 | 2/2005 | Ciurczak et al. | |
| 2005/0177046 A1 | 8/2005 | Mills | 600/481 |
| 2005/0215898 A1 | 9/2005 | Yost et al. | 600/438 |
| 2005/0250998 A1 | 11/2005 | Huiku | 600/331 |
| 2005/0283092 A1 | 12/2005 | Gedebou | |
| 2006/0015025 A1 | 1/2006 | Johnstone | |
| 2007/0012931 A1 | 1/2007 | Lee et al. | |
| 2007/0100218 A1 | 5/2007 | Sweitzer et al. | |
| 2007/0167926 A1 | 7/2007 | Blott et al. | |
| 2008/0015421 A1 | 1/2008 | Penner | |
| 2008/0146906 A1 | 6/2008 | Baker et al. | 600/407 |
| 2008/0208011 A1 | 8/2008 | Shuler | |
| 2009/0177051 A1 | 7/2009 | Arons et al. | |
| 2009/0237647 A1 | 9/2009 | Azimi et al. | |
| 2010/0145169 A1 | 6/2010 | Li et al. | 600/323 |
| 2013/0006121 A1 | 1/2013 | Myers | 600/479 |
| 2014/0316215 A1* | 10/2014 | Shuler | 600/301 |

FOREIGN PATENT DOCUMENTS

| | | | |
|---|---|---|---|
| WO | 0000080 A1 | 1/2000 | |
| WO | 2003034899 A1 | 5/2003 | |
| WO | 03087767 A2 | 10/2003 | |
| WO | WO2008/064482 | 6/2008 | |
| WO | WO 2008064482 A1 | 6/2008 | .............. A61B 5/00 |

OTHER PUBLICATIONS

Gentilello et al. "Near-infrared spectroscopy versus compartment pressure for the diagnosis of lower extremity compartmental syndrome using electromyography-determined measurements of neuromuscular function." J Trauma. Jul 2001;51(1):1-8, discussion 8-9.*

Bariteau JT et al., The use of near-infrared spectrometry for the diagnosis of lower-extremity compartment syndrome. Orthopedics. Mar. 11, 2011;34(3):178. doi: 10.3928/01477447-20110124-12, nine pages (pdf version).

Mohler LR et al, "Intramuscular deoxygenation during exercise in patients who have chronic anterior compartment syndrome of the leg," Journal of Bone and Joint Surgery Am. Jun. 1997; 79(6):844-9, eight pages (pdf version).

Arbabi, Saman et al., Near-Infrared Spectrocopy: A Potential Method for Continuous, Transcutaneous Monitoring for Compartment Syndrome in Critically Injured Patients; the Journal of Trauma: Injury, Infection, and Critical Care; vol. 47, No. 5, Nov. 1999, pp. 829-833.

Mohler, L. Randall, M.D. et al., Intramuscular Deoxygenation during Exercise in Patients Who Have Chronic Anterior Compartment Syndrome of the Leg; J Bone Joint Surg [Am], Jun. 1997; vol. 79-A; pp. 844-849.

Garr, Jeff L. et al., Monitoring for Compartmental Syndrome Using Near-Infrared Spectroscopy: A Noninvasive, Continuous, Transcutaneous Monitoring Technique; The Journal of Trauma: Injury, infection, and Critical Care; vol. 46, No. 4, Apr. 1999, pp. 613-618.

Gentilello, Larry M. et al., Near-Infrared Spectroscopy versus Compartment Pressure for the Diagnosis of Lower Extremity Compartmental Syndrome Using Electromyography-Determined Measurements of Neuromuscular Function; The Journal of Trauma: Injury, Infection, and Critical Care; vol. 51, No. 1, Jul. 2001, pp. 1-9.

Giannotti, Giovanni et al., Utility of Near-Infrared Spectroscopy in the Diagnosis of Lower Extremity Compartment Syndrome; The Journal of Trauma: Injury, Infection, and Critical Care; vol. 48, No. 3, Mar. 2000, pp. 396-401.

International Search Report for PCT Application Serial No. PCT/US08/54871 mailed Jun. 20, 2008 1-pg.

Holland, Greg, ViOptix ODISsey Tissue Oximeter, Regulatory Specialists, Inc., 8-pgs, Premarket Notification, Jan. 2005.

InSpectra™ Tissue Spectrometer, 2003 Hutchinson Technology Inc. 1 pg.

Somanetics®, An opportunity to impact outcomes nobody likes to talk about, INVOS® System, 2005, (12 pgs.)

Somanetics®, An opportunity to impact outcomes nobody likes to talk about, INVOS®. Cerebral Oximeter, Reflecting the Color of Life™, Dec. 2005 (8-pgs.)

INVOS®, System Specifications, INVOS® 5100C Cerebral/Somatic Oximeter System, Jun. 2006, 2-pgs.

Greensmith, M.D.,PHD., J. Eric, Hyperbaric Oxygen Therapy in Extremity Trauma, Journal of the American Academy of Orthopaedic Surgeons, pp. 376-384, Copyright 2004.

Cascio, M.D., Brett M. et al., Documentation of Acute Compartment Syndrome at an Academic Health-Care Center, The Journal of Bone and Joint Surgery, Feb. 2005, vol. 87-A, No. 2, pp. 346-350.

Oxiplets™ Near Infrared, Non-Invasive, Tissue Spectrometer, A non-invasive, real-time monitor of precise tissue oxygenation and hemoglobin concentration, Jul. 11, 2007. http://www.isss.com/products/oxiplex/about.html., 8 pgs.

OXIPLEXTS™ Near Infrared, Non-Invasive, Tissue Spectrometer, OxiplexTS Version 2, Jul. 11, 2007. http://www.isss.somanetics.com/invos principles.htm., 5 pgs.

InSpectra™ SI0$_2$ Tissue Oxygenation Monitor, http://www.htibiomeasurement.com/index.asp. 2007. 10-pgs.

(56) References Cited

OTHER PUBLICATIONS

INVOS® Clinical Center, http://www.somanetics.com/clinical_invos_center.htm. Jul. 11, 2007. 5 pgs.
Optical Diffusion Imaging Spectroscopy (ODIS), http://www.vioptix.com/docs/technology/howitworks.asp., Jul. 11, 2007, 4 pgs.
Thomas Moore, MD, et al., Correlation between Near Infrared Spectrometry and Cuff Pressures in the Leg: A Model for Acute Compartment Syndrome Monitoring, Emory University IRB. Aug. 2006, p. 1-13, Atlanta, GA.
Mark Hamerberg, MD, et al., Correlation Between Muscle Oxygenation and Compartment Pressure in Acute Compartment Syndrome of the Leg: A New Screening Technique, Emory Universlt, School of Medicine, Consent to be a Research Subject, May 2806, pp. 1-15, Atlanta, GA.
Abouezzi, Ziad, MD, et al., A Critical Reappraisal of Indications for Fasciotomy After Extremity Vascular Trauma, Department of Surgery, Mental Health Center, Jul. 29, 2006. Reappraisal of Indications New York Medical College and Lincoln Medical and Mental Health Center, Jul. 29, 2006, pp. 547-551. vol. 133, Bronx, NY.
Arbabi, Saman, MD, et al., Near-Infrared Spectroscopy: A Potential Method for Continuous, Transcutaneous Monitoring for Compartmental Syndrome in Critically Injured Patients, The Journal of Trauma. Injury, Infection, and Critical Care, Nov. 1999, pp. 1-9, vol. 47(5).
Bermudez, Kenneth MD, et al., Fasciotomy, Chronic Venous Insufficiency, and the Calf Muscle Pump, Department of Surgery. University of California, San Francisco General Hospital, Dec. 1998, pp. 1356-1361. vol. 133.
Bhattacharyya, Timothy MD, et al., The Medical-Legal Aspects of Compartment Syndrome, The Journal of Bone and Joint Surgery, Incorporated. Apr. 2004, pp. 664-863, vol. 86-A, No. 4.
Birtles, Deirdre B., et al., Venous Obstruction in Healthy Limbs. A Model for Chronic Compartment Syndrome?, Medicine & Science in Sports & Exercise, 2003, pp. 1638-1644.
Bochmann, Rolf P. et al , External Compression Increases forearm perfusion. Journal of Applied Physiology, Aug. 4, 2005, pp. 2337-2344, vol. 99.
Boody, Anthony R., et al., Accuracy in the Measurement of Compartment Pressures. A Comparison of Three Commonly Used Devices. The Journal of Bone and Joint Surgery, Inc. Nov. 2005. pp. 2415-2422, vol. 87-A. No. 11.
Breit, Gregory A. PHD, et al., Near-Infrared Spectroscopy for Monitoring of Tissue Oxygenation of Exerusing Skeletal Muscle in a Chronic Compartment Syndrome Model, The Journal of Bone & Joint Surgery, Jun. 1997, pp. 833-843, vol. 79-A(6).
Clayton, James M., et al. Tissue Pressure and Perfusion in the Compartment Syndrome, Journal of Surgical Research, Apr. 1977, pp. 333-339, vol. 22, No. 4.
Comerota, Anthony J. MD, et al., Tissue (muscle) oxygen saturation ($StO_2$): A new measure of symptomatic lower-extremity arterial disease, Journal of Vascular Surgery, pp. 724-729, vol. 35, No. 4.
Costes, F., et al.. Age-Associated Alteration of Muscle Oxygenation Measured by Near Infrared Spectroscopy During Exercise, Archives of Physiology and Biochemistry, 1999. pp. 159-157, vol. 107, No. 2.
Davis, Scott L , et al., Skin Blood Flow Influences Near-Infrared Spectroscopy-Derived Measurements of Tissue Oxygenation During Heat Stress, Journal of Applied Physiology, Jan. 2006, pp. 221-224, vol. 100.
Fadel, Paul J., et al., Augmented Sympathetic Vasoconstriction in Exercising Forearms of Postmenopausal Women is Reversed by Oestrogen Therapy, The Physiological Society, 2004. pp. 893-901.
Ferrari, Marco, et al., Light Source-Detector Spacing of Near-Infrared-Based Tissue Oximeters and the Influence of Skin Blood Flow, Journal of Applied Physiology, 2006, pp. 1426-1427, vol. 100.
Ferrari, Marco, et al., Light Source-Detector Spacing of Near-Infrared-Based Tissue Oximeters and the Influence of Skin Blood Flow, Journal of Applied Physiology, 2005, pp. 1426-1427, vol. 100.
Fitzgerald, A.M., et al., Long-Term Sequelae of Fasciotomy Wounds, British Journal of Plastic Surgery, 2000, pp. 690-693, vol. 53.

Garr, Jeff L. MD, et al., Monitoring for Compartmental Syndrome Using Near-Infrared Spectroscopy: A Noninvasive, Continuous, Transcutaneous Monitoring Technique, The Journal of Trauma: Injury, Infection, and Critical Care, Apr. 1999, pp. 613-618. vol. 46(4).
Giovanni Giannotti, MD, et al., Utility of Near-Infrared Spectroscopy in the Diagnosis of Lower Extremity Compartment Syndrome, The Journal of Trauma: Injury, Infection, and Critical Care, pp. 396-401, vol. 48, No. 3.
J. Eric Greensmith, MD, PhD, Hyperbaric Oxygen Therapy in Extremity Trauma, Journal of the American Academy of Orthopaedic Surgeons, Nov./Dec. 2004, pp. 376-384, vol. 12, No. 6.
Heckman, Michael M., et al., Compartment Pressure in Association with Closed Tibial Fractures. The Relationship between Tissue Pressure, Compartment, and the Distance from the Site of the Fracture, Sep. 1994, pp. 1285-1292, vol. 76-A(9).
J. A. Kaye and H. Jick, Epidemiology of lower limb franctures in general practice in the United Kingdom, pp. 368-374, Injury Prevention 2004.
C.M.G. Keyzer-Dekker, MD, et al., Can transcutaneous oxygen tension measurement determine re-amputation levels?, pp. 27-30m Journal of Wound Care, Jan. 2006, vol. 15, No. 1.
Michael B. Kim, MS, et al., Estimation of Jugular Venous $O_2$ Saturation from Cerebral Oximetry or Arterial $O_2$ Saturation During Isocapnic Hypoxia, Journal of Clinial Monitoring and Computing 16, 2000, pp. 191-199.
Kartic G. Krishnan, et al., The role of near-infrared angiography in the assessment of post-operative venous congestion in random pattern, pedicted island and free flaps, British Journal of Plastic Surgery (2005 58, pp. 330-338.
L. Antsberg, et al., Laser Doppler Flowmetry, Transcutaneous Oxyten Tension Measurements and Doppler Pressure Compared in Patients Undergoing Amputationa, European Journal of Vascular Surgery, Apr. 1991;5(2), pp. 195-197.
Olof Lundin, MD. et al., Intramuscular Pressure in the Leg and Thigh Related of Tensile Strap Force During Knee Brace Wear, An Experimental Study in Man, The American Journal of Sports Medicine, pp. 567-570, vol. 26, No. 4.
M. Mars, et. al, A Comparison of Laser Doppler Fluxmetry and Transcutaneous Oxygen Pressure Measurement in th eDysvascular Patient Requirring Amputation, European Journal of Vascular Surgery. 1996, pp. 53-58.
Moed, Berton R., A Comparison of the Slit Catheter, Side-Ported Needle. and Simple Needle. [Measurement of Intracompartmental Pressure]. The Journal of Bone and Joint Surgery. Incorporated, Feb. 1993, pp. 231-235, vol. 75-A(2).
Mohler, L. Randall MD, et al. Intramuscular Deoxygenation during Exercise in Patients Who Have Chronic Anterior Compartment Syndrome of the Leg, The Journal of Bone and Joint Surgery, Incorporated, Jun. 1997, pp. 844-849. vol. 79-A.
Shoko Nioka, et al., A novel method to measure regional muscle blood flw continuously using NIRS kinetics information, Dynamic Medicine 2006, 5:5, May 16, 2006.
Shoko Nioka, et al., A novel method to measure muscle biood flw continuously using NIRS kinetics information. Dynamic Medicine 2006, 5:5, May 16, 2006.
Nadir Ozkayin, et al., Absolute compartment pressure versus differential pressure for the diagnosis of compartment syndrome in tibial fractures, International Orthopaedics (SICOT) (2005) 29, pp. 396-401.
Michael J. Prayson, MD, et al., Baseline Compartment Pressure Measurements in Isolated Lower Extremity Fractures without Clinical Compartment Syndrome, The Journal of TRAUMA® Injury, Infection, and Critical Care. pp. 1037-1040, vol. 80, No. 5.
Puyana, Juan Carlos MD, et al., Continuous Measurement of Gut pH with Near-Infrared Spectroscopy Hemorrhagic Shock, Jan. 1999, pp. 9-15, vol. 46(1).
Rhee, Peter MD, et al.. Near-infrared spectroscopy: Continuous measurement of cytochrome during hemorrhagic shock, Critical Care Medicine, Jan. 1997, pp. 166-170.
Oliver Scheufler, M.D., et al., Tissue Oxygenation and Perfusion in Inferior Pedicle Reduction Mammaplasty by Near-Infrared Reflection Spectroscopy and Color-Coded Duplex Sonography, From the

(56) References Cited

OTHER PUBLICATIONS

Department of Plastic, Reconstructive and Hand Surgery, Markus Hospital, Academic Teaching Hospital of the Johann Wolfgang Goethe University and the Department of Radiology. Güstrow Municipal Hospital, Academic Teaching Hospital of the University of Rostock, Recieved for publication Feb. 4, 2002, revised May 17, 2002, pp. 1131-1146.
Styf, Jorma MD, PhD and Wiger< Per MD, Abnormally Increased Intramuscular Pressure in Human Legs: Comparison of Two Experimental Models, The Journal of Trauma: Injury, Infection, and Critical Care, Jul. 1998, pp. 133-139, vol. 45(1).
Vollmar, Brigette M.D., et al., Microvascular Response to Compartment Syndrome-Like External Pressure Elevation: An In Vivo Fluorescence Microscopic Study in the hamster Striated Muscle, The Journal of Trauma: Injury, Infection, and Critical Care, Jan. 1999, pp. 91-96, vol. 46(1).
Annemarie Uliasz, et al., Comparing the Methods of Measuring Compartment Pressures in Acute Compartment Syndrome, American Journal of Emergency Medicine, pp. 143-145, vol. 21, No. 2.
E.B. Wassenaar, MD , et al.. Reliability of Near-infrared Spectroscopy in People with Dark Skin Pigmentation, Journal of Clinical Monitoring and Computing (2005) 19, pp. 195-199.
Weiner, Gary, et aL, Effect of Ankle: Pcsition and a Plaster Cast on intramuscular Pressure in the Human Log, The Journal of Bone and Joint Surgery (American Volume), Oct. 1994, pp. 1476-1481. vol. 76-A(10).
Michael S. Weingarten, JD, et al., Measurement of optical properties to quantify healing of chronic diabetic wounds. Wound Repair and Regeneration: Official Publication of the Wound Healing Society [and] the Europea, May-Jun. 2006; 14(3), pp. 364-370.
Per Wiger, et al., The effects of limb elevation and increased intramuscular pressure on nerve and muscle function in the human leg, Eur J Appl Physiol (2000) 83: pp. 84-88.
I.M. Williams, et al., Recent Developments in Cerebral Monitoring Near-infrared Light Spectroscopy, An Overview,, European Journal of Vascular Surgery 12, pp. 263-271 (1996).
Mark Hammerberg. MD, et al., Correlation between Infrared Spectrometry and Supplemental Oxygen Administration, Emory University IRB, Apr. 24, 2006,, Atlanta, GA.
Michael. S. Shuler, MD, Near infrared Compartment Syndrome (NICS) Monitor, Disclosure Documentation Program, Feb. 2, 2007.
Holden, C.E.A., MS, FRCS, Compartmental Syndromes Following Trauma, Clinical Orthapaedcs and Related Research, No. 113, Nov.-Dec. 1975. pp. 95-102.
Holden, C.E.A., MS, FRCS, The Role of Blood Supply to Soft Tissue in the Healing of Diaphyseal Fractures: An Experimental Study, The Journal of Bone & Joint Surgery, vol. 54-A, No. 5, Jul. 1972, pp. 992-1000.
Hupel, Thomas M., Md, et al., Muscle Peffusion after Intramedullary Nailing of the Canine Tibia, The Journal of Trauma, vol. 45(2), Aug. 1998, pp. 256-262.
Imms, F.J., et al., Blood flow through the calf during recovery from fractures of the lower limb, Clinical Science and Molecular Medicine, vol. 51(3), Sep. 1976, pp. 297-302.
Kakar, Sanjeev, et al,, Diastolic Blood Pressure in Patients With Tibia Fractures Under Anaesthesia: Implications for the Diagnosis of Compartment Syndrome, Journal of Orthop Trauma, vol. 21, No. 2, Feb. 2, 2007, pp. 99-103.
Kellerova, Eva, et al., Changes in the Muscle and Skin Blood Flow Following Lower Leg Fracture in Man, Acta Orthop. Scandinav., vol. 41, 1970, pp. 249-260.
Keyzer-Oekker, C.M.G., et al., Can transcutaneous oxygen tension measurement determine re-amputation levels? Journal of Wound Care, vol. 15, No. 1, Jan. 2006, pp. 27-30.
Korthals, Jan K., at al., Nerve and Muscle Vulnerability to Ischemia, Journal of the Neurological Sciences, vol. 71 , 1985, pp. 283-290.
Koval, Kenneth J., et al., Indirect Reduction and Percutaneous Screw Fixation of Displaced Tibial Plateau Fractures, Journal of Orthopaedic Trauma, vol. 6, No. 3, 1992 Raven Press, Ltd., New York. p. 340-346.

Kram, Harry B., MD. et al., Multisensor transcutaneous oximetric mapping to predict below-knee amputation wound healing: Use of a critical $PO_3$ Journal of Vascular Surgery, vol. 9, No. 6, Jun. 1986, pp. 796-800.
Krishnan, Kartick G., et al., The role of near-infrared angiography in the assessment of post-operative venous congestion in random pattern, pedicled island and free flaps, British Journal of Plastic Surgery, vol. 58, 2005, pp. 320-338.
Kutty, Satish, et al.. The effect of traction on compartment pressures during intramedullary nailing of tibial-shaft fractures: A prospective randomised trial, International Orthopaedics, vol. 29, Jan. 2005, pp. 186-190.
Lantsberg, L. and Goldman, M., Laser Doppler Flowmetry, Transcutaneous Oxygen Tension Measurements and Doppler Pressure Compared in Patients Undergoing Amputation, Eur. J. Vasc. Surg., vol. 5, Apr. 1991, pp. 195-197.
Lewis, D.H., et al., Circulatory Disturbances Following Missile Wounding of Soft Tissue, (University of Gothenburg, Sweden), vol. 16, 1975, pp. 481-493.
Styf, Lundin O., Jr., MD, and Jorma R. Stye, MD, PhD, Intramuscular Pressure in the Leg and Thigh Related to Tensile Strap Force During Knee Brace Wear: An Experimental Study in Man. The American Journal of Sports Medicine, vol. 26, No. 4, Jul.-Aug. 1998, pp. 567-570.
Mancini, Donna M., at al., Validation of near-infrared spectroscopy in humans, J. Appl. Physiol., vol. 77, No. 6. 1994, pp. 2740-2747.
Mars, M., et al., A Comparison of Laser Doppler Fluxmetry and Transcutaneous Okygen Pressure Measurement in the Dysvascuiar Patient Requiring Amputation, Eur. J Vasc. Endovesc. Surg., vol. 16, 1998, pp. 53-58.
Matava, Matthew J., MD, et al., Determination of the Compartment Pressure Threshold of Muscle Ischemia in a Canine Model, The Journal of Trauma. vol. 37, No. 1, Jul. 1994. pp. 50-58.
Iviatsen, Frederick A., III, MD, Compartmental Syndrome, Clinical Orthopaedics and Related Research, vol. 113, Nov.-Dec. 1975, pp. 8-14.
Matsen, Frederick A., III, MD, et al., Increased Tissue Pressure and Its Effects on Muscle Oxygenation in Level and Elevated Human Limbs, Clinical Orthopaedics and Related Research, vol. 144, Oct. 1979, pp. 311-320.
Matsen, Frederick A., III, MD, et al., A Model Compartmental Syndrome in Man with Particular Reference to the Quantification of Nerve Function, The Journal of Bone and Joint Surgery, vol. 59-A, No. 5, Jul. 1977, pp. 648-653.
Matsen, Frederick A., III, MD, et al., Diagnosis and Management at Compartmental Syndromes, The Journal of Bone and Joint Surgery, vol. 62-A, No. 2, Mar. 1980, pp. 286-291.
Mayrovitz, Harvey N., PhD, and Nancy Sims, BSN, RN, CLT-LANA, Effects of Ankle-to-Knee External Pressures on Skin Blood Perfusion Under and Distal to Compression, Advances in Skin & Wound Care, vol. 16, No. 4, Jul.-Aug. 2003, pp. 195-202.
McCully, Kevin K., et al., Exercise-Induced Changes in Oxygen Saturation in the Calf Muscles of Elderly Subjects With Peripheral Vascular Disease, Journal of Gerontology, Biological Sciences, vol. 49, No. 3, May 1994, pp. B128-B134.
McKinley, Bruce A., PhD, et al., Tissue Hemoglobin $O_2$ Saturation during Resuscitation of Traumatic Shock Monitored Using Near Infrared Spectrometry, The Journal of Trauma, vol. 38, No. 4, Apr. 2000, pp. 637-642.
McQueen, M.M., at al., Compartment Pressures After Intramediullary Nailing of the Tibia, The Journal of Bone and Joint Surgery, vol. 72-8, No. 3, May 1990, pp. 395-397.
McQueen, M.M. and C.M. Court-Brown, Compartment Monitoring in Tibial Fractures: The Pressure Threshold for Decompression. The Journal of Bone and Joint Surgery, vol. 76-B, No. 1, Jan. 1998, pp. 99-104.
McQueen, M.M., et al., Acute compartment syndrome: Who is at risk ? The Journal of Bone and Joint Surgery, vol. 82-B, No. 2, Mar. 2000, pp. 200-203.
Moed, Berton R., and P. Kurt Thorderson, A Comparison of the Slit Catheter, Side-Ported Needle, and Simple Needle: Measurement of Intracompartmental Pressure, The Journal of Bone and Joint Surgery (American Volume), vol. 75-A, No. 2, Feb. 1993, pp. 231-235.

(56) References Cited

OTHER PUBLICATIONS

Mohler, L. Randall, MD, et al., Intramuscular Deoxygenation during Exercise in Patients Who Have Chronic Anterior Compartment Syndrome of the Leg, The Journal of Bone and Joint Surgery, vol. 79-A, No. 6, Jun. 1997, pp. 844-849.

Mubarak, Scott, MD, and Charles A. Owen, MD, Compartmental Syndrome and its Relation to the Crush Syndrome: A Spectrum of Disease, Clinical Orthopaedics and Related Research, vol. 113, Nov.-Dec. 1975, pp. 81-89.

Mullett, H, et al., Outcome of compartment syndrome following intramedullary nailing of tibial diaphyseal fractures, Injury, Int. J. Care Injured, vol. 32, 2001, pp. 411-413.

Murkin, John M., et al., Monitoring Brain Oxygen Saturation During Coronary Bypass Surgery: A Randomized, Prospective Study, Anesthesia and Analgesia, vol. 104, No. 1, Jan. 2007, pp. 51-58.

Nakhostine, Manoutch, et al., Intramuscular pressure varies with depth: The tibialis anterior muscle studied in 12 volunteers, Acta Orthop. Scand., vol. 64, No. 3, 1993, pp. 377-381.

Nassif, Jeffrey M., et al., Effect of Acute Reamed Versus Unreamed Intramedullary Nailing on Compartment Pressure When Treating Closed Tibial Shaft Fractures: A Randomized Prospective Study, Journal of Orthdpaedic Trauma, vol. 14, No. *, Nov. 2000, pp. 554-558.

Nioka, Shoko, et al., A novel method to measure regional muscle NIRS kinetics information, Dynamic Medicine, vol. 5, No. 5, May 2006.

Ogunlusi, Johnson D., et al., Compartmental pressure in adults with tibial fracture, International Orthopaedics, vol. 29, 2005, pp. 130-133.

Ozkayin, Nadir and Kemal Aktuglu, Absolute compartment pressure versus differential pressure for the diagnosis of compartment syndrome in tibial fractures, International Orthopaedics, vol. 29, 2005, pp. 396-401.

Pallister, Ian, MBBS. MMED Sci, MD, FRCS, and Katja Empson. MB, ChB, MRCS, The Effects of Surgical Fracture Fixation on the Systemic Inflammatory Response to Major Trauma, Journal of the American Academy of Orthopaedic Surgeons, vol. 13, No. 2, Mar.-Apr. 2005, pp. 93-100.

Patman; R. Don, MD, FACS, Compartmental Syndromes in Peripheral Vascular Surgery, Clinical Orthopaedics and Related Research, vol. 113, Nov.-Dec. 1975, pp. 103-110.

Piantaoosi, C.A., MD, and F.G. Duhaylongsod, MD, Near Infrared Spectroscopy: In Situ Studies of Skeletal and Cardiac Muscle, in Oxygen Transport to Tissue XVI, ed. M.C. Hogan, et al., New York: Plenum Press, 1994, pp. 157-161.

Piantadosi, Claude A., MD, et al. Near-infrared spectrophotometric monitoring of oxygen distribution to intact brain and skeletal muscle tissues, Critical Care Medicine, vol. 14, No. 8, Aug. 1986, pp. 698-706.

Poredos, P., et al., Determination of amputation level in ischaemic limbs using tcPO$_2$ measurement, VASA, vol. 34, 2005, pp. 108-112.

Prayson, Michael J., MD, et al., Baseline Compartment Pressure Measurements in Isolated Lower Extremity Fractures without Clinicai Compartment Syndrome. The Journal of Trauma, vol. 60, No. 5, May 2006, pp. 1037-1040.

Puyana, Juan Carlos, MD et al., Continuous Measurement of Gut pH with Near-Infrared Spectroscopy during Hemorrhagic Shock, The Journal of Trauma, vol. 46, No. 1, Jan. 1999, pp. 9-15.

Qvarfordt, Peter, MD, at al., Intramuscular Pressure, Muscle Blood Flow, and Skeletal Muscle Metabolism in Chronic Anterior Tibial Compartment Syndrome, Clinical Orthopaedics and Related Research, vol. 179, Oct. 1983, pp. 284-290.

Rhee, Peter, MD, et al., Near-Infrared spectroscopy : Continuous measurement to cytochrome oxidation during hemorrhagic shock, Critical Care Medicine, vol. 25, No. 1, Jan. 1997, pp. 166-170.

Seekamp, A., et al, Intramuscular partial oxygen tension monitoring in compartment syndrome—an experimental study, Eur J Emerg Med., vol. 4, No. 4, Dec. 1997, pp. 185-192, Hanover, Germany.

Gagnon, RE., et al., Comparison of two spatially resolved NIRS oxygenation indices, J Clin Monit Comput., vol. 17, Nos. 7-8, Dec. 2002, pp. 385-391, Vancouver, Canada.

Ziad Abouezzi, MD, et al., A Critical Reappraisal of Indications for Fasciotomy After Extremity Vascular Trama, Arch Surg., vol. 133, May 1998, pp. 547-551, Bronx, New York.

Ashton, Heather, Effect of inflatable Plastic Splints on Blood Flow, Brit Med. J., vol. 2, Dec. 10. 1966, pp. 1427-1430.

Ashton, Heather, The Effect of increased Tissue Pressure on Blood Flow, Clinical Orthopaedics and Related Research, Jun. 16, 1975, pp. 15-26, Tyne, England.

Bacharach, Michael, J., et al., Predictive value of transcutaneous oxygen pressure and amputation success by use of supine and elevation measurements, J Vasc Surg, vol. 15, No. 3, Mar. 1992, pp. 558-563, Rochester, Minnesota.

Berkson, Eric M., et al., High-Energy Tibial Plateau Fractures, Copyright © 2006, J Am Acad Orthop Surg, vol. 14, No. 1, Jan. 2006, pp. 20-31, Chicago, Illinois.

Kenneth Bermudez. MD, et al., Fasciotomy, Chronic Venous Insufficiency, and the Calf Muscle Pump, Copyright © 1998 American Medical Association, Arch Surg., vol. 133, Dec. 1998, pp. 1355-1361, San Francisco, California.

Mohit Bhandari, MD, MSc, et at., Surgeons' Preferences for the Operative Treatment of Fractures of the Tibial Shaft, Copyright © 2001, Journal of Bone and Joint Surgery. Incorporated, J Bone and Joint Surg., vol. 83-A, No. 11, Nov. 2001, pp. 1746-1752.

Timothy Bhattacharya, MD, et al., The Medical-Legal Aspects of Compartment Syndrome, Copyright © 2004, Journal of Bone and Joint Surgery, Incorporated, J Bone end Joint Surg., vol. 86-A, No. 4, Apr. 2004, pp. 864-868.

Derdre B. Birtles, et al., Venous Obstruction in Healthy Limbs: A Model for Chronic Compartment Syndrome ?; Copyright © 2003, American College of Sports Medicine, Official Journal of the American College of Sports Medicine, pp. 1638-1644, United Kingdom.

Rolf P. Bochmann, et al., External compression increases forearm perfusion, Copyright © 2005, the American Physiological Society, J Appl Physiol, vol. 99, No. 6, Dec. 2005, pp. 2337-2344.

Susan K. Bonar, MD, et al., Tibial Plafond Fractures: Changing Principles of Treatment, Copyright © 1994, the American Academy of Orthopaedic Surgeons, J Am Acad Othop Surg. vol. 2, No. 6. Nov./Dec. 1994, pp. 297-305.

Antony R. Boody, MD, et al., Accuracy in the Measurement of Compartment Pressures: A Comparison of Three Commonly Used Devices, Copyright © 2005, The Journal of Bone and Joint Surgery, Incorporated, J Bone and Joint Surg., vol. 87-A, No. 11, Nov. 2005, pp. 2415-2422, Loma Linda, California.

O. Bongard, et al., Predicting Amputation in Severe Ischaemia, The Value of Transcutaneous PO$_2$ Measurement, Copyright © 1988 British Editorial Society of Bone and Joint Surgery, J Bone Joint Surg [Br], vol. 70-B, No. 3, May 1988, pp. 465-167, Geneva, Switzerland.

Brett M. Cascio, MD, et al., Documentation of Acute Compartment Syndrome at an Academic Heaith-Care Center; Copyright © 2005, The Journal of Bone and Joint Surgery, Incorporated, J Bone and Joint Surg, vol. 87-A. No. 2, Feb. 2005. pp. 346-350, Baltimore, Maryland.

Giuseppe Caruso, et al., Effect of ischemia on sensory potentials of normal subjects of different ages, Journal of Neurology, Neurosurgery, and Psychiatry, vol. 36, 1973, pp. 455-466, Bari, Italy.

Britton Chance, et al., Recovery from exercise-induced desaturation in the quadriceps muscles of elite competitive rowers, Copyright © 1992, the American Physiological Society, Am. J. Physiol 262 (Cell Physiol. 31), 1992, pp. C766-C775, Athens, Ohio.

T. R. Cheatle, et al., Near-infrared spectroscopy in peripheral disease, Copyright © 1991 Butterworth-Heinemann Ltd., Br. J. Surg., vol. 78, No. 4, Apr. 1991 , pp, 405-408, London, UK.

James M. Clayton, M.D., et al., Tissue Pressure and Perfusion in the Compartment Syndrome, Copyright © 1977 by Academic Press. Inc., journal of Surgical Research, vol. 22, No. 4, Apr. 1977, pp. 333-339, Iowa City, Iowa.

Amy S. Colwell, MD, et al., Detection of Perfusion Disturbances in Digit Replantation Using Near-Infrared Spectroscopy and Serial Quantitative Fluroscopy, The Journal of Hand Surgery, vol. 31A, No. 3, Mar. 2006, pp. 456-462, San Francisco, California.

(56) References Cited

OTHER PUBLICATIONS

Bruce A. Crookes, MD, et al., Can Near-Infrared Spectroscopy identify the Severity of Shock in Trauma Patients ?, Copyright © by Lippincott Williams & Wilkins, The Journal of Trauma Injury, Infection, and Critical Care, vol. 58, No. 4, Apr. 2005, pp. 806-816, San Antonio, Texas.

Dahn, I., et al., Blood Flow in Human Muscles During External Pressure or Venous Stasis, Clin. Sci., vol. 32, 1967, pp. 467-473, Copenhagen, Denmark.

Egol, Kenneth A., et al., Staged Management of High-Energy Proximal Tibia Fractures (OTA Types 41): The Results of a Prospective, Standardized Protocol, Copyright © 2005 by Lippincott Williams & Wilkins, J Orthop Trauma, vol. 19, No. 7, Aug. 2005, pp. 448-455, New York, New York.

Fadel, Paul J., et al., Noninvasive assessment of sympathetic vasoconstriction in human and rodent skeletal muscle using near-infrared spectroscopy and Doppler ultrasound, Copyright © 2005 by the American Physiological Society, Journal of Applied Physiology, vol. 96, Dec. 2, 2003, pp. 1323-1330.

Fadel, Paul J., et al., Augmented sympathetic vasocontruction in exercising forearms of postmenopausal woman is reversed by oestrogen therapy, J Physiol, vol. 581, vol. 3, 2004, pp. 893-901.

Ferrari, Marco, et al., Light source-detector spacing of near-infrared-based tissue oximeters and the influence of skin blood flow, Copyright © 2005 by the American Physiological Society, Journal of Applied Physiology, vol. 100, Apr. 2006, pp. 1426-1427.

Fitzgerald, A.M., et al., Long-term sequelae of fasciotomy wounds; Copyright © 2000 The British Association of Plastic Surgeons, British Journal of Plastic Surgery, vol. 53, 2000, pp. 690-693.

Garfin, Steven R., et al., Quantification of Intracompartmental Pressure and Volume under Plastic Casts, Copyright © 1981 by The Journal of Bone and Joint Surgery, Incorporated, vol. 63-A, No. 3, Mar. 1981, pp. 449-453.

Greensmith, Eric J., et al., Hyperbaric Oxygen Therapy in Extremity Trauma, Copyright © 2004 Orthopaedic Surgeons, vol. 12, No. 6, pp. 376-384.

Grundnes, O., et al., Blood flow and mechanical properties of healing bone: Femoral osteotomies studies in rats, Acta Orthop Scand, vol. 63, No. 5, 1992, pp. 487-491.

Halpern, Alan A., Anterior Compartment Pressures in Patients with Tibial Fractures, Copyright © 1980 by The Williams & Wilkins Co., The Journal of Trauma, vol. 20, No. 9, pp. 786-790.

Hampson, Neil B., Near infrared monitoring of human skeletal muscle oxygenation during forearm ischemia, Copright © 1988 the American Physiological Society, pp. 2449-2457, Durham, North Carolina.

Hargen, Alan R., et al., Effects of Local Compression on Peroneal Nerve Function in Humans, Journal of Orthopaedic Research Society, vol. 11, No. 6, Feb. 23, 1993, pp. 818-827, Boston, Massachusetts.

Harris, Ian A., et al., Continuous Compartment Pressure Monitoring for Tibia Fractures: Does It Influence Outcome?, Copyright © Lippincott Williams & Wilkins, The Jouranl of Trauma Injury, Infection, and Critical Care, Vol, 60, No. 6, Jun. 2006, pp. 1330-1335.

Michael M. Heckman, et al., Compartment Pressure in Association with Closed Tibial Fractures: The Relationship between Tissue Pressure, Compartment, and the Distance from the Site of the Fracture. Copyright © 1994 by the Journal of Bone and Joint Surgery, Incorporated. The Journal of Bone and Joint Surgery (Am. vol.), vol. 76-A(9), Sep. 1994, pp. 1285-1292, Atlanta, Georgia.

R. Bruce Heppenstall, M.D., et al., Compartment Syndrome: A Quantitative Study of High-energy Phosphorus Compounds Using $^{31}$P-magnetic Resonance Spectroscopy, Copyright © 1989 by the Williamd & Wilkins Co., The Journal of Trauma. vol. 29, No. 8, Aug. 1989, pp. 1113-1119, Philadelphia, Pennsylvania.

R. Bruce Heppenstall, M.D., et al., The Compartment Syndrome, An Experimental and Clinical Study of Muscular Energy Metabolism Using Phosphorous Nuclear Magnetic Resonance Spectroscopy, Clinical Orthopaedics and Related Research, No. 226, Jan. 1988, pp. 138-155, Philadelphia, Pennsylvania.

R. Bruce Heppenstall, M.D., et al., A Comparative Study of the Tolerance of Skeletal Muscle to Ischemia, Tourniquet Application Compared with Acute Compartment Syndrome, Copyright © 1986 by the Journal of Bone and Joint Surgery, Incorporated, The Journal of Bone and Joint Surgery, vol. 68-A, No. 6, Jul. 1986, pp. 820-828, Philadelphia, Pennsylvania.

C. H. Rorabeck, M.D., et al., The Pathophysiology of the Anterior Tibial Compartmental Syndrome, Clinical Orthopaedics and Related Research, No. 113, Nov.-Dec. 1975, Jun. 17, 1975, pp. 52-57.

Cecil H. Rorabeck, M.D., et al., The Pathophysiology of the Anterior Tibial Compartment Syndrome : An Experimental Investigation, Copyright © 1978 by The Williams & Wilkins Co., The Journal of Trauma, USA, vol. 18, No. 5, May 1978, pp. 299-304.

Robert T. Ruland, et al., Tibialis Posterior Muscle : The Fifth Compartment?, Copyright © 1992 Raven Press, Ltd., New York, Journal of Orthopaedic Trauma, USA, vol. 6, No. 3, 1992, pp. 347-351.

DS Rush, et al., Does open fasciotomy contribute to morbidity and mortality after acute lower extremity ischemia and revascularization?, J Vasc. Burg, Sep. 1989, vol. 10, No. 3, pp. 343-350.

J. Sandegard, Vasodilation in extremity trauma. Immediate herodynamic changes in the dog hind leg, Acta Chir Scand Suppl, 1974, vol. 447, pp. 1-32.

J. Sandegard, et al., Circulatory Disturbances After Experimental Fracture, Dept. of Surgery I and II and the Depts. of Diagnostic Radiology I and III. Sahlgrenska Sjukhuset. University of Gothenburg, Feb. 12, 1974, pp. 181-192.

E. H. Schemitsch, M.D., et al., Soft-Tissue Blood Flow Following Reamed Versus Unreamed Locked Intramedullary Nailing : A Fractured Sheep Tibia Model, Copyright © 1996 by Lite, Brown and Company, Ann Plast Surg 1996, vol. 36. pp. 70-75.

Oliver Scheufler, M.D., et al., Investigation of TRAM Flap Oxygenation and Perfusion by Near-Infrared Reflection Spectroscopy and Color-Coded Duplex Sonography, Copyright © American Society of Plastic Surgeons, Plastic and Reconstructive Surgery, vol. 113, Jan. 2004, pp. 141-152.

Oliver Scheufler, M.D., et al. Tissue Oxygenation and Perfusion in Inferior Pedicle Reduction Mammaplasty by Near-Infrared Reflection Spectroscopy and Color-Coded Duplex Sonography, Copyright © American Society of Plastic Surgeons, Plastic and Reconstructive Surgery, Vol, 111, Mar. 2003, pp. 1131-1146.

Geoffrey W. Sheridan, M.D., et al., An Animal Model of the Compartmental Syndrome, Clinical Orthopaedics and Related Research, No. 113, Nov.-Dec. 1975, Jun. 17, 1975, pp. 36-42.

Geoffrey W. Sheridan, M.D., et al.. Fasciotomy in the Treatment of the Acute Compartment syndrome, The Journal of Bone and Joint Surgery, vol. 58-A, No. 1, Jan. 1976, pp. 112-115.

Ian Shrier, et al., Effects of adenosine on pressure-flow relationships in an in vitro model of compartment syndrome, Copyright © 2005 by the American Physiology Society, J Appl Physiol, vol. 82, pp. 755-759, 1997.

Brendan C. Stack Jr., M.D., et al., Initial Experience with Personal Digital Assistant-Based Reflectance Photoplethysmograph for Free Tissue Transfer Monitoring. Copyright © 2003 by Lippincolt Williams & Wilkins, Inc., Ann Plast Surg., Aug. 2003, vol. 51, No. 2. pp. 136-140.

Jorma Styf, MD, The influence of external compression on muscle blood flow during expercise, Copyright © 1990 American Orthopaedic Society for Sports Medicine, Sports Medicine, vol. 18, No, 1, 1990, pp. 92-95.

Jorma Styf, MD, PhD, et al., Abnormally Increased Intramuscular Pressure in Human Legs: Comparison of Two Experimental Models, Copyright © Williams & Wilkins 1998, The Journal of Trauma: Injury, infection, and Critical Care, vol. 46(1), Jul. 1998, pp. 133-139.

Georg Taeger, MD, et al., Damage Control Orthopedics in Patients With Multiple Injuries is Effective, Time Saving, and Safe, Copyright © Lippincott Williams & Wilkins, The Journal of Trauma: Injury, Infection, and Critical Care, vol. 59, No, 2, Aug. 2005, pp. 408-415.

Virak Tan, of al., Well-Leg Compartment Pressures During Hemilithotomy Position for Fracture Fixation, Copyright © 2000 Lippincott Williams & Wilkins, Inc., J Orthop Trauma, vol. 14, No. 3, Mar./Apr. 2000, pp. 157-161.

David B. Thordarson, MD, Complications After Treatment of Tibial Pilon Fractures: Prevention and Management Strategies, Copyright

(56) References Cited

OTHER PUBLICATIONS

® 2000 by the American Academy of Orthopaedic surgeons, J Am Mad Orthop Surg, vol. 8, No. 4, Jul./Aug. 2000, pp. 253-265.

George J, Tischenko, M.D., et al., Compartment Syndrome after Intramedullary Nailing of the Tibia, Copyright © 1990 by The Journal of Bone and Joint Surgery, Incorporated, J. Bone and Joint Surg., vol. 72-A, No. 1, Jan. 1990, pp. 41-44.

Paul Tornetta III, Compartment Pressures During Nonreamed Tibial Nailing without Traction, Copyright © Lippincott-Raven Publishers, J Orthop Trauma, vol. 11, No. 1, Jan. 1997, pp. 24-27.

Paul Tornetta III, et al., Instructional Course Lectures, The American Academy of Orthopaedic Surgeons—Compartment Syndrome Associated with Tibial Fracture*{{dagger}}, J. Bone Joint. Surg. Am., vol. 78-A, No. 9, Sep. 1996, pp. 1438-1444.

P. D. Triffitt, et al., Compartment Pressures After Closed Tibial Shaft Fracture, Their Relation to Functional Outcome, Copyright ©1992 British Editorial Society of Bone and Joint Surgery, J Bone Joint Surg Br., vol. 74-B, No. 2, Mar. 1992, pp. 195-198.

Frank Tull, MD, et al., Soft-Tissue injury Associated With Closed Fractures: Evaluation and Management, Copyright 2003 by the Journal of the American Academy of Orthopaedic Surgeons, vol. 11, No. 6, Nov./Dec. 2003, pp. 431-438.

Annemarie Uliasz, et al., Comparing the Methods of Measuring Compartment Pressures in Acute Compartment Syndrome, Copyright © 2003, Elsevier Science (USA), American Journal of Emergency Medicine, vol. 21, No. 2, Mar. 2003, pp. 143-145.

Todd Ulmer, The Clinical Diagnosis of Compartment Syndrome of the Lower Leg: Are Clinical Findings Predictive of the Disorder?, Copyright © 2002 Lippincott Williams & Wilkins, Inc., J Orthop Trauma, vol. 16, No. 8, pp. 572-577.

Johan G. H. Van Den Brand, MD, PhD, et al., The Diagnostic Value of intracornpartmental Pressure Measurement, Magnetic Resonante Imaging, and Near-infrared Spectroscopy in Chronic Exertional Compartment Syndrome, A Prospective Study in 50 Patients, Copyright © 2005 American Orthopaedic Society for Sports Medicine, Am J Sports Med., vol. 33, No. 5, 2005, pp. 699-704.

J. Esteban Varela, MD, et al., Near-infrared spectroscopy reflects changes in mesenteric and systemic perfusion during abdominal compartment syndrome, Copyright © 2001 by Mosby, Inc., Surgery, Mar. 2001, pp. 363-370.

Brigitte Vollmar, MD, et al., Microvascular Response to Compartment. Syndrome-Like External Pressure Elevation : An In Vivo Fluorescence Microscopic Study in the Hamster Striated Muscle, Copyright © 1990 Lippincott Williams & Wilkins, Inc., The Journal of Trauma: Injury, Infection, and Critical Care, vol. 46, No. 1, Jan. 1999, pp. 91-96.

Gary Weiner, et al., Effect of Ankle Position and a Plaster Cast on Intramuscular Pressure in the Human Leg, Copyright © 1994 by the Journal of Bone and Joint Surgery, Incorporated, J Bone and Joint Surg. [Am], vol. 76-A, No. 10, Oct. 1994, pp. 1476-1481.

Michael S. Weingarten, MD, et al., Measurement of optical properties to quantify heating of chronic diabetic wounds, Copyright © 2006 by the Wound Healing Society, Wound Rep Reg, 2006, vol. 14, pp. 364-370.

Timothy O. White, BMedSci, AFRCS, et al., Elevated Intramuscular Compartment Pressures Do Not Influence Outcome after Tibial Fracture, Copyright © Lippincott Williams & Wilkins, The Journal of Trauma: Injury, Infection, and Critical Care, vol. 55, No. 6, Dec. 2003, pp. 1133-1138.

Thomas E. Whitesides, Jr., M.D., et al., Tissue Pressure Measurements as a Determinant for the Need of Fasciotomy, Clinical Orthopaedics and Related Research, No. 113, Nov.-Dec. 1975, pp. 43-51.

The Parameters of Muscle Ischemia, Acceptance Paper, Kappa Delta Award, AAOS-ORS, Feb. 1980, pp. 1-10.

Thomas E. Whitesides, Jr., M.D., et al., Compartment syndromes and the role of fasciolcimy, and techniques, Orthopaedic complications, Chapter 18, pp. 179-196.

John M. Wiemann, MD, et al., Noninvasive Measurements of Intramuscular Pressure Pulsed Phased-locked Loop Ultrasound for Detecting Compartment Syndromes, A Preliminary Report, Copyright © 2006 by Lippincott Williams & Wilkins, J Orthop Trauma, vol. 20, No, 7, Aug. 2006, pp. 458-463.

Per Wiger, et at., The effects of limb elevation and increased intramuscular pressure on nerve and muscle function in the human leg, Copyright © Springer-Verlag 2000, Eur J Appl Physiol., Sep. 2000, vol. 83, No. 1, pp. 84-88.

Arthur B. Williams, MD, et al., The effect of early versus late fasciotomy in the management of extremity trauma, Copyright © 1997 by Mosby-Year Book, Inc., Surgery, Oct. 1997, pp. 861-866.

I. M. Williams, et al., Recent Developments in Cerebral Monitoring—Near-infrared Light Spectroscopy. An Overview, Copyright © 1996 W. B. Saunders Company Ltd., Eur J Vasc Endovasc Surg., vol. 12, Oct. 1996, pp. 263-271.

JR Wilson, et al., Noninvasive detection of skeletal muscle underperfusion with near-infrared spectroscopy in patants wth heart failure, Copyright © 1989 American Heart Association, Circulation, vol. 80, No. 6, Dec. 1989, pp. 1668-1674.

Ursula Wolf, MD, et al., Localized irregularities in hemoglobin flow and oxygenation in calf muscle in patients with peripheral vascular disease detected with near-infrared spectrophotometry, Copyright © 2003 by The Society for Vascular Surgery and the American Association for Vascular Surgery, vol. 37, No. 5, May 2003, pp. 1017-1026.

Patricia Zaramella, MD, et at., Foot Pulse Oximeter Perfusion Index Correlates with Calf Muscle Perfusion Measured by Near Infrared Spectroscopy in Healthy Neonates, Copyrght © 2005 Nature Publishing Group, Journal of Perinatology (2005), vol. 25, pp. 417-422.

Qiuxia Zhang, et al., A non-invasive measure of changes in blood fow in the human anterior tbial muscle, Copyright © Springer-Verlag 2001, Eur J Appl Physiol., Mar. 29, 2001, pp. 1-10.

Scott A. Lemaire, et at., Transcutaneous near-infrared spectroscopy for detection of regional spinal Ischemia during intercostal artery ligation : Preliminary experimental results, Copyright © 2006 American Association for Thoracic Surgery, J Thorac Cardiovasc Surg, Nov. 2006, vol. 132, pp. 1150-1155.

Aaron G. Hill, BS, CCP, Enhancing Patient Care through Cerebral Oximetry, MEEN, Acuity Care/Technology, Dec. 2006/Jan. 2007, vol. 46, No. 6, pp. 23.

J. P. Slater, et al., Prolonged intraoperative Forebrain Desaturation Predicts Cognitive Decine After Cardiac Surgery, The Society of Thoracic Surgeons, Jan. 29, 2007.

Kim, Michael B., et al., Estimation of jugular Venous $O_2$ Saturation from Cerebral Oximetry or Arterial $O_2$ Saturation During Isocapnic Hypoxia, Journal of Clinical Monitoring and Computing, vol. 16, No. 3, Jan. 31, 2000, pp. 191-199.

Davis, Scott, L., et al., Skin blood flow influences near-infrared spectroscopy-derived measurements of tissue oxygenation during heat stress, J Appl Physiol, vol. 100, Jan. 2006, pp. 221-224.

Wassenaar, E.B., MD, et al., Reliability of Near-Infrared Spectroscopy in People with Dark Skin Pigmentation, Journal of Clinical Monitoring and Computing, vol. 19, No. 3; Feb. 1, 2005, pp. 195-199.

Comerota, Anthony J., M.D., et al., Tissue (muscle) oxygon saturation ($St0_2$): A new measure of symptomatic lower-extremity arterial disease.

Costes, F.: el. al., Age-Associated Alteration of Muscle Oxygenation Measured by Near Infrared Spectroscopy During Exercise, Archives of Physiology and Biochemistry, 1999, vol. 107, No. 2, pp. 159-167.

Breit, Gregory A. PHD, et al., Near-Infrared Spectroscopy for Monitoring of Tissue Oxygenation of Exercising Skeletal Muscle in a Chronic Compartment Syndrome Model, The Journal of Bone & Joint Surgery, vol. 79-A, Jun. 6, 19997, pp. 838-843.

Sandegard, J. et al., Angiography and Hemodynamic Measurements in Extensive Soft Tissue Trauma to the Extremity; From the Departments of Surgery 1 and II and the Department of Diagnostic Radiology 1 and III, Sahlrengska Sjukhuset: University of Gothenburg, S-413 45 Gothenburg; Sweden, Mar. 28, 1974, pp. 279-296.

Arbabi, Saman MD, et al., Near-Infrared Spectroscopy: A Potential Method for Continuous, Transcutaneous Monitoring for Compartmental Syndrome in Critically Injured Patients, The Journal of Trauma, vol. 47(5), Nov. 1999, pp. 829-839.

(56) References Cited

OTHER PUBLICATIONS

Giannotti: Giovanni, M.D., et al., Utility of Near-Infrared Spectroscopy in the Diagnosis of Lower Extremity Compartment Syndromo, The Journal of Trauma: Injury, Infection, and Critical Care, vol. 48, No. 3, Dec. 8, 1999. pp. 396-401.
Gentilello, Larry M., MD; et al., Near-Infrared Spectroscopy versus Compartment Pressure for the Diagnosis of Lower Extremity Compartmental Syndrome Using Electromyography-Determined Measuroments of Neuromuscular Function, The Journal of Trauma® Injury, Infection, and Critical Care, vol. 51, No. 1, Mar. 12, 2001, pp. 1-9.
Garr, Jeff, L. MD, et al., Monitoring for Compartmental Syndrome Using Near-Infrared Spectroscopy: A Noninvasive, Continuous: Transcutaneous Monitoring Technique, The Journal of Trauma Injury, Infection and Critical Care, vol. 46(4), Apr. 1999, pp. 613-818.
Tobias, Joseph D., MD, et al., Near-Infrared Spectroscopy Identifies Compartment Syndrome in an Infant, J Pediatr Ortho, vol. 27, No. 3, Apr./May 2007, pp. 311-313.
Clayton, James M., MD, et al., Tissue Pressure and Perfusion in the Compartment Syndrome; Journal of Surgical Research 22, Copyright © 1977 by Academic Press, Inc., Journal of Surgical Research 22, pp. 333-339.
Heppenstall, R. Bruce, MD, et al., A Comparative Study of the Tolerance of Skeletal Muscle to Ischemia, Copyright 1986, The Journal of Bone and Joint Surgery, pp. 820-828.
Matava, Matthew J., M.D., et al., Determination of the Compartment Pressure Threshold of Muscle Ischemia in a Canine Model, The Journal of Trauma, Copyright 1994, vol. 37, No. 1, pp. 50-58.
Dahn, I, et al., Blood Flow in Humin Muscles During External Pressure or Venous Stasis, Clinical Science (1967) 32, pp. 467-473.
Chan, Joanna L., et al., Assessing the Role of Race in Quantitative Measures of Skin Pigmentation and Clinical Assessments of Photosensitivity, Journal American Academy Dermatology, 2005 vol. 52, pp. 609-615.
Clarys, P., et al., Skin Color Measurements: Comparison between three instruments: the Chromameter®, the DermaSpectrometer® and Mexameter®, Skin Research and Technology, 2006, vol. 6, pp. 230-238.
Farr, P.M., et al., The Erythemal Response of Human Skin to Ultraviolet Radiation, British Journal of Dermatology, 1985, vol. 113, pp. 65-76.
Ferguson-Pell, M. et al., An Empirical Technique to Compensate for Melanin when Monitoring Skin Microcirculation Using Reflectance Spectrophotometry, Med. Eng. Phys., 1995, vol. 17, No. 2, pp. 104-110.
Queille-Roussel, Catherine, et al., Quantification of Skin-Colour Changes Induced by Topical Corticosteriod Preparations Using the Minolta Chrome Meter, British Journal of Dermatology, 1991, vol. 124, pp. 264-270.
Shimada, M., et al., Melanin and Blood Concentration in Human Skin Studied by Multiple Regression Analysis: Experiments, Institute of Physics Publishing, Phys. Med. Biol vol. 46, 2001, pp. 2385-2395.
Shimada, M. et al., Melanin and Blood Concentration in Human Skin Model Studied by Multiple Regression Analysis: Assessment by Monte Carlo Simulation, Physics in Medicine and Biology, vol. 46, 2001; pp. 2397-2406.

Taylor, Susan, MD, et al., Noninvasive Techniques for the Evaluation of Skin Color, J Am Acad Dermatol, May 2006, vol. 54, pp. S282-S290.
Yang Ye, at al., Simultaneous Correction of the Influence of Skin Color and Fat on Tissue Spectroscopy by Use of a Two-Distance Fiber-Optic Probe and Orthogonalisation Technique, Optical Society of America, Sep. 1, 2005, vol. 30, No. 17, pp. 2269-2271.
Anthony R. Young. Chromophores in Human Skin, Phys. Med. Biol. vol. 42, 1997, pp. 789-802.
"Use of Near Infrared Spectroscopy to Identify Traumatic Intracranial Hematomas" Robertson at at Journal of Biomedical Optics 2(1), 31-41. Jan. 1997.
Comerota et al. "Tissue (muscle) oxygen saturation (StO2): a new measure of symptomatic lower-extremity arterial disease." J Vasc Surg. Oct. 2003;38(4):724-9.
Giannotti et al. "Utility of near-infrared spectroscopy in the diagnosis of lower extremity compartment syndrome." J Trauma. Mar. 2000;48(3):396-9; discussion 399-401.
Lundin et al. "Intramuscular pressure in the leg and thigh related to tensile strap force during knee brace wear. An experimental study in man." Am J Sports Med. Jul.-Aug. 1998;26(4):567-70.
Prayson et al. "Baseline compartment pressure measurements in isolated lower extremity fractures without clinical compartment syndrome." J Trauma. May 2006;60(5):1037-40.
Uliasz et al. "Comparing the methods of measuring compartment pressures in acute compartment syndrome." Am J Emerg Med. Mar. 2003;21(2):143-5.
Whitesides et al. "Compartment syndromes and the role of fasciotomy, its parameters and techniques." Orthopaedic Complications. St Louis: Mosby, 1977: 179-196.
Garr, Jeff L. et al. "Monitoring for Compartmental Syndrome Using Near-Infrared Spedroscopy: A Noninvasive, Continuous, Transcutaneous Monitoring Technique." The Journal of Trauma: Injury, Infection, and Critical Care; vol. 46, No. 4, Apr. 1999, pp. 613-618.
"Compartment Syndrome." Wheeless' Textbook of Orthopaedics. Dec. 2, 2006. http://web.archive.org/web/20061202094948/http://www.wheelessonline.com/ortho/compartment_syndrome.
"Reducing False Alarms in the Intensive Care Unit: A Systematic Comparison of Four Algorithms." Proceedings of the AMIA Annual Fall Symposiu, (1997). vol. 4, Issue: SUPPL., Publisher: American Medical Informatics Association, p. 894.
MJ Hope et al.: "Invasive and Non-Invasive Monitoring for Compartment Syndrome," Jan. 1, 2003, XP055153168, Retrieved from the Internet: URL:http://bjjprocs.boneandjoint.org.uk/content/85-B/SUPP I/9.2.short (Abstract Only).
Katharine Hunt et al.: "Changes in cerebral oxygenation and haemodynamics during postural blood pressure changes in patients with autonomic failure", Physiological Measurement, vol. 27, No. 9, Jun. 14, 2006, pp. 777-785, XP055153437, ISSN: 0967-3334, DOI: 10.1088/0967-3334/27/9/002.
Breit G A et al.: Near-infrared spectroscopy for monitoring of tissue oxygenation of exercising skeletal muscle in a chronic compartment syndrome model, Journal of Bone and Joint Surgery, American Volume, Journal of Bone and Joint Surgery, US, vol. 79, No. 6, Jun. 1, 1997, pp. 838-843, XP002670130, ISSN: 0021-9355 (Abstract Only).

\* cited by examiner

FIG. 1
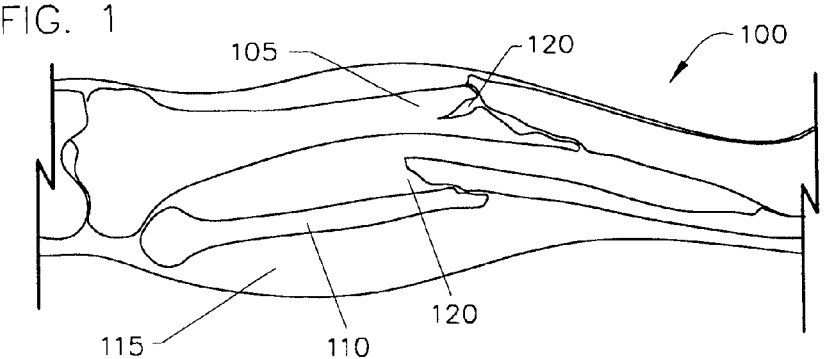
FIG. 2
PRIOR ART
FIG. 3
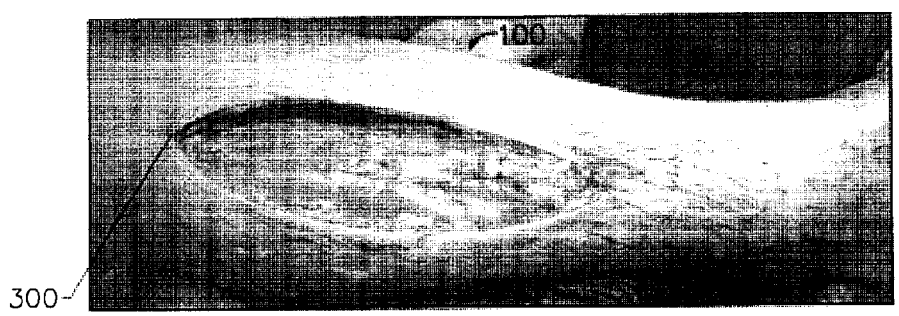

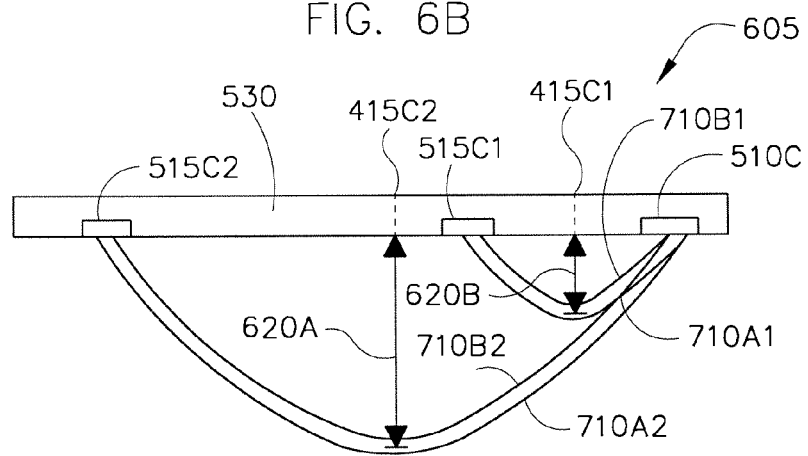
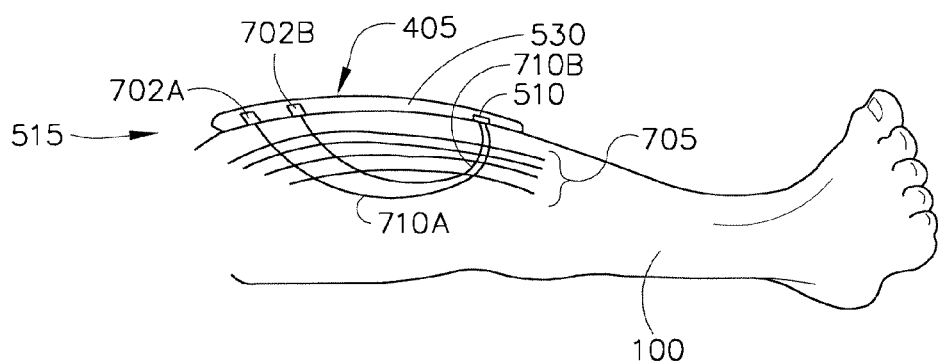
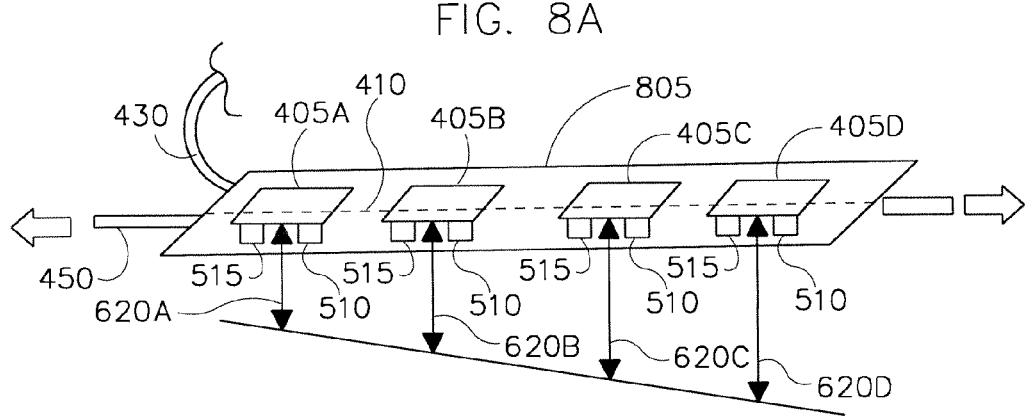

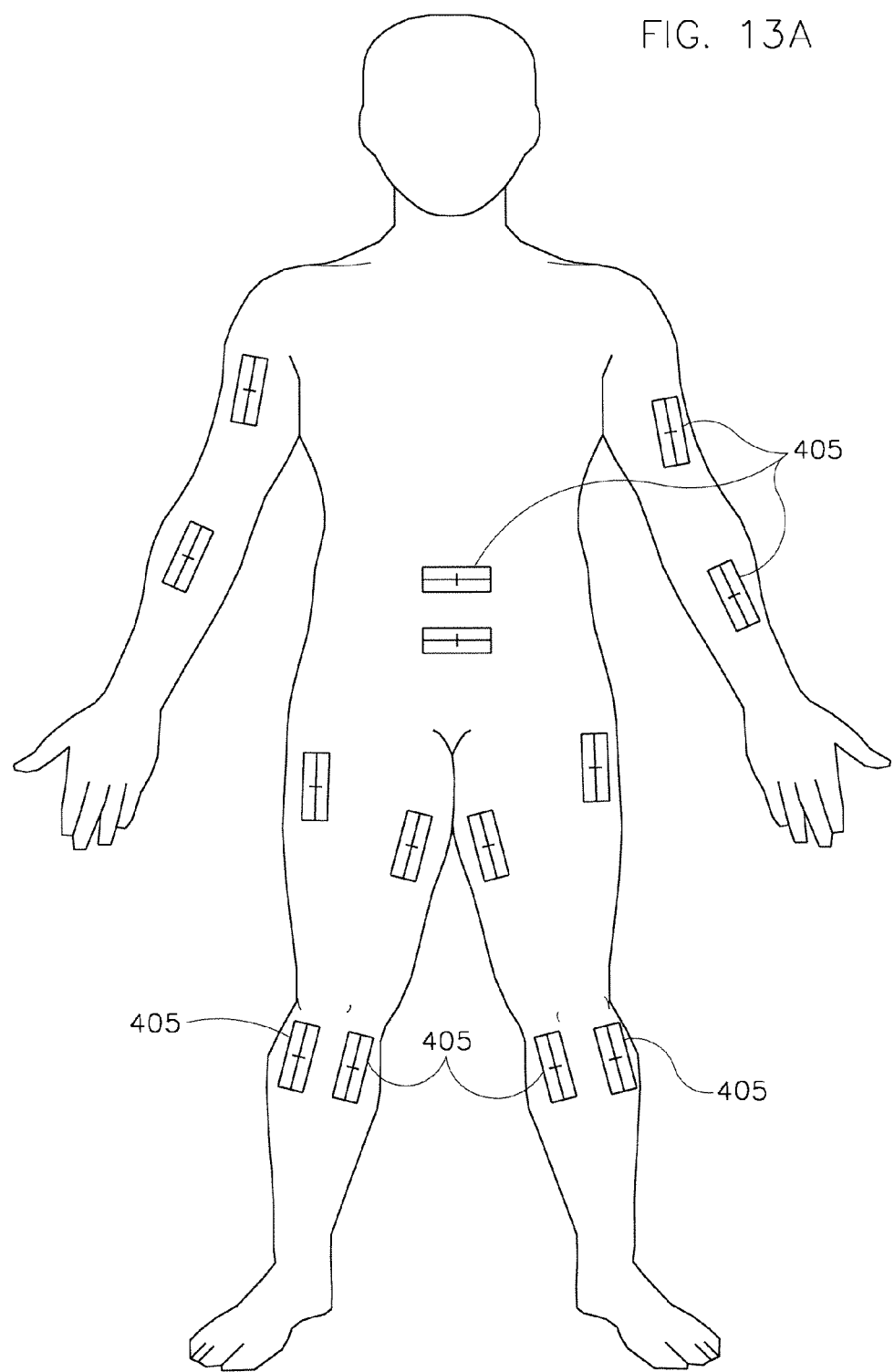

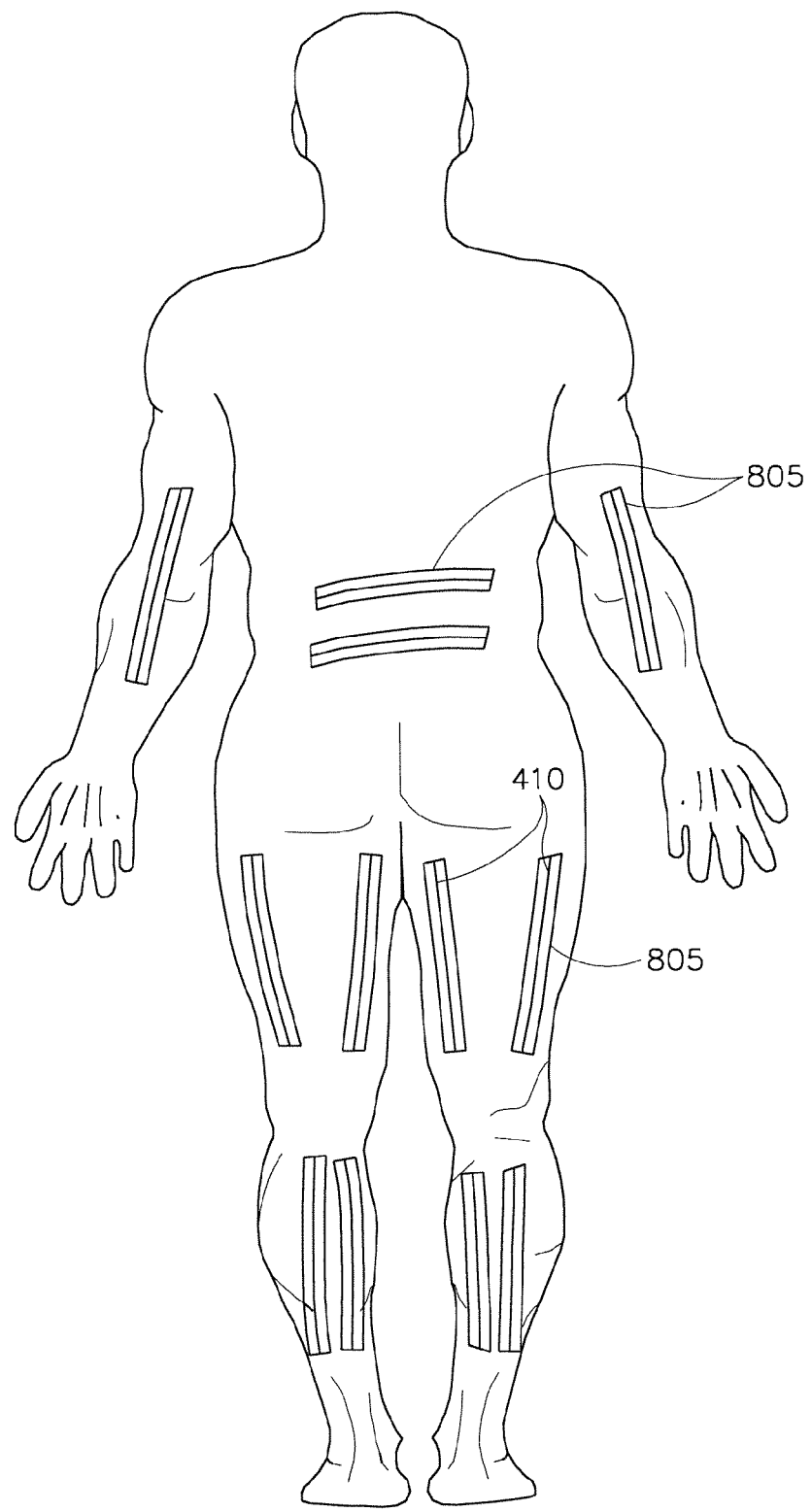

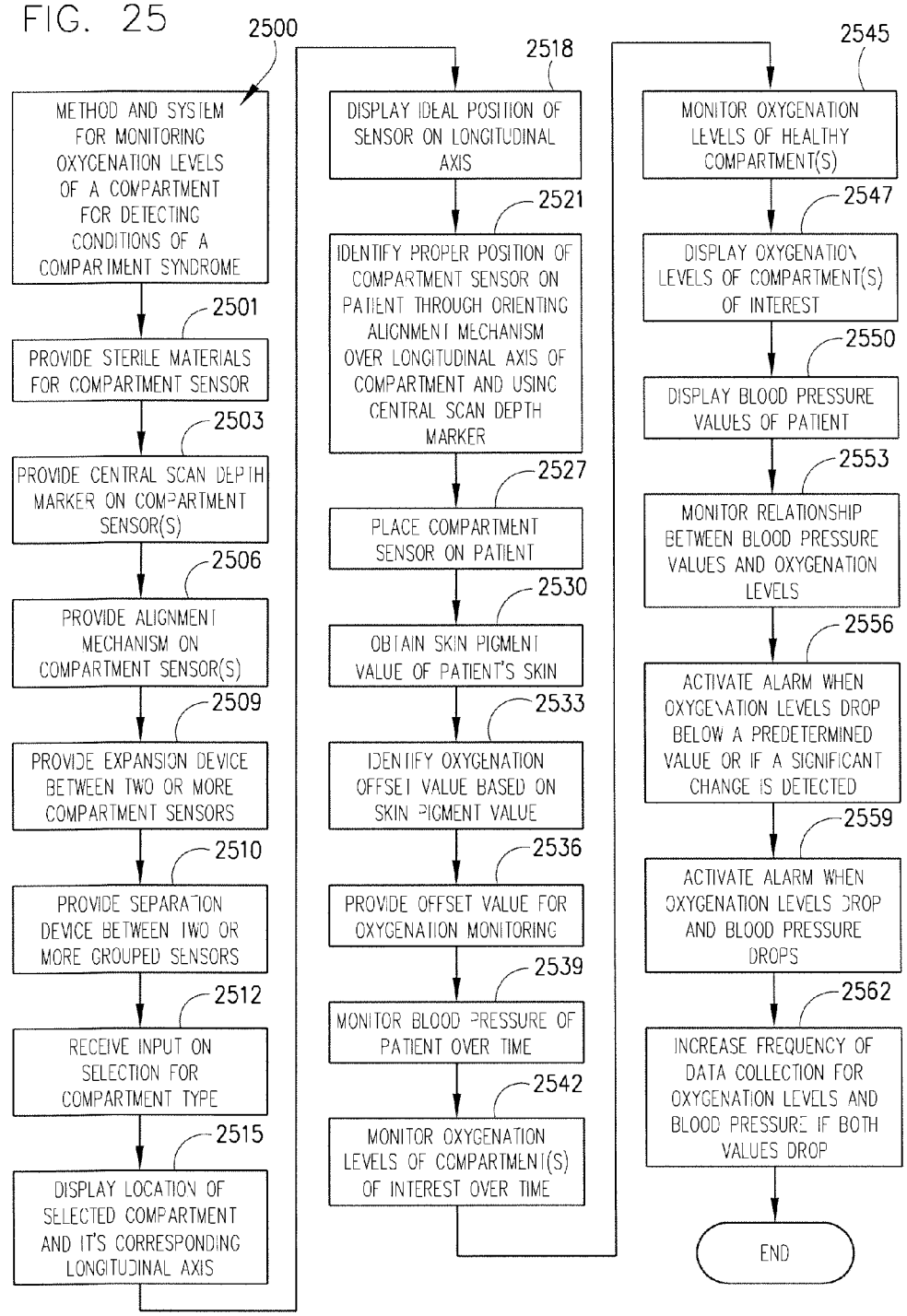

METHOD AND SYSTEM FOR MONITORING OXYGENATION LEVELS OF A COMPARTMENT FOR DETECTING CONDITIONS OF A COMPARTMENT SYNDROME

REFERENCE TO RELATED APPLICATIONS

The present application claims priority to provisional patent application entitled, "Near Infrared Compartment Syndrome (NICS) Monitor," filed on Feb. 27, 2007 and assigned U.S. Application Ser. No. 60/903,632. The entire contents of the provisional patent application mentioned above is hereby incorporated by reference.

FIELD OF INVENTION

The invention relates to a coordinated, continual and real-time method and system for monitoring oxygenation levels of a compartment in order to detect conditions that are likely caused by a compartment syndrome. More particularly, the invention relates to an orchestrated method and system that monitors oxygenation levels and that is provided with sensors having markers so that the sensors can be precisely positioned over a compartment of interest in order to assist with a compartment syndrome diagnosis.

BACKGROUND OF THE INVENTION

Compartment syndrome is a medical condition where the pressure inside a compartment, which is a muscle group surrounded by fascia or a thin, inelastic film, increases until the blood circulation inside the volume defined by the fascia or thin film is cut off. The most common site, in humans, occurs in the lower leg, and more specifically, in regions adjacent to the tibia and fibula. There are four compartments in the lower, human leg: the anterior (front), lateral (side next to the fibula) and the deep and superficial posterior (back).

These four compartments surround the tibia and fibula. Anyone of these four compartments can yield a compartment syndrome when bleeding or swelling occurs within the compartment. Compartment syndrome usually occurs after some trauma or injury to the tissues, such as muscles or bones or vessel (or all three), contained within the compartment. Bleeding or swelling within a compartment can cause an increase in pressure within that compartment. The fascia does not expand, so as pressure rises, the tissue and vessels begin to be compressed within the compartment.

This compression of tissue, such as muscle, due to intra-compartmental pressure can restrict and often times stop blood flow from entering the compartment that is destined for any tissues contained within the compartment. This condition is termed ischemia. Without blood flow to tissues, such as muscle, the tissues will eventually die. This condition is termed necrosis.

A simple working definition for a compartment syndrome is an increased pressure within a closed space which reduces the capillary blood perfusion below a level necessary for tissue viability. As noted above, this situation may be produced by two conditions. The first condition can include an increase in volume within a closed space, and the second condition is a decrease in size of the space.

An increase in volume occurs in a clinical setting of hemorrhage, post ischemic swelling, re-perfusion, and arterial-venous fistula. A decrease in size results from a cast that is too tight, constrictive dressings, pneumatic anti-shock garments, and closure of fascial defects. As the pressure increases in tissue, it exceeds the low intramuscular arteriolar pressure causing decreased blood in the capillary anastomosis and subsequent shunting of blood flow from the compartment.

The clinical conditions that may be associated with compartment syndrome include the management of fractures, soft tissue injuries, arterial injuries, drug overdoses, limb compression situations, burns, post-ischemic swelling, constrictive dressings, aggressive fluid resuscitation and tight casts.

Referring now to the Figures, FIG. 1 illustrates an X-ray view of a human leg 100 with fractured bones of the tibia 105 and fibula 110 that lead to one or more compartment syndromes in the muscles 115 surrounding the bones of the human leg 100. The tibia 105 and fibula 110 usually bleed in regions proximate to the physical break regions 120. This bleeding can form a large pool of stagnant blood referred to as a hematoma. The hematoma can start pressing upon muscles 115 that may be proximate to the break 120. This pressure caused by the hematoma can severely restrict or stop blood flow into the muscles 115 of a compartment, which is the diagnosis of a compartment syndrome.

Traditional Methods for Diagnosing Compartment Syndromes

Referring now to FIG. 2, this Figure is a side view of a human leg 100 in which compartment pressures are being measured with a large bore needle 200, having a gauge size such as 14 or 16 (which is the largest needle in the hospital available to clinicians), according to a conventional method known in the prior art. While compartment pressures can be measured with this conventional method, the method is highly invasive procedure which can cause tremendous pain to the patient. Needles with large gauge sizes of 14 or 16 are analogous to sticking a patient with an object as large as a nail or a pen.

In addition to causing tremendous pain to the patient, there are several more problems associated with the conventional needle measuring method. First, it is very challenging for a medical practitioner to actually measure or read pressure of a compartment since the needle must be positioned at least within the interior of a compartment. To enter the interior of a compartment, the needle 200 must penetrate through several layers of skin and muscle. And it is very difficult for the medical practitioner to know if the needle has penetrated adequately through the intermediate layers to enter into the compartment. This challenge significantly increases if the patient being measured is obese and has significant amounts of subcutaneous fat in which to penetrate with the needle.

Often, the medical practitioner may not have a needle accurately positioned inside a compartment which can yield a reading of the tissue adjacent to the compartment, such as muscle or skin. Such a reading of muscle or skin instead of the compartment of interest can provide the medical practitioner with elevated or depressed pressure readings that do not reflect the actual pressure contained within the compartment of interest. Pressure readings inside a compartment have been shown to vary (increase) based on the depth of the reading as well as the proximity to the fracture site.

Because of the challenge medical practitioners face with precisely positioning a needle within a compartment of interest and because of the numerous law suits associated with the diagnosis of compartment syndrome, many medical schools do not provide any formal training for medical practitioners to learn how to properly place a needle within a compartment of interest for reading a compartment's pressure. Therefore, many medical practitioners are not equipped with the skills or experience to accurately measure compartment pressures with the needle measuring method.

Currently, intra-compartmental pressures are the only objective diagnostic tool. Due to the legal climate regarding this condition, clinicians are forced to treat an elevated value for compartment pressures or expose themselves to legal ramifications with any complications. As described later, the treatment of compartment syndrome can cause significant morbidity and increase the risk for infection. Therefore inaccurate and elevated pressure readings are a very difficult and potential dangerous pitfall.

Another problem associated with the training and experience required for the needle measuring method is that, as noted above, compartment syndromes usually occur when tissues within the compartment are experiencing unusual levels of swelling and pressure. With this swelling and pressure, the tissues do not have their normal size. Therefore, any training of a medical practitioner must be made with a patient suffering under these conditions. A normal patient without any swelling would not provide a medical practitioner with the skills to accurately assess a size of a compartment when using the needle measuring method for determining compartment pressure. Put another way, due to the trauma associated with the injury, normal anatomy is not always present when attempting to measure compartment pressures.

In addition to the problem of entering a compartment that may have an abnormal size or anatomy, the needle measuring method has the problem of providing only a snap-shot of data at an instant of time. When the conventional needle measuring method is used, it provides the medical practitioner with pressure data for a single instant of time. In other words, the needle pressure method only provides the medical practitioner with one data point for a particular time. Once pressure is read by the medical practitioner, he or she usually removes the needle from the patient. The data obtained from a single measurement in time gives no information concerning the pressure trend, and the direction the intra-compartmental pressure is moving.

This collection of single data points over long periods of time is usually not very helpful because pressures within a compartment as well as the patient's blood pressure can change abruptly, on the order of minutes. Also, because of the pain associated with the needle measuring method noted above, the medical practitioner will seldom or rarely take pressure readings within a few minutes of each other using a needle.

A further problem of the needle measuring method is that for certain regions of the body, such as the lower leg, there are four compartments to measure. This means that a patient's leg must be stuck with the large bore needle at least four times in order for a medical practitioner to rule out that a compartment syndrome exists for the lower leg. In the lower leg of the human body, one compartment is located under a neighboring compartment such that a needle measurement may be needed in at least two locations that are very close together, but in which the medical practitioner must penetrate tissues at a shallow depth at a first location to reach the first compartment; and for reaching the second compartment that is underneath the first compartment, a large depth must be penetrated by the needle, often with the needle piercing the first compartment and then the second compartment.

Another problem, besides pain that is associated with the needle pressure measuring method, is that there is a lack of consensus among medical practitioners over the compartment pressure ranges which are believed to indicate that a compartment syndrome may exist for a particular patient. Normal compartment pressure in the human body usually approaches 4 mmHg in the recumbent position. Meanwhile, scientists have found that an absolute pressure measurement of 30 mmHg in a compartment may indicate presence of compartment syndrome. However, there are other scientists who believe that patients with intracompartmental pressures of 45 mmHg or greater should be identified as having true compartment syndromes. But other studies have shown patients with intra-compartmental pressures above these limits with no clinical signs of compartment syndrome. Additional studies have shown that a pressure gradient based on perfusion pressure (diastolic blood pressure minus intra-compartmental pressure) is the more important variable. Studies have shown in a laboratory setting that once the perfusion pressure drops to 10 mm Hg tissue necrosis starts to occur.

Other subjective methods for diagnosing compartment syndromes instead of the needle measuring method exist, however, they may have less accuracy than the needle measuring method because they rely on clinical symptoms of a patient. Some clinical symptoms of a patient used to help diagnose compartment syndromes include pulselessness (absence of a pulse), lack of muscle power, pain, parastesias, and if the flesh is cold to touch. Pain out of proportion and with passive stretch are considered the earliest and most sensitive, but both have very low specificity. One of the major drawbacks of these symptoms is that for many of them the patient must be conscious and must be able to respond to the medical practitioner. This is true for the muscle power and pain assessment. For any inebriated patients or patients who are unconscious, the pain assessment and muscle power assessment cannot be used accurately by the medical practitioner. In the setting of high energy trauma which is associated with compartment syndrome, many patients are not capable of cooperating with a good physical exam due to any number of causes including head trauma, medical treatment (including intubation), drug or alcohol ingestion, neurovascular compromise or critical and life threatening injuries to other body systems.

For the pain assessment, if a lower leg compartment syndrome exists in a patient, then the range of motion for a patient's foot or toes will be extremely limited and very painful when the patient's foot or toes are actively or passively moved. The pain from a compartment syndrome can be very immense because the muscles are deprived of oxygen because of the compartment syndrome.

Another drawback using pain to assess the likelihood of a compartment syndrome is that every human has a different threshold for pain. This means that even if someone should be experiencing a high level of pain, he or she may have a high threshold for pain and therefore, not provide the medical practitioner with a normal reaction for the current level of pain. Another problem with using pain to assess the likelihood of the existence of a compartment syndrome is that if the patient is experiencing trauma to other parts of their body, he or she may not feel the pain of a compartment syndrome as significantly, especially if the trauma to the other parts of the patient's body is more severe. This condition is termed a distracting injury. On the other hand, trauma causes the initial injury that precipitates a compartment syndrome. That initial trauma by definition will cause a baseline amount of pain that is often very difficult to separate from a potential compartment syndrome pain. These initial injuries by themselves cause significant pain, so a patient that does not tolerate pain well may present similar to a compartment syndrome without having any increased pressures simply because they react vehemently to painful conditions.

Conventional Non-Invasive Techniques for Measuring Oxygenation Levels of a Compartment Non-invasive measuring of compartment syndromes using near infrared sensors, such as spectrophotometric sensors, to measure oxygenation levels within a compartment has been suggested by the conventional art. However, these conventional techniques have encountered the problem of a medical practitioner locating compartments of interest and accurately and precisely positioning a sensor over a compartment of interest. Often the orientation of the scan and the depth of the scan produced by a near infrared sensor as well as the orientation of a compartment can be challenging for a medical practitioner to determine because conventional sensors are not marked with any instructions or visual aids. Another problem faced by the medical practitioner with conventional non-invasive techniques is determining how to assess the oxygenation level of compartments that lie underneath a particular neighboring compartment, such as with the deep posterior compartment of the human leg.

In trauma settings, near infrared sensors often do not work when they are placed over regions of the body that have hematomas or pools of blood. In such conditions, a medical practitioner usually guesses at what regions of the human body do not contain any hematomas that could block compartment measurements. Also, conventional near infrared sensors typically are not sterilized and cannot be used in surgical or operating environments.

Near infrared sensors (NIRS) in their current form are limited to a single sensor with a single sensor depth. They also can be affected by skin pigmentation that is not accounted for in the current technology. Placement of the sensor can be difficult since an expanding hematoma can block a previously acceptable placement. Additionally, the only system as of this writing is a single monitor system. There is no product available at this time which will allow for multiple areas to be monitored in close proximity to one another without the potential for interference from other sensor light sources.

Treatment for Compartment Syndrome

Referring now to FIG. 3, this figure is a side view of a human leg 100 in which a surgical procedure, known as a fasciotomy, was performed in order to release the pressures in one or more compartments surrounding the bones of the leg according to a technique known in the art in order to alleviate a compartment syndrome that was diagnosed. This surgical procedure includes an incision 300 that is made along the length of the leg 100 and is generally as long as the compartments contained within the leg 100. While a single incision 300 is illustrated in FIG. 3, a second incision is made on the opposing side of the leg so that a patient will have two incisions on each side of his leg 100. These incisions typically extend from near the knee to near the ankle on each side of the leg.

This procedure is very invasive and it often leaves the patient with severe scars and venous congestion once healed. Also the procedure increases a patient's chances of receiving an air-borne infection because the incisions made on either side of the leg are usually left open for several days in order to allow for the swelling and excess bleeding to subside. Fasciotomies transform a closed fracture (one in which the skin is intact and minimal risk of infection) to an open fracture. Open fractures have a much higher risk of bone infections which requires multiple surgical debridements and ultimately amputation in some cases in order to appropriately treat. Additionally, some wound cannot be closed and require skin transfers, or skin grafts, from other parts of the body, usually from the anterior thigh.

Therefore, it is quite apparent that accurately diagnosing compartment syndrome is critical because any misdiagnosis can lead to significant morbidity. A missed compartment syndrome can result in an insensate and contracted leg and foot. A fasciotomy which is highly invasive procedure and which exposes a patient to many additional health risks should not be performed in the absence of a compartment syndrome.

Additionally, time is an important factor in the evaluation of these patients. Ischemic muscle begins to undergo irreversible changes after about six hours of decreased perfusion. Once irreversible changes or necrosis occur, a fasciotomy should not be performed. Fasciotomies in the setting of dead muscle only increase the risk for severe infections and other complications. Late fasciotomies have been shown to have approximately a 50-75% risk of complication. Therefore, fasciotomies need to be performed early but judiciously in patients that are often unresponsive or uncooperative in order to prevent severe morbidity.

Accordingly, there is a need in the art for a non-invasive, real time method and system that monitors oxygenation levels of a compartment and that is provided with sensors which can be precisely positioned over a compartment of interest in order to assist in assessing conditions associated with a compartment syndrome. A further need exists in the art for a non-invasive method that monitors oxygenation levels of a compartment over long periods of time at frequent time intervals and that can monitor different compartments that may be in close proximity with one another. Another need exists in the art for oxygenation sensors that can be fabricated to fit the size of compartments of interest. There is also a need in the art for a non-invasive method and system that monitors oxygenation levels and that can identify ideal locations along a human body in which to conduct scans for deep compartments. There is another need in the art for sterile, non-invasive oxygenation sensors that can be used under surgical and operating conditions. There is a need for multiple locations and multiple compartments to be monitored in a continual and orchestrated manner by a single system. In other words, multiple monitors coordinated to limit noise and continually monitor multiple compartments are needed in the art.

SUMMARY OF THE INVENTION

A method and system for monitoring oxygenation levels in compartments of an animal limb, such as in a human leg or a human thigh or a forearm, can be used to assist in the diagnosis of a compartment syndrome. The method and system can include one or more near infrared compartment sensors in which each sensor can be provided with a compartment alignment mechanism and a central scan depth marker so that each sensor may be precisely positioned over a compartment of a living organism, such as a compartment of a human leg or human thigh or forearm. The method and system can include a device for displaying oxygenation levels corresponding to respective compartment sensors that are measuring oxygenation levels of a compartment of interest.

The alignment mechanism of a compartment sensor can include a linear marking on a surface of the compartment sensor that is opposite to the side which produces a light scan used to detect oxygenation levels. The linear marking can be used by a medical practitioner to align a compartment sensor with the longitudinal axis of a compartment.

The central scan depth marker can include a linear marking positioned on a surface of a compartment sensor that intersects the alignment mechanism, a crosshatch, at a location along the alignment mechanism that denotes the deepest region of a light scan produced by the compartment sensor. The depth of measurement can be displayed in numeric form over the crosshatch guide to aid the clinician since depth varies based on light source & receptor separation. The central scan depth marker can insure that a medical practitioner properly aligns the compartment sensor at a location that will measure a compartment of interest.

According to one exemplary embodiment of the invention, in addition to each compartment sensor having a compartment alignment mechanism and a central scan depth marker, the compartment sensors can be grouped in pairs and share a common supporting substrate. The common supporting substrate can include a separation device, such as, but not limited to, a perforated region. The separation device, such as a perforated region, can be torn or broken by the user in order to adjust for a size of a compartment of interest. In other words, with the separation device, a pair of two compartment sensors can be physically divided so that the sensors do not share a common substrate after the separation device is utilized.

According to another exemplary embodiment of the invention, a compartment sensor can include one light emitting device and two different sets of light detectors such that the compartment sensor can provide a first, shallow oxygenation scan at a first depth and a second, deep oxygenation scan at a second depth. The second depth can be greater than the first depth, so that a general computing device coupled to the two compartment sensors can be programmed or hardwired to calculate the second, deep oxygenation level at the second depth by subtracting data generated by the first, shallow oxygenation level at the first depth.

According to another alternate exemplary embodiment of the invention, several individual compartment scanners can be grouped together along a longitudinal axis of a common supporting material to define a linear compartment array. The linear compartment array can also include a linear marking on its surface that is opposite to the side which produces the light scan as well as multiple crosshatches for depth denotation. The linear marking can be used to align the linear compartment array with a longitudinal axis of a compartment.

According to another exemplary embodiment of the invention, a compartment sensor or compartment sensor array can be positioned at a predetermined position along a human leg in order to measure a deep posterior compartment of the human leg. Position is posteromedial to the posterior aspect of the tibia.

According to one exemplary embodiment of the invention, a linear compartment sensor array can include individual sensors that scan at different depths such that the linear compartment sensor array as a whole has a varied scan depth along its longitudinal axis to more closely match the topography, shape, or depth of a compartment of interest that has a corresponding varied depth. According to another exemplary embodiment of the invention, each individual compartment sensor can produce its oxygenation scan at a predetermined interval such that each individual compartment sensor is only activated one at a time or in a predetermined sequence so that any two or more sensors are not working at a same instant of time in order to reduce any potential for light interference among the different oxygenation scans produced by respective sensors of the array.

According to a further exemplary embodiment of the invention, each compartment sensor can use optical filters in combination with different wavelengths of light so that two or more compartment sensors can scan at the same without interfering with one another. According to another exemplary embodiment of the invention, a linear compartment array can include optical transmitters that are shared among pairs of optical receivers. For example, a single optical transmitter can be used with two optical receivers that are disposed at angles of one-hundred eighty degrees relative to each other and the optical transmitter along the axis of the compartment.

According to yet another exemplary embodiment, a compartment sensor or compartment sensor array can be made from materials that can be sterilized and used in operating environments that are free from germs or bacteria. A compartment sensor or compartment sensor array can also be provided with a coating that is sterilazable or sterilized. When a compartment sensor or compartment sensor array is sterilized, it can be provided underneath bandages or dressings adjacent to a wound or injury of a compartment or proximate to compartment of interest. Each sensor can be provided with a common and sufficient length of cord, such as on the order of approximately ten feet, to allow the cord to extend off the sterile operative field.

According to another exemplary embodiment of the invention, the compartment monitoring method and system can include a device that displays oxygenations levels of a compartment over time in which oxygenation levels are measured at a particular time frequency, such as, but not limited to, on the order of seconds or minutes. According to another exemplary embodiment of the invention, the compartment monitoring system and method can display all measured data from all sensors on the same screen. The display can also show a differential between injured and uninjured leg values of the concordant compartments.

For example, the screen can display calculations of the difference between the values of the anterior compartment of both the injured leg and the contralateral uninjured leg (control leg) to help evaluate the perfusion of the injured leg. According to an alternate exemplary embodiment of the invention, the compartment monitoring system and method can display anatomical features and locations for positioning the sensors of the system along compartments of interest selected by a user. This program at initial set up can help insure proper placement of the sensor by the clinician by using diagrams for accurate placement for each of the labeled sensors or sensor arrays.

According to another exemplary embodiment of the invention, the compartment monitoring system can detect changes in a size of a hematoma when at least one linear compartment array is used to measure oxygenations levels at different positions of a compartment. Alternatively, the compartment monitoring system can provide information on various levels of blood flow along the longitudinal axis of a compartment when at least one linear compartment array is used to measure oxygenations levels at different positions of a compartment.

Alternatively, according to another exemplary embodiment of the invention, a compartment sensor can be provided with a skin pigment sensor that has a known reflectance and that can be used to calibrate the compartment sensor based on relative reflectance of skin pigment which can affect data generated from oxygenation scans. For example, a skin narrow-band simple reflectance device, a tristimulus colorimetric device, or scanning reflectance spectrophotometer can be incorporated into the oxygenation sensor system to obtain a standardized value for skin pigmentation which evaluate melanin and hemoglobin in the skin.

Once the skin melanin is determined it can be correlated to its calculated absorption or reflectance (effect) on the NIRS value using a predetermined calibration system. This effect, optical density value, can be incorporated in tissue hemoglobin concentration calculations in the deep tissue. Accounting for skin pigmentation will usually allow for information or values to be compared across different subjects with different skin pigmentation as well as using the number as an absolute value instead of monitoring simple changes in value over time.

According to an exemplary embodiment of the invention, a compartment sensor can be provided with layers of a known thickness and a known absorption in order to reduce the depth of an oxygenation scan by the sensor so that a thin layer of tissue, such as skin can be measured by the sensor. In other words, due to limitations of how close the light source and receptor can be positioned, in order to evaluate very superficial layers such as skin, the sensor can be separated from the skin of the subject by fixed amount with a known material. For example, by using a material with a known optical density, the length of a scan can be shortened by projecting the light pathway mostly through the known material.

The light pathway would escape the known material only at the maximum depth to evaluate a limited depth of tissue such as skin. This technique would allow for direct measurement of the skin pigmentation effects on the system. This skin sensor can be either incorporated into the compartment monitoring system directly or used to construct the predetermined calibration for skin reflectance values that can be used by the compartment monitoring system.

According to another exemplary embodiment of the invention, the compartment monitoring system can receive data from a blood pressure monitoring system in order to correlate oxygenation levels with blood pressure. The compartment monitoring system that includes a blood pressure monitoring system can activate an alarm, such as an audible or visual alarm (or both), when the diastolic pressure of a patient drops since it has been discovered that perfusion can be significantly lowered or stopped at low diastolic pressures and when compartment pressures are greater than the diastolic pressure.

According to another exemplary embodiment, the compartment monitoring system can increase a frequency of data collection for oxygenation levels and/or blood pressure readings when low blood pressure is detected by the system. According to an alternative exemplary embodiment, the compartment monitoring system can display blood pressure and oxygenation levels simultaneously and in a graphical manner over time, such as an X-Y plot in a Cartesian plane or as two separate graphs over time. Correlation between hemoglobin concentration and diastolic pressure can be used to estimate intra-compartmental pressures without having to use invasive needle measurements.

According to another further exemplary embodiment, the inventive system can incorporate oxygenation levels from both lower extremities and compare values between the legs or other body parts. Initial data from patients with extremity injuries by the inventor have shown that muscular skeletal injuries cause hyperemia (increased blood flow and oxygen) in the injured extremity. If a compartment syndrome develops, the oxygenation drops from an elevated state to an equal and then lower level with comparison to the uninjured limb. Therefore when comparing injured and uninjured extremities, the injured limb may show increased oxygenation levels. If levels begin to drop in the injured limb compared to the uninjured limb, an alarm or alert can be triggered to alert the clinician. A display for the blood pressure being measured can also be provided by the system.

BRIEF DESCRIPTION OF THE DRAWINGS

FIG. 1 illustrates an X-ray view of a human leg with fractured bones of the tibia and fibula that lead to one or more compartment syndromes in muscles surrounding the bones of the human leg.

FIG. 2 is a side view of a human leg in which compartment pressures are being measured with a large bore needle according to a conventional method known in the prior art.

FIG. 3 is a side view of a human leg in which a surgical procedure, known as a fasciotomy, was performed in order to release the pressures in one or more compartments surrounding the bones of the leg according to a technique known in the art.

FIG. 6B, this figure illustrates the compartment sensor of FIG. 6A that can scan at two or more depths in order to measure deeper compartments of an animal body according to one exemplary embodiment of the invention.

FIG. 7 illustrates a near light detector and a far light detector that are positioned within substrate material at predetermined distances from the optical transmitter of a compartment sensor according to one exemplary embodiment of the invention.

FIG. 8A illustrates a linear array of compartment sensors assembled as a single mechanical unit that can provide scans at various depths according to one exemplary embodiment of the invention.

FIG. 13A illustrates various locations for single compartment sensors that can be positioned on a front side of animal body, such as a human, to measure oxygenation levels of various compartments according to one exemplary embodiment of the invention.

FIG. 14B illustrates various locations for compartment sensor arrays that can be positioned over compartments on a rear side of an animal body, such as a human, to measure oxygenations levels of the various compartments according to one exemplary embodiment of the invention.

FIG. 25 is a logic flow diagram illustrating an exemplary method for monitoring oxygenation levels of a compartment for detecting conditions of a compartment syndrome.

DETAILED DESCRIPTION OF EXEMPLARY EMBODIMENTS

A method and system for monitoring oxygenation levels in compartments of an animal limb, such as in a human leg or a human thigh or a forearm, can be used to assist in the diagnosis of a compartment syndrome. The method and system can include one or more near infrared compartment sensors in which each sensor can be provided with a compartment alignment mechanism and a central scan depth marker so that each sensor may be precisely positioned over a compartment of a human leg or human thigh or forearm. The method and system can include a device for displaying oxygenation levels corresponding to respective compartment sensors that are measuring oxygenation levels of a compartment of interest.

Figure 4:
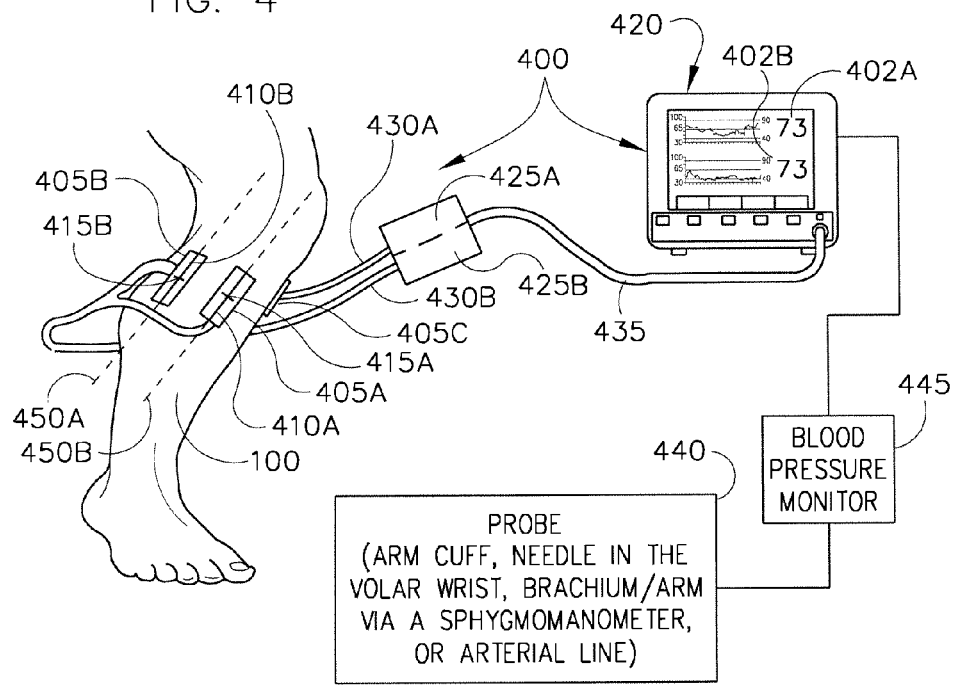
FIG. 4 illustrates oxygen levels of compartments of a human leg being measured by compartment sensors that include compartment alignment mechanisms and central scan depth markers according to one exemplary embodiment of the invention.

Referring now to the drawings, in which like reference numerals designate like elements, FIG. 4 illustrates oxygen levels 402A, 402B of compartments of a human leg 100 being measured by a near-infrared spectroscopy (NIRS) sensors 405A, 405B that include a compartment alignment mechanisms 410A, 410B and central scan depth markers 415A, 415B according to one exemplary embodiment of the invention.

The alignment mechanism 410 of a compartment sensor 405 can include a linear marking on a surface of the compartment sensor 405 that is opposite to the side which produces a light scan used to detect oxygenation levels. The linear marking can be used by a medical practitioner to align a compartment sensor 405 with the longitudinal axis 450 of a compartment of interest. The invention is not limited to a solid line on the sensor 405. Other alignment mechanisms 410 within the scope of the invention include, but are not limited to, tick marks, dashed lines, notches cut in the substrate of the compartment sensor 405 to provide a geometric reference for the medical practitioner, and other like visual orienting alignment mechanisms 405.

The central scan depth marker 415 can include a linear marking positioned on a surface of a compartment sensor 405 that intersects the alignment mechanism 410 at a location along the alignment mechanism 410 that denotes the deepest region of a light scan produced by the compartment sensor 405. The depth of measurement can be displayed in numeric form over the central scan depth marker 415 as a guide to aid medical practitioner since scan depth can vary based on the compartment sensor's light source and receptor separation. The central scan depth marker 415 can insure that a medical practitioner properly aligns the compartment sensor 405 at a location that will measure a compartment of interest. Similar to the alignment mechanism 410 noted above, the invention is not limited to a solid line on the compartment sensor 405. Other central scan depth markers 415 within the scope of the invention include, but are not limited to, tick marks, dashed lines, notches cut in the substrate of the compartment sensor to provide a geometric reference for the medical practitioner, and other like visual orienting central depth markers 415.

Once the proper position for a compartment sensor 405 is determined by the medical practitioner with the compartment alignment mechanism 410 and the central scan depth marker 415, the medical practitioner can apply the compartment sensor 405 on the patient by using an adhesive that is already part of the compartment sensor 405.

FIG. 4 illustrates three compartment sensors 405A, 405B, and 405C of a system 400 for monitoring three different compartments of the lower human leg 100. A fourth compartment sensor 405D not illustrated can be positioned on a side of the leg not illustrated and which monitors the fourth compartment of the lower human leg 100. The compartment sensors 405 illustrated in FIG. 4 and discussed throughout this document can be of the type described in U.S. Pat. No. 6,615,065 issued in the name of Barrett et al. (the "'065 patent"), the entire contents of which are hereby incorporated by reference. The compartment sensors 405 can include those made and distributed by Somanetics, Troy, Mich. However, other conventional near infrared compartment sensors 405 can be used without departing from the scope and spirit of the invention.

The compartment sensors 405 can generally provide spectrophotometric in vivo monitoring of blood metabolites such as hemoglobin oxygen concentration in any type of compartment and on a continuing and substantially instantaneous basis.

The compartment sensors 405 are coupled to a processor and display unit 420 which displays the two oxygen levels 402A, 402B comprising the values of seventy-three. The processor and display unit 420 can display all four oxygen levels of four compartments of the human leg 100 when at least four compartment sensors 405 are deployed. The invention is not limited to four compartment sensor embodiments. The invention can include any number of compartment sensors for the accurate detection of conditions that may be associated with compartment syndrome. For example, another exemplary embodiment illustrated in FIG. 14C allows for eight sensor readings so that concomitant monitoring of the contralateral uninjured leg can be performed.

The processor of the display unit 420 can be a conventional central processing unit (CPU) known to one of ordinary skill in the art. It may have other components too, similar to those found in a general purpose computer, such as, but not limited to, memory like RAM, ROM, EEPROM, Programming Logic Units (PLUs), firmware, and the like. Alternatively, the processor and display unit 420 can be a general purpose computer without departing from the invention.

The processor and display unit 420 can operate in a networked computer environment using logical connections to one or more other remote computers. The computers described herein may be personal computers, such as hand-held computers, a server, a client such as web browser, a router, a network PC, a peer device, or a common network node. The logical connections depicted in the Figures can include additional local area networks (LANs) and a wide area networks (WANs) not shown.

The processor and display unit 420 illustrated in FIG. 4 and the remaining Figures may be coupled to a LAN through a network interface or adaptor. When used in a WAN network environment, the computers may typically include a modem or other means for establishing direct communication lines over the WAN.

In a networked environment, program modules may be stored in remote memory storage devices. It will be appreciated that the network connections shown are exemplary and other means of establishing a communications link between computers other than depicted may be used.

Moreover, those skilled in the art will appreciate that the present invention may be implemented in other computer system configurations, including other hand-held devices besides hand-held computers, multiprocessor systems, microprocessor based or programmable consumer electronics, networked personal computers, minicomputers, mainframe computers, and the like.

The invention may be practiced in a distributed computing environment where tasks may be performed by remote processing devices that are linked through a communications network. In a distributed computing environment, program modules may be located in both local and remote storage devices.

The processor and display unit 420 can comprise any general purpose computer capable of running software applications and that is portable for mobile applications or emergency applications.

The communications between the processor and display unit 420 and the sensors 405 can be wire or wireless, depending upon the application. Typical wireless links include a radio frequency type in which the processor and display unit 420 can communicate with other devices using radio frequency (RF) electromagnetic waves. Other wireless links that are not beyond the scope of the invention can include, but are not limited to, magnetic, optical, acoustic, and other similar wireless types of links.

In the exemplary embodiment illustrated in FIG. 4, the compartment sensors 405 are coupled to the processor and display unit 420 with cables 430A, 430B which can include electrical conductors for providing operating power to the light sources of the compartment sensors 405 and for carrying output signals from the detectors of the sensors 405 to the display unit 420. The cables 430 may be coupled to a quad-channel coupler, a preamplifier 425A, 425B, and an integrated, multiple conductor cable 435. Alternatively, all wires could be packaged or merged into a single unit or cord or plug (not illustrated) for insertion into the monitor for ease of management for the clinician and to prevent misplacement of wire plugs into wrong sockets.

In addition to tracking compartment oxygen levels, the processor and display unit 420 may receive data from a blood pressure monitor 445. The blood pressure monitor 445 may be coupled to a probe 440 that takes pressure readings from the patient at one or more locations, such as, but not limited to, an arm with a cuff, a needle in the volar wrist, the brachium (arm) via a sphygmomanometer, or arterial line. The probe 440 can be any one of a number of devices that can take blood pressure readings, such as, but not limited to, automated inflating pressure cuffs (sphygmomanometer), arterial lines, and the like. Similarly, other types of blood pressure monitors 445 are not beyond the scope of the invention. Further details of the relationship between blood pressure and oxygen levels in the human body will be discussed and described more fully below in connection with FIGS. 19-20.

The display and processing unit 420 can display values at any one time for all compartment sensors 405 being used. While the display and processing unit 420 only displays two oxygen levels for the embodiment illustrated in FIG. 4, the display and processing unit 420 could easily display all four values from the four compartment sensors 405 that are being used to monitor the four compartments of the lower leg 100.

Figure 5A:
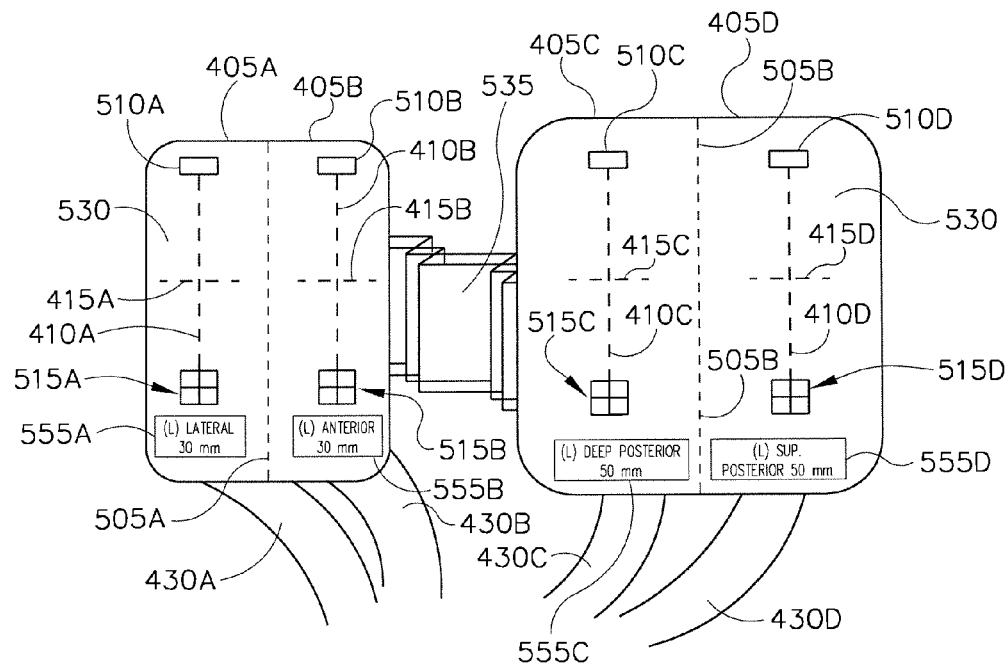
FIG. 5A illustrates a bottom view of two pairs of compartment sensors with each sensor having a compartment alignment mechanism and a central scan marker in addition to a separating device according to one exemplary embodiment of the invention.

Referring now to FIG. 5A, this figure illustrates a bottom view of two pairs of compartment sensors 405 with each sensor 405 having a compartment alignment mechanism 410 and a central scan marker 415 in addition to a separating device 505 according to one exemplary embodiment of the invention. The substrate 530 of each compartment sensor 405 can comprise a foam or plastic material that may have a soft and comfortable outer layer. The separating device 505 is illustrated with a dashed line in FIG. 5A.

According to one exemplary embodiment the separating device 505 can comprise a perforation in the substrate 530. A perforation is a series of cuts or removed portions positioned along a line which can be perforated or separated. This means, for the exemplary embodiment illustrated in FIG. 5A, the first compartment sensor 405A can be physically separated from the second compartment sensor 405B. The separating device 505 is not limited to perforations and it can include other types of devices. For example, the separating device 505 can comprise a zipper, a plastic seal line, hook and loop fasteners and other like devices that would permit the rapid and accurate expansion of compartment sensors 405 when used in a trauma setting.

As noted above, the compartment sensors 405 can include alignment mechanisms 410 and a central scan depth marker 415 in order to accurately position the compartment sensors 405 over compartments of interest. The alignment mechanisms 410 and central depth markers 415 are illustrated with dashed or dotted lines because they are "hidden" relative to the bottom view of the compartment sensors 405 which are illustrated in FIG. 5A.

Each compartment sensor 405 may comprise an optical transmitter 510 and an optical receiver 515. The optical transmitter 510 may comprise an electrically actuated light source for emitting a selected examination spectra. Specifically, the optical transmitter 510 may comprise two or more narrow-bandwidth LEDs whose center output wavelengths correspond to the selected examination spectra. Each optical receiver 515 may comprise two or more light detectors, such as photodiodes. In the embodiment illustrated in FIG. 5A, the optical receiver 515 has a total of four photodiodes in which pairs of photodiodes work together to provide a "near" detector and a "far" detector. Each photo diode must have two receptors to receive light at two separate wavelengths to allow for calculations of oxy-hemoglobin and deoxy-hemoglobin concentrations. Using two pairs of receptors allows for a deep and shallow set to enable isolation of only the deep tissue oxygenation (see FIG. 7).

Referring briefly now to FIG. 7, the "near" light detector 702B and the "far" light detector 702A are positioned within the substrate material 530 at predetermined distances from the optical transmitter 510. The "near" detector 702B formed by the two photodiodes that are closest to the optical transmitter 510 have a light mean path length 710B which is primarily confined to "shallow" layers 705 of a compartment of interest. Meanwhile, the "far" detector 702A formed by the pair of photodiodes that are farthest from the optical transmitter 510 have a light mean path 710A that is longer than that of the "near" detector and is primarily confined to "deep" layers of a compartment of interest in a leg 100.

By appropriately differentiating the information from the "near" or "shallow" detector 702B (which may produce a first data set) from the "far" or "deep" detector 702A (which may produce a second data set), a resultant value for the tissue optical density may be obtained that characterizes the conditions within a compartment of interest without the effects that are attributable to the overlying tissue 705 which is adjacent to the compartment of interest.

This enables the compartment monitoring system 400 (illustrated in FIG. 4) to obtain metabolic information on a selective basis for particular regions within the patient and by spectral analysis of the metabolic information and by using appropriate extinction coefficients, a numerical value or relative quantified value such as 402 of FIG. 4 may be obtained which can characterize metabolites or other metabolite data, such as the hemoglobin oxygen saturation, within the particular region of interest. This region of interest is defined by the curved light mean path 710A extending from the optical transmitter 510 to the "far" or "deep" detector 702A and between this path 710A and the outer periphery of the patient but excluding the region or zone defined by the curved light mean path 710B extending from the optical transmitter 510 to the "near" or "shallow" detector 26. Further details of the compartment sensors 405 are described in U.S. Pat. No. 6,615,065, issued in the name of Barrett et al., which is hereby incorporated by reference.

Referring back now to FIG. 5A, each compartment sensor 405 has its own cable 430 that provides power to the optical transmitter 405A and that receives data from the optical receiver 515. Each compartment sensor 405 may also include a label 555 which may comprise a name and an anatomical location to position the compartment sensor 405 on a patient. This label may be placed on the bottom of the sensor 405 that contacts the patient as well as on the side that is opposite to the side which contacts the patient. For example, the first sensor 405A can have a first label 555A that comprises the phrase, "Lateral" to describe the name of the compartment that this compartment sensor 405A that is designed to assess. The numerical depth can also be displayed on the label, but is not limited to a single depth.

The first pair of compartment sensors 405A, 405B may be coupled to the second pair of compartment sensors 405C, 405D with an expansion device 535. The expansion device 535 may comprise an elastic material that stretches. The expansion device 535 allows the pair of compartment sensors 405 to be positioned on appropriate parts of a patient to monitor any compartments of interest. The four compartment sensor exemplary embodiment illustrated in FIG. 5A is designed for the four compartments of a human lower leg 100.

The expansion device 535 is not limited to elastic material. The expansion device can include other mechanisms which allow for an adjustable separation between the pairs of compartment sensors 405 so that the compartment sensors 405 may be precisely and appropriately positioned over specific compartments of interest. The expansion device 535 may include, but is not limited to, springs, tape, hook and loop fasteners, gauze, and other like materials.

Figure 5B:
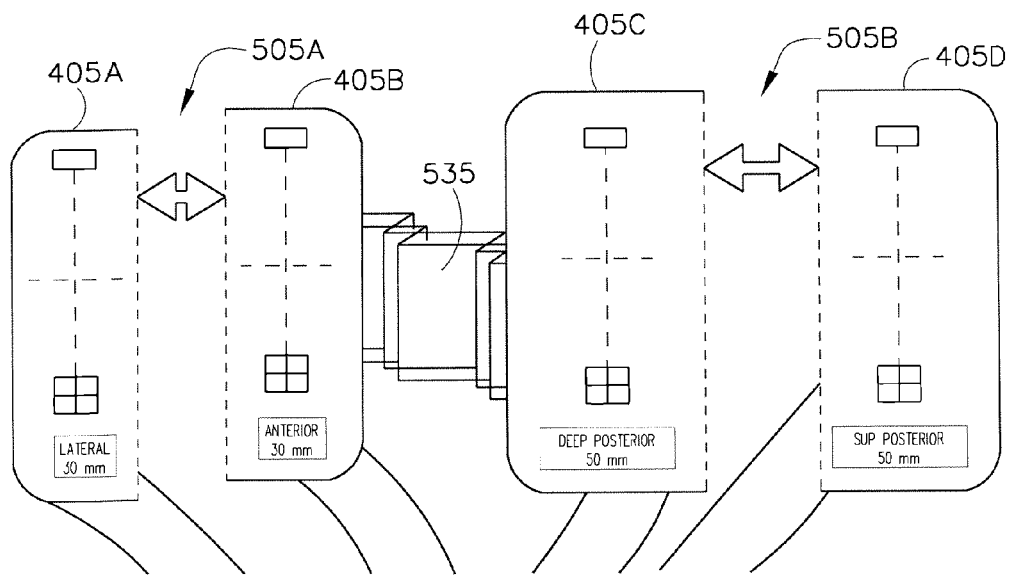
FIG. 5B illustrates a bottom view of the four compartment sensors of FIG. 5A (?) but with the individual sensors divided from one another through using the separating device, such as the perforations, according to one exemplary embodiment of the invention.

Referring now to FIG. 5B, this figure illustrates a bottom view of the four compartment sensors 405 of FIG. 5A but with the individual sensors 405 divided from one another through using the separating device 505, such as the perforations, according to one exemplary embodiment of the invention. Specifically, the first compartment sensor 405A of the first pair of sensors 405A, 405B is physically located away from the second compartment sensor 405B. Similarly, the third compartment sensor 405C of the second pair of sensors 405B, 405C is physically located away from the fourth compartment sensor 405C. The separating device 505, the expansion device 535 in combination with the alignment mechanism 410 and central scan depth marker 415 can allow the compartment sensors 405 to be accurately and precisely positioned over compartments of interest, such as the four compartments of a human leg 100. In order to accurately monitor the appropriate compartment, a right and left configuration can be provided since compartment alignment would be reversed based on which leg is examined by the medical practitioner. Each configuration would be labeled as right or left. The configuration illustrated in FIGS. 5A and 5B are designed for human left leg 100 where the expansion device would be positioned over the tibia.

Figure 6A:
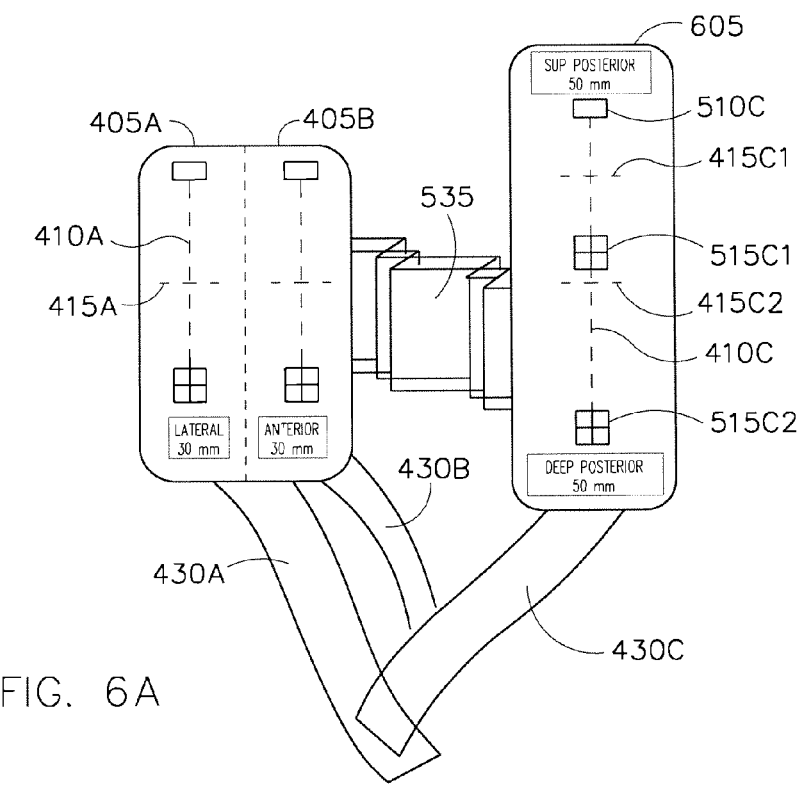
FIG. 6A illustrates a bottom view of a three sensor embodiment in which one sensor of the three compartment sensors can scan at two or more depths according to one exemplary embodiment of the invention.

Referring now to FIG. 6A, this figure illustrates a bottom view of a three sensor embodiment in which one sensor 605 of the three compartment sensors 405A, 405B, 605 can scan at two or more depths according to one exemplary embodiment of the invention. Specifically, a compartment sensor 605 may include an optical transmitter 510C that works with at least two different optical receivers 515C1 and 515C2. As noted above, each optical receiver 515 may comprise two or more light detectors, such as photodiodes. In the embodiment illustrated in FIG. 6A, each optical receiver 515C1 and 515C2 has a total of four photodiodes in which pairs of photodiodes work together to provide "near" detector and "far" detectors for a respective receiver 515C1, 515C2. This combination allows the compartment sensor 605 to scan at least two different depths. And because of the capability to scan at two different depths, the compartment sensor 605 is provided with two different central scan depth markers 415C1, 415C2.

Referring now to FIG. 6B, this figure illustrates the compartment sensor 605 of FIG. 6A that can scan at two or more depths in order to measure deeper compartments of an animal body according to one exemplary embodiment of the invention. The two optical receivers 515 of FIG. 6B work in principal in an identical manner relative to the optical receiver described in connection with FIG. 7 discussed above. This means that the combination of the optical transmitter 510C and optical receiver 515C1 can provide an oxygenation level for a first scan depth 620B of a patient. Meanwhile, the combination of the optical transmitter 510C and the optical receiver 515C2 can provide an oxygenation level for a second scan depth 620A of a patient.

Therefore, this stacked compartment sensor 605 can be used to measure the oxygenation level of a first compartment that may be positioned underneath a second compartment, such as for the deep posterior compartment of a lower leg 100 of a human body which is positioned beneath the superficial posterior compartment of the leg 100. This stacked compartment sensor 605 can allow the display and processing unit 420 to subtract the oxygenation level found at the first scan depth 620B of the first compartment, such as the superficial posterior compartment, from the oxygenation level at the second scan depth 620A of the second compartment, such as the deep posterior compartment.

The invention is not limited to the two stacked optical receiver embodiment 605 illustrated FIGS. 6A and 6B, and can include any number of optical receivers 515 positioned in the substrate material 530 so that various scan depths can be made to determine oxygenation levels within multiple compartments that may be stacked on or positioned adjacent to one another in a sequential or layered, shallow to deep arrangement.

Referring now to FIG. 8A, this Figure illustrates a linear array 805 of compartment sensors 405 assembled as a single mechanical unit that can provide scans at various depths 620A, 620B, 620C, and 620D. The compartment sensors 405 can be simultaneously activated to produce their scans of various depths 620 at the same time when optical filters are used as will be described more fully below in connection with FIG. 8C. Alternatively, the sensors 405 of the linear array 805 can produce their scans of various depths 620 by controlling a phase or timing of the activation of the sensors 405 so that no two sensors 405 are activated at the same time in order to reduce any potential of optical interference between the sensors 405. This phasing of the sensors can be controlled by the display and control unit 420 of FIG. 4.

The first compartment sensor 405A can provide a first scan depth 620A that is shorter or more shallow than a second scan depth 620B produced by the second compartment sensor 405B. The scan depths 620 can increase in this manner along its longitudinal axis which corresponds with its alignment mechanism 410 so that the linear array 805 matches the one or more depths of a single compartment of interest. As noted above in connection with FIG. 6B, the scan depth 620 of a compartment sensor 405 is function of the separation distance between the optical transmitter 510 and optical receiver 515. For example, a scan depth 620 of a compartment sensor 405 can be decreased as the optical receiver 515 is moved closer along the body of the sensor 405 towards the optical transmitter 510C.

One of ordinary skill in the art recognizes that many of the compartments of the human body have various different geometries and resulting depths relative to the outside skin of a patient. For example, the compartments of the lower human leg 100 tend to have a greater depth or volume adjacent to the knee and generally taper or decrease in depth towards the ankle or foot. Therefore, linear arrays 805 of compartment sensors 405 can be designed to have depths that match a particular geometry of a compartment of interest. To achieve these different scan depths 620, each compartment sensor 405 can have an optical transmitter 510 and an optical receiver 515 that is spaced or separated from each other by an appropriate distance to achieve the desired scan depth 620. If a compartment of interest has a substantially "flat" or "linear" depth relative to the skin surface of a patient, the linear array 805 can be designed such that each compartment sensor 405 produces scans with uniform depths (not illustrated) to match a compartment with such a linear or flat geometry.

Like the single sensor embodiments described above in FIGS. 4-6A which are designed to measure individual compartments, the compartment sensor array 805 may comprise an alignment mechanism 410 that can be positioned so that it corresponds with the longitudinal axis 450 of a particular compartment. The compartment sensor array 805 of FIG. 8A is not provided with any central depth markers 415 like those of the single sensor embodiments since the depth markers 415 may not be needed by the medical practitioner since he or she will be assessing the entire length of a particular compartment with the entire compartment sensor array 805 which is unlike that of the single sensor embodiments. Alternatively, multiple crosshatches and numerical depths (not illustrated) can be positioned over each light source/receptor set to locate where each measurement is obtained for identifying sites of a hematoma, which will be described in more detail in connection with FIGS. 15-16 below. Additionally, these positions could be used to locate appropriate amputation level for diabetics or peripheral vascular disease, which is also described in more detail in connection with FIGS. 15-16 below.

Figure 8B:
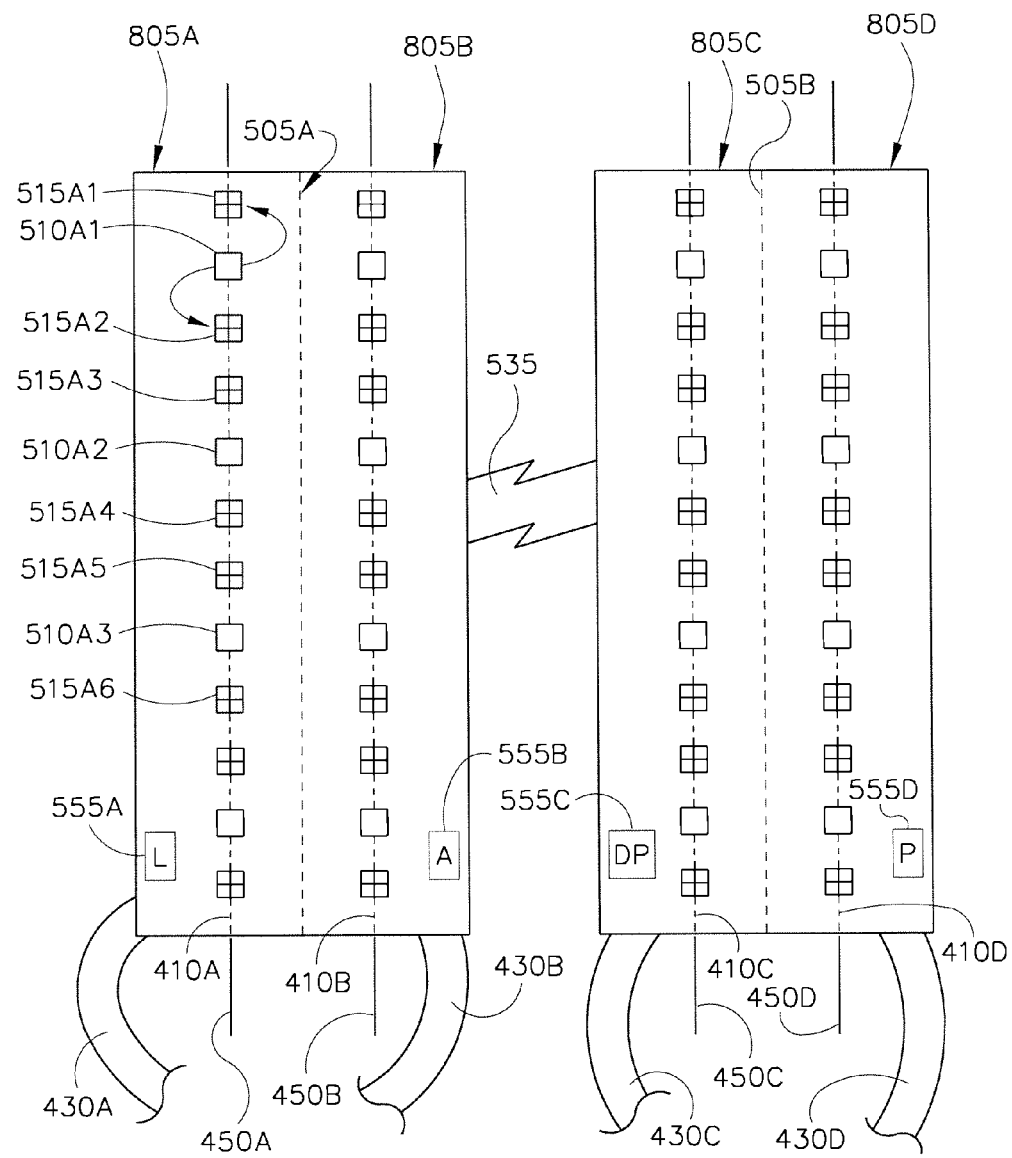
FIG. 8B illustrates a linear compartment sensor array that can include optical transmitters that are shared among pairs of optical receivers according to one exemplary embodiment of the invention.

Referring now to FIG. 8B, this figure illustrates a linear compartment sensor array 805 that can include optical transmitters 510 that are shared among pairs of light receptors 515.

For example, a single optical transmitter 510A1 can produce light rays 820A, 820B that can be used by two optical receivers 515A1, 515A2 that are disposed at angles of one-hundred eighty degrees relative to each other and the optical transmitter 510A1 along the longitudinal axis and alignment mechanism 410A of the compartment sensor array 805A. As described previously, the light source and receptor separation can be varied to best match the topography of the compartment in the leg or other body part. Larger separation would allow for deeper sampling in the proximal leg versus more shallow depth closer to the ankle.

As discussed above in connection with the single sensor array 805 of FIG. 8A, the sensors 405 of each compartment sensor array 805 illustrated in FIG. 8B can be simultaneously activated to produce their scans at the same time when optical filters (not illustrated in FIG. 8B) are used as will be described more fully below in connection with FIG. 8C. Alternatively, the sensors 405 of each linear compartment sensor array 805 can produce their scans by controlling a phase or timing of the activation of the sensors 405 so that no two sensors 405 are activated at the same time in order to reduce any potential for optical interference between the sensors 405. This phasing of the sensors can be controlled by the display and control unit 420 of FIG. 4.

Like the single sensor embodiment illustrated in FIG. 5A, the compartment sensor array 805 of FIG. 8B can comprise an alignment mechanism 410 for aligning the structure with the longitudinal axis 450 of a compartment as well as a separation device 505A that can be used to divide the physical structure of the paired array 805A, 805B into two separate linear compartment sensor arrays 805A, 805B. The compartment sensor arrays 805 of FIG. 8B may also include labels 555 and an expansion device 535, like those of FIG. 5A. The labels can be positioned on the front and back sides of each compartment sensor array 805. While the optical transmitters 510 and receivers 515 of FIG. 8B are illustrated in functional block form, it is noted that these elements as well as other numbered elements, which correspond to the numbered elements of FIGS. 4-7, work similar to the embodiments described and illustrated in FIGS. 4-7.

Figure 8C:
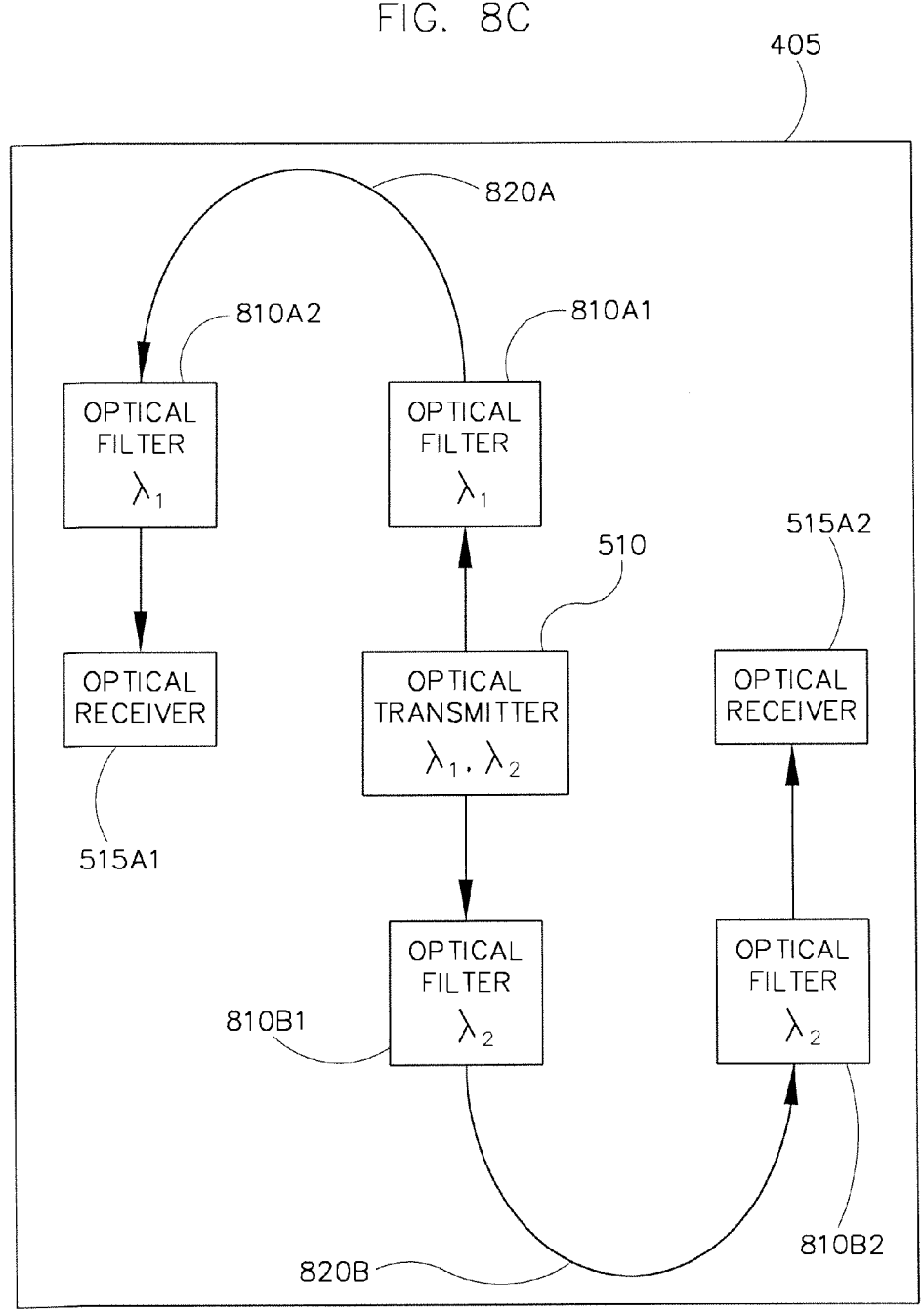
FIG. 8C is a functional block diagram of compartment sensor that illustrates multiple optical receivers that may positioned on opposite sides of a single optical transmitter and that may be simultaneously activated to produce their scans at the same time according to one exemplary embodiment of the invention.

Referring now to FIG. 8C, this figure is a functional block diagram of compartment sensor 405 that illustrates multiple optical receivers 515 that may positioned on opposite sides of a single optical transmitter 510 and that may be simultaneously activated to produce their scans at the same time. This exemplary embodiment can produce scans at the same time by using light with different wavelengths. Using light with different wavelengths can help reduce and substantially eliminate any optical interference that can occur between multiple light rays that may be received by the multiple optical receivers 515. While the optical receivers 515 of FIG. 8C are illustrated in functional block form, it is noted that these receivers 515 as well as other numbered elements, which correspond to the elements of FIGS. 4-7, work similar to the embodiments described and illustrated in FIGS. 4-7.

The two optical receivers 515A1, 515A2 of FIG. 8C may be simultaneously activated when two optical filters 810A, 810B having different wavelengths are used. The first optical filter 810A may have a first wavelength of lambda-one (.lamda.1) which is different than a second wavelength of lambda-two (.lamda.2) that is the wavelength of the second optical filter 810B1. The optical transmitter 510 can be designed to produce light having wavelengths of the first and second wavelengths which correspond with the first and second optical filters 810A, 810B.

Light 820A with a first wavelength can be produced by the optical transmitter 510 propagating its light through a first optical filter 810A1 that is designed to only let the first wavelength pass through it. Similarly, Light 820B with a second wavelength can be produced by the optical transmitter 510 propagating its light through a second optical filter 810B1 that is designed to only let the second wavelength pass through it. A third optical filter 810A2 corresponding with the first optical filter 810A1 can be designed to only pass the first wavelength such that the optical receiver 515A1 only detects light of the first wavelength. Similarly, a fourth optical filter 810B2 corresponding with the second optical filter 810B1 can be designed to only pass the second wavelength such that the optical receiver 515A2 only detects light of the second wavelength.

In this way, simultaneous different compartment scans can be produced at the same time with light having the first wavelength of lambda-one (.lamda.1) and light having the second wavelength of lambda-two (.lamda.2), in which the two optical receivers 515A1 and 515A2 share the same optical transmitter 510. This principal of optical receivers 515 sharing the same optical transmitter 510 is also illustrated in FIG. 8B which provides the compartment sensor arrays 805 discussed above. Specifically, any optical transmitter 510/ optical receiver 515 group that is positioned along a single alignment mechanism 410 and longitudinal axis 450 can be designed to have a unique wavelength relative to its neighbors along the same line. So this means that each optical transmitter 510/optical receiver 515 group of a particular compartment sensor array 805, such as first array 805A, can be designed to have unique wavelengths relative to each other for illuminating the same compartment. Meanwhile, a neighboring compartment sensor array 805, such as second array 805B, may have the same wavelength arrangement as the first array 805A.

One of ordinary skill in the art recognizes that each light optical transmitter and optical receiver design uses two separate wave lengths to solve for oxy-hemoglobin and deoxy-hemoglobin concentrations, as illustrated in FIG. 7. Therefore, the two optical wavelength design described for FIG. 8C above may translate into four or more wavelengths for each optical transmitter 510 and pair of optical receivers 515. The two wavelength design for FIG. 8C was described above for simplicity and to illustrate how groups of optical transmitters and optical receivers can operate at different wavelengths relative to the groupings.

The invention is not limited to only two optical receivers 515 that share the same optical transmitter 510. The invention could include embodiments where a single optical transmitter 510 is shared by a plurality of optical receivers 515 greater than two relative to the exemplary embodiment illustrated in FIG. 8C.

Figure 9A:
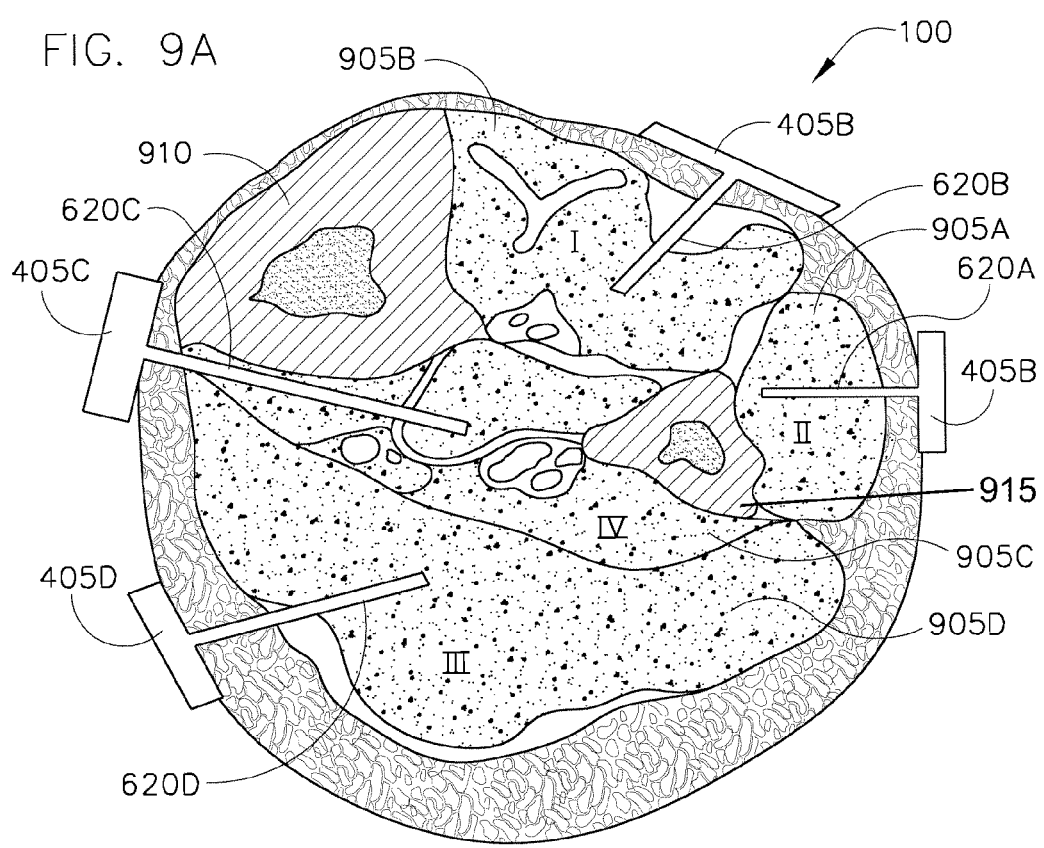
FIG. 9A illustrates a cross-sectional view of a left-sided human leg that has the four major compartments which can be measured by the compartment sensors according to one exemplary embodiment of the invention.

Referring now to FIG. 9A, this figure illustrates a cross-sectional view of a left-sided human leg 100 that has the four major compartments 905 which can be measured by the compartment sensors 405 according to one exemplary embodiment of the invention. A first compartment 905B (also noted with a Roman Numeral One) of the lower human leg 100 comprises the anterior compartment that is adjacent to the Tibia 910 and Fibula 915. A first compartment sensor 405B is positioned adjacent to the anterior compartment 905B and provides a first oxygenation scan having a depth of 620B.

A second compartment 905A (also noted with a Roman Numeral Two) of the lower human leg 100 comprises the lateral compartment that is adjacent to the Fibula 915. A second compartment sensor 405A is positioned adjacent to the lateral compartment 905A and provides a second oxygenation scan having a depth of 620A.

A third compartment 905D (also noted with a Roman Numeral Three) of the lower human leg 100 comprises the superficial posterior compartment that is behind the Tibia 910 and Fibula 915. A third compartment sensor 405D is positioned adjacent to the posterior compartment 905D and provides a third oxygenation scan having a depth of 620D.

A fourth compartment 905C (also noted with a Roman Numeral Four) of the lower human leg 100 comprises the deep posterior compartment that is within a central region of the human leg 100. A fourth compartment sensor 405C is positioned adjacent to the deep posterior compartment 905C and provides a fourth oxygenation scan having a depth of 620C.

Figure 9B:
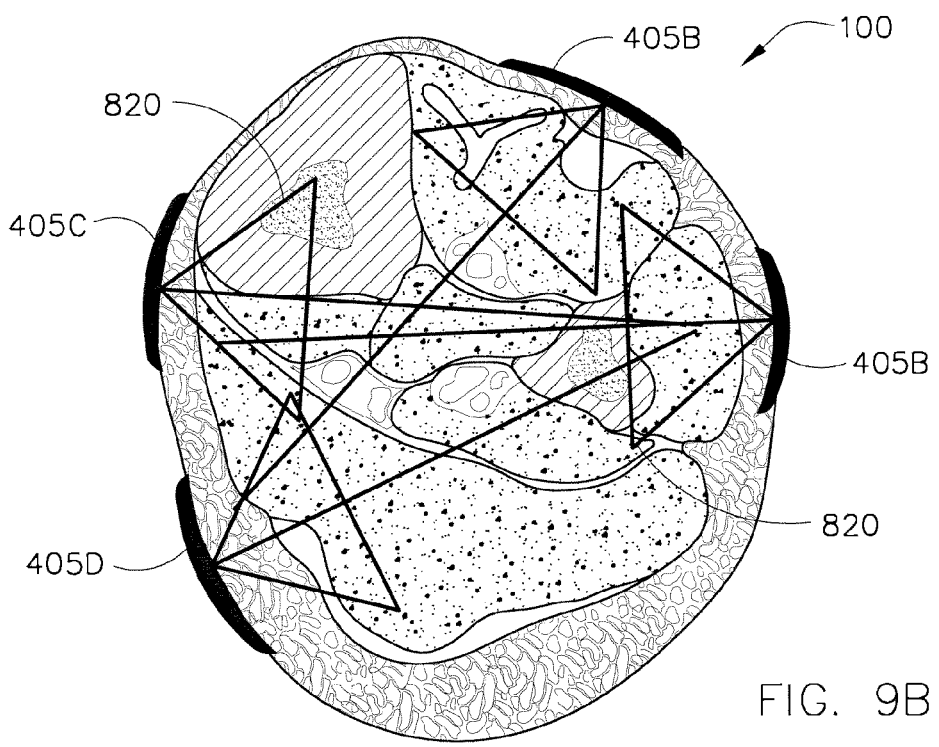
FIG. 9B illustrates a cross-sectional view of a right-sided human leg and possible interference between light rays of simultaneous oxygenation scans made by the compartment sensors into respective compartments of interest according to one exemplary embodiment of the invention.

Referring now to FIG. 9B, this figure illustrates a cross-sectional view of a right-sided human leg 100 and possible interference between light rays 820 of simultaneous oxygenation scans made by the compartment sensors 405 into respective compartments of interest according to one exemplary embodiment of the invention. This figure illustrates how light rays 820 produced by respective compartment sensors 405 can interfere with one another. To resolve this potential problem, the activation and hence, production of light rays 820, by the compartment sensors 405 can be phased so that light rays 820 produced by one compartment sensor 405A are not received and processed by a neighboring compartment sensor 405B, 405C. When light is emitted from the compartment sensors 405 through tissue, the light does not travel in a straight line. It is reflected and spreads throughout the whole tissue. Therefore, light interference or noise would be a significant concern for multiple light sources placed in close proximity to each other. Alternatively, and as noted above, each compartment sensor 405 can produce optical wavelengths that are independent of one another in order to reduce any chances of optical interference.

Figure 9C:
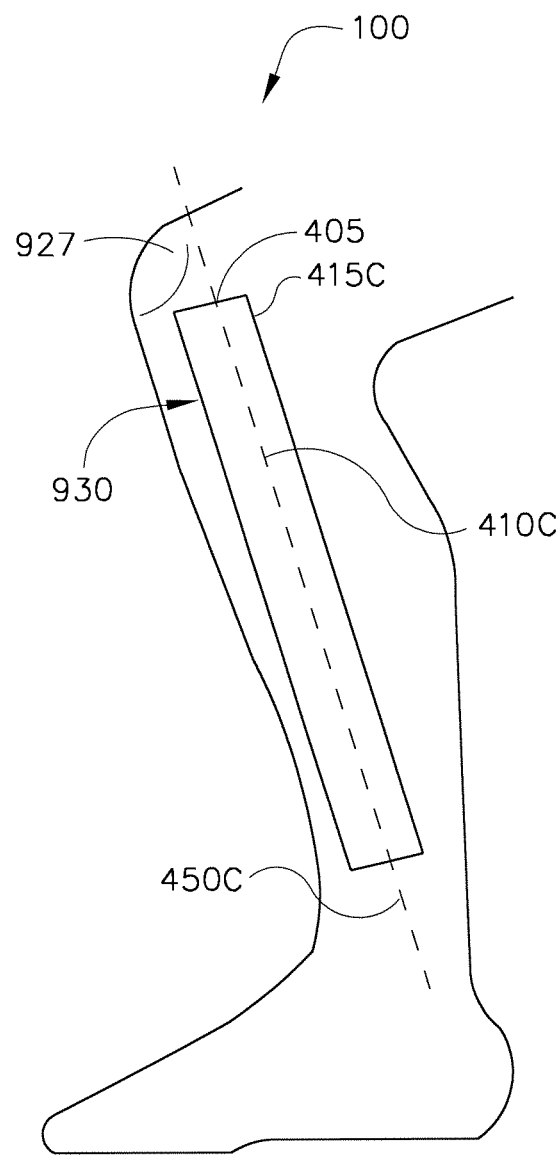
FIG. 9C illustrates a position of a compartment sensor in relation to the knee for the deep posterior compartment of a right sided human leg according to one exemplary embodiment of the invention.

Referring now to FIG. 9C, this figure illustrates a position 930 of a compartment sensor 405C in relation to the knee 927 for the deep posterior compartment 905C of a right sided human leg 100 according to one exemplary embodiment of the invention. As illustrated in FIGS. 9A and 9B discussed above, the deep posterior compartment sensor 405C can be positioned such that the sensor 405C can directly sense the oxygenation levels of this compartment 905C without penetrating or going through another compartment. With respect to FIG. 9C, the deep posterior compartment 905C can be accessed by placing the sensor along the posteromedial aspect of the medial tibia. In other words, palpation of the shin bone will allow the location of the tibia. The sensor 405 should be placed just behind the bone on the inside of the leg along the longitudinal axis 450C of the compartment 905C (not illustrated in this Figure). The compartment sensor 405C can be aligned with the longitudinal axis 450C of the deep posterior compartment 905C through using the alignment mechanism 410C. The compartment sensor 405C can positioned at any point along the longitudinal axis 450C. The location of this deep posterior compartment sensor 405C on the lower leg 100 may be one inventive aspect of the technology since it allows a direct scan of the deep posterior compartment 905C.

Figure 10:
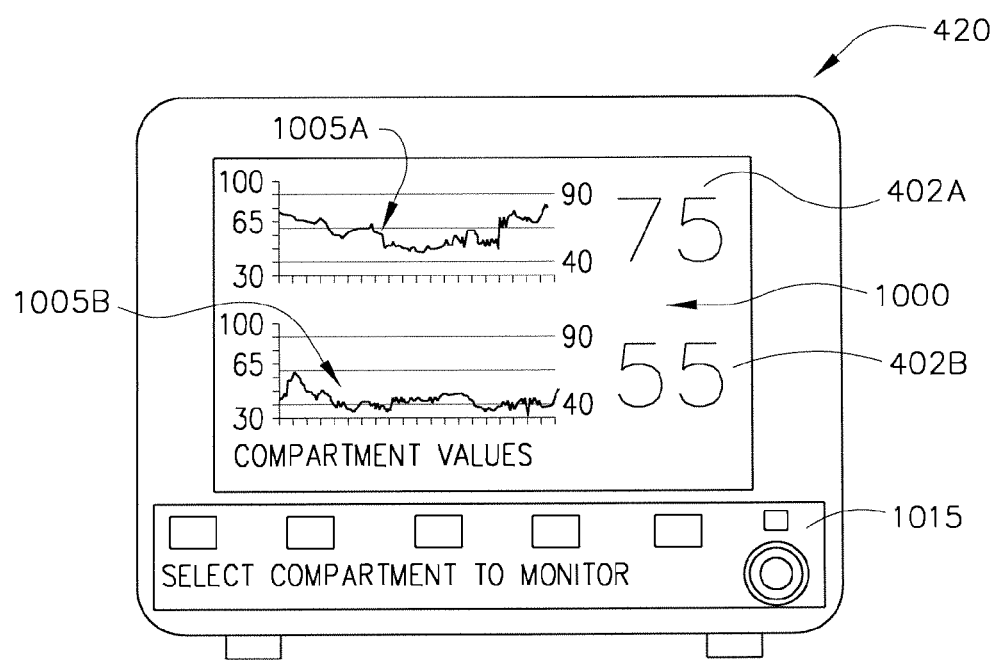
FIG. 10 illustrates an exemplary display of numeric oxygenation values as well as graphical plots for at least two compartments of an animal according to one exemplary embodiment of the invention.

Referring now to FIG. 10, this figure illustrates an exemplary display 1000 of numeric oxygenation values 402 as well as graphical plots 1005 for at least two compartments of an animal according to one exemplary embodiment of the invention. The graphical plots 1005 can display the current instantaneous oxygenation level for each compartment as a point as well as historical data displayed as other points along a line that plots the history for a particular compartment sensor 405. In other words, the X-axis of the plots 1005 can denote time in any increments while the Y-axis of the plots can denote oxygenation levels monitored by a particular sensor 405.

While only two plots are illustrated, multiple plots can be displayed for each respective sensor 405. In compartment sensor array 805 deployments, the graphical plot 1005 can represent an "average" of oxygenation levels measured by the multiple sensors of a particular linear compartment sensor array 805. The display device 420 can include controls 1015 that allow for the selection of one or more compartment sensors 405 or one or more compartment sensor arrays 805 for displaying on the display device 420. The display of historical oxygenation levels of a compartment 905 over time through the plots 1005 is a significant improvement over conventional methods of direct pressure readings of compartments 905 which usually would only allow periodic measurements of compartments 905 on the order of every fifteen or thirty minutes compared to minutes or seconds now measured with the compartment sensors 405 described in this document.

Figure 11:
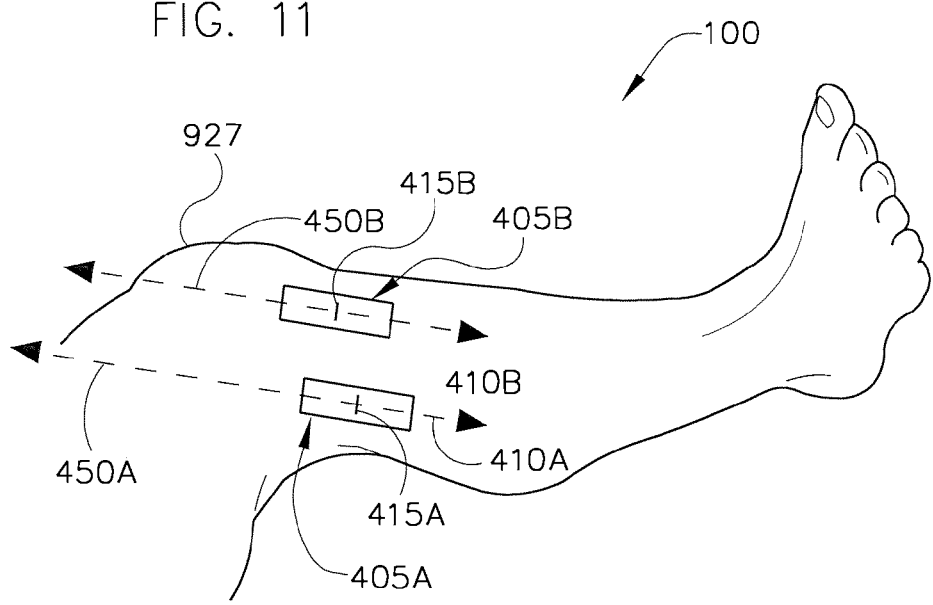
FIG. 11 illustrates single compartment sensors with alignment mechanisms and central scan depth markers that can be used to properly orient each sensor with a longitudinal axis of a compartment of an animal body according to one exemplary embodiment of the invention.

Referring now to FIG. 11, this figure illustrates single compartment sensors 405 with alignment mechanisms 410 and central scan depth markers 415 that can be used to properly orient each sensor 405 with a longitudinal axis 450 of a compartment 905 of an animal body according to one exemplary embodiment of the invention. While the longitudinal axis 450 of a compartment (shown with broken lines) cannot actually be seen on the external surface of a lower human leg 100 by a medical practitioner, a medical practitioner can envision this invisible axis 450 based on the anatomy of the leg, such as looking at the knee 927 and comparing its orientation with the ankle and foot of the leg 100. As described above, the compartment extends from the knee to ankle and the sensor can be placed over a portion or all of the compartment being measured. With these single compartment sensor 405 embodiments, each sensor 405 can be positioned along the length of the longitudinal axis 450 to obtain an oxygenation level for a particular compartment 905 of interest.

Figure 12:
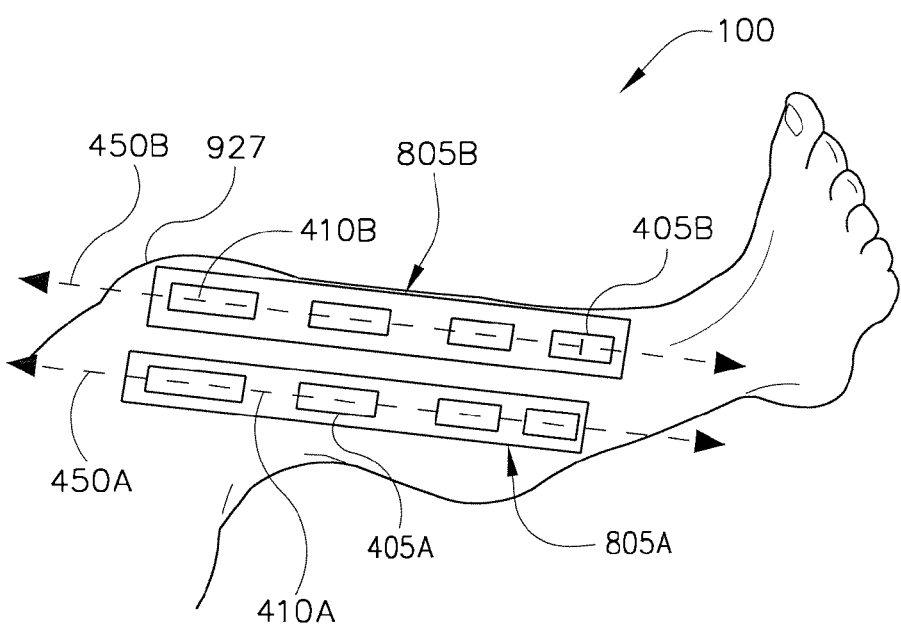
FIG. 12 illustrates compartment sensor arrays with alignment mechanisms that can be used to properly orient each array with a longitudinal axis of a compartment of an animal body according to one exemplary embodiment of the invention.

Referring now to FIG. 12, this figure illustrates compartment sensor arrays 805 with alignment mechanisms 410 that can be used to properly orient each array 805 with a longitudinal axis 450 of a compartment 905 of an animal body according to one exemplary embodiment of the invention. Since compartment sensor arrays 805 will typically occupy close to the entire length of any given longitudinal axis 450 of a compartment 905 of interest, the individual sensors 405 of the compartment sensor array 805 are usually not provided with central scan depth markers 415. In the sensor array embodiments, the arrays 805 are usually provided only with the alignment mechanism 410. However, the central scan depth markers 415 could be provided if desired for a particular application or medical practitioner (or both).

Referring now to FIG. 13A, this Figure illustrates various locations for single compartment sensors 405 that can be positioned on a front side of animal body, such as a human, to measure oxygenation levels of various compartments 905 according to one exemplary embodiment of the invention. FIG. 13A illustrates that the invention is not limited to compartment sensors 405 that only measure lower legs 100 of the human body. The compartment sensors 405 can measure various different compartments 905 such as, but not limited to, compartments 905 of the arm, thighs, and abdomen.

Figure 13B:
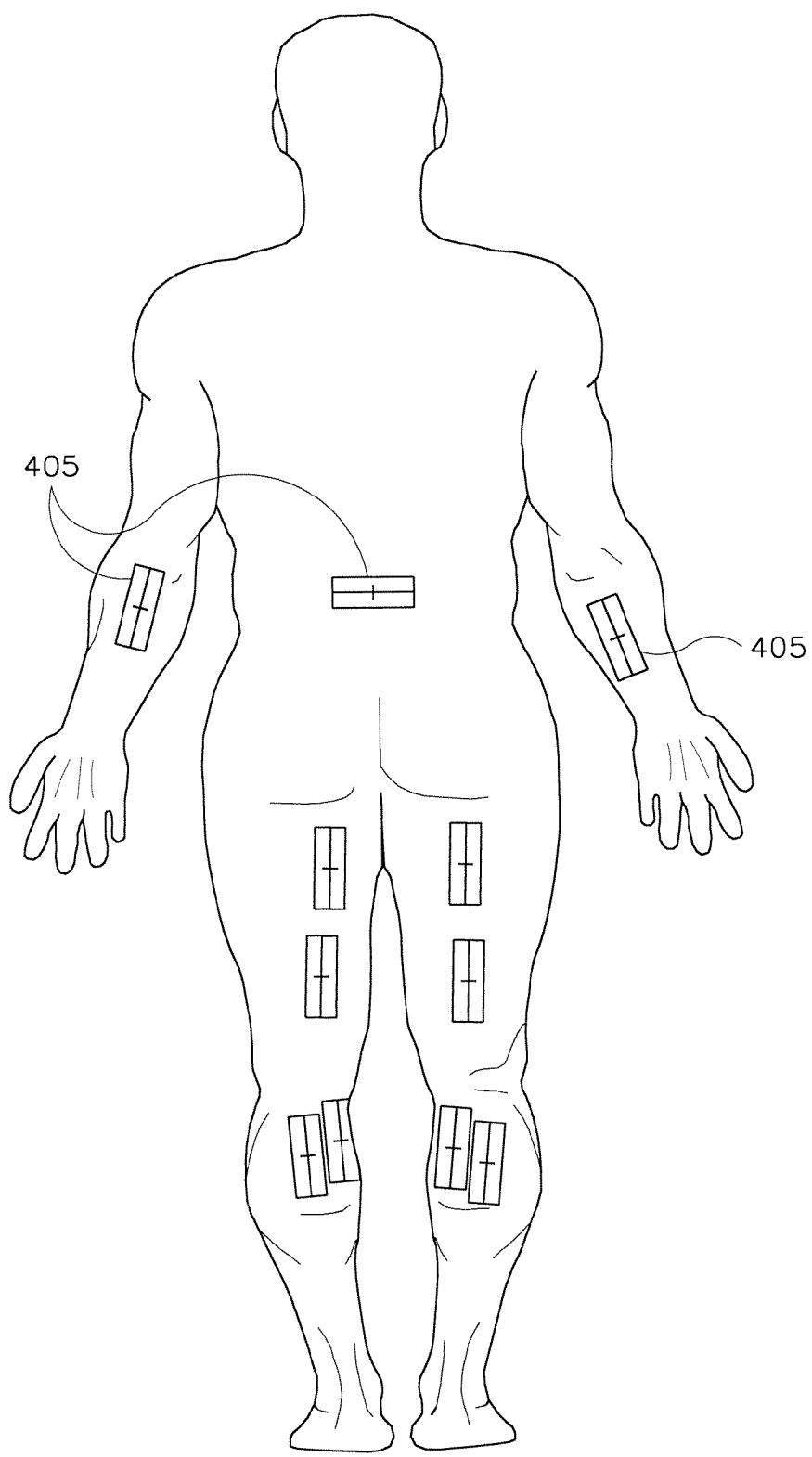
FIG. 13B illustrates various locations for single compartment sensors that can be positioned on a rear side of animal body, such as a human, to measure oxygenation levels of various compartments according to one exemplary embodiment of the invention.

Referring now to FIG. 13B, this Figure illustrates various locations for single compartment sensors 405 that can be positioned on a rear side of animal body, such as a human, to measure oxygenation levels of various compartments 905 according to one exemplary embodiment of the invention. Similar to FIG. 13A above, the compartment sensors 405 shown in this Figure can measure various different compartments 905 such as, but not limited to, compartments 905 of the arm, thighs, and abdomen. Also, while grouped compartment sensors 405 that are coupled together with expansion devices 535 are not illustrated here (such as those described in connection with FIG. 5A above), one of ordinary skill recognizes that such grouped compartment sensors can be substituted anywhere were the single compartment sensors 405 are shown.

Figure 14A:
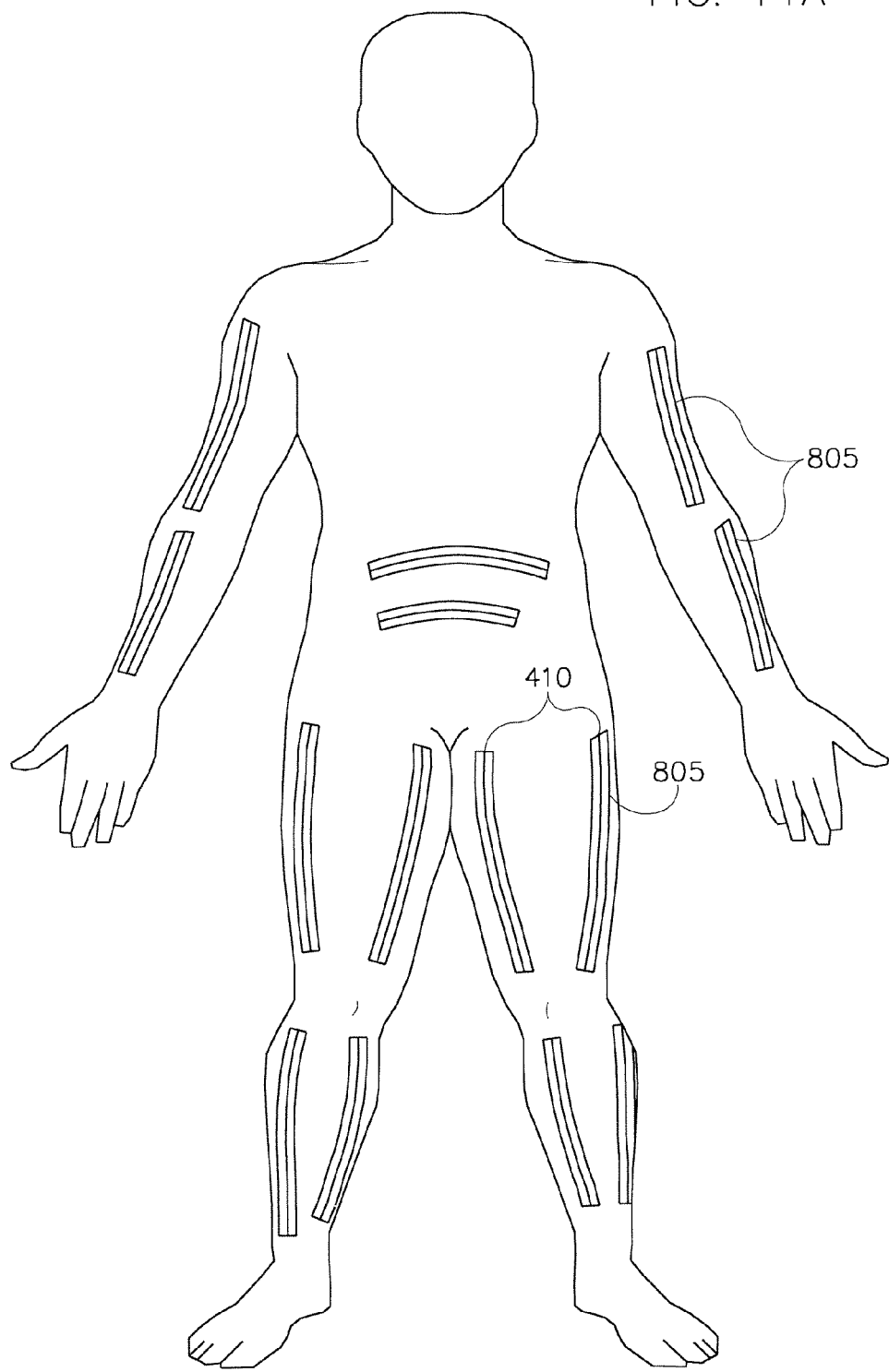
FIG. 14A illustrates various locations for compartment sensor arrays that can be positioned over compartments on a front side of an animal body, such as a human, to measure oxygenation levels of the various compartments according to one exemplary embodiment of the invention.

Referring now to FIG. 14A, this Figure illustrates various locations for compartment sensor arrays 805 that can be positioned over compartments 905 on a front side of an animal body, such as a human, to measure oxygenation levels of the various compartments 905 according to one exemplary embodiment of the invention. Like the single compartment sensor embodiments of FIGS. 13A-13B described above, the compartment sensor arrays 805 can measure various different compartments 905 such as, but not limited to, compartments 905 of the arm, thighs, and abdomen.

Referring now to FIG. 14B, this Figure illustrates various locations for compartment sensor arrays 805 that can be positioned over compartments 905 on a rear side of an animal body, such as a human, to measure oxygenations levels of the various compartments 905 according to one exemplary embodiment of the invention. Also, while grouped compartment sensor arrays 805 that are coupled together with expansion devices 535 are not illustrated here (such as those described in connection with FIG. 8B above), one of ordinary skill recognizes that such grouped compartment sensor arrays 805 can be substituted anywhere were the individual compartment array sensors 805 are shown.

Figure 14C:
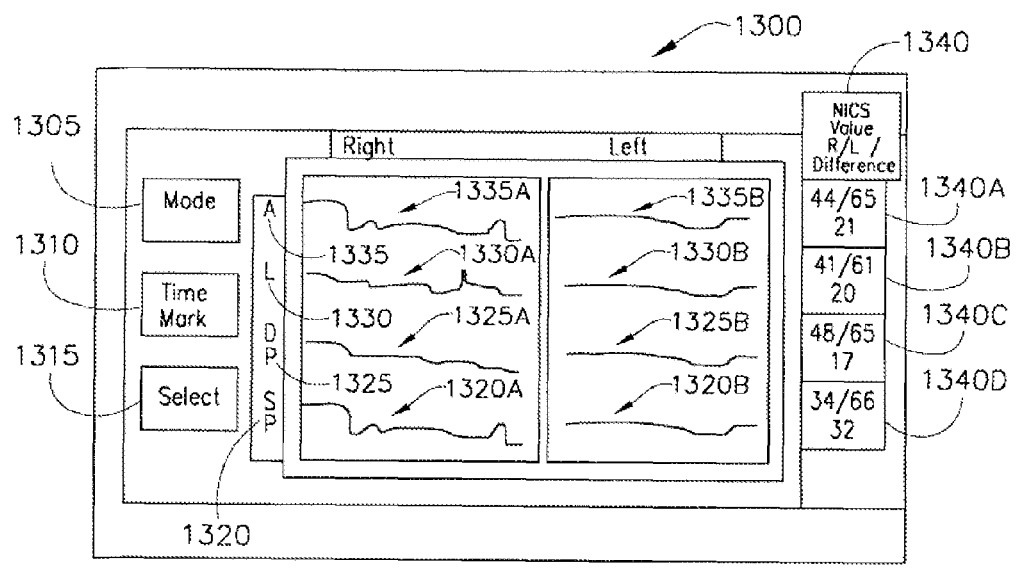
FIG. 14C illustrates an exemplary display and controls for the display device that lists data for eight single compartment sensors according to one exemplary embodiment of the invention.

Referring now to FIG. 14C, this Figure illustrates an exemplary display 1300 and controls for the display device 420 that lists data for eight single compartment sensors 405 according to one exemplary embodiment of the invention. The eight single compartment sensors 405 may be monitoring compartments of two limbs of an animal, such as two lower legs of a human patient. One limb is usually uninjured while the other limb is typically injured, though the system is not limited to unilateral injuries.

The display 1300 may provide up to eight different plots or graphs 1335A, 1330A, 1325A, 1320B, 1335B, 1330B, 1325B, 1320B of data that are taken from the eight different sensors 405 or sensor arrays 805. The first pair of right and left leg sensors may monitor the anterior compartment 905B of FIG. 9A which is displayed with the letter "A" for the first row 1335 of data. The second pair of right and left leg sensors may monitor the lateral compartment 905A of FIG. 9A which is displayed with the letter "L" for the second row 1330 of data. The third pair of right and left leg sensors may monitor the deep posterior compartment 905C which is displayed with the letters "DP" for the third row 1325 of data. The first pair of right and left leg sensors may monitor the superficial posterior compartment 905D which is displayed with the letters "SP" for the fourth row 1320 of data.

The display 1300 may also provide a measure of a difference 1340 in oxygenation levels between the injured limb or region and the uninjured limb or region. This difference may be displayed by listing the two oxygenation levels of each respective limb separated by a slash "/" line. Underneath the two oxygenation levels for a respective pair of sensors for the injured and uninjured limbs, a value which is the difference between the oxygenation levels displayed above it may be listed. For example, for the first oxygenation difference value of 1340A, the oxygenation level for the right leg sensor is the value of forty-four while the value for the left leg sensor is the value of sixty-five. In this exemplary embodiment, the right leg is injured while the left leg is uninjured. The difference value displayed under the two oxygenation levels for the first data set 1340A is twenty-one.

Initial data from patients with extremity injuries measured by the inventor have shown that muscular skeletal injuries cause hyperemia (increased blood flow and oxygen) in the injured extremity. If a compartment syndrome develops, the oxygenation drops from an elevated state to an equal and then lower level with comparison to the uninjured limb. Therefore when comparing injured and uninjured extremities, the injured limb should show increased oxygenation levels. If levels begin to drop in the injured limb compared to the uninjured limb, an alarm or alert can be triggered to warn the medical practitioner. This alarm can be visual or audible (or both).

With the display 1300, a medical practitioner can modify how data is displayed by pressing the "mode" button 1305 on the display 1300 (which may comprise a "touch-screen" type of display). The mode button 1305 permits the medical practitioner to change the display of the screen. This function would allow for selection between multiple different settings to allow for data downloading, changing the time frame for which data is displayed, etc. With the time mark "button" 1310, the medical practitioner can mark or "flag" certain data points being measured for later review. With the select "button" 1315, the medical practitioner can select between the multiple options that can be accessed through the mode button.

While the above description of FIG. 14C mentioned that eight single compartment sensors 405 produced the data of the display 1300 of FIG. 14C, the single compartment sensors 405 can be easily substituted by compartment sensor arrays 805. In such a scenario in which compartment sensor arrays 805 are used to produce the data of display 1300, the displayed values can be an "average" of the values taken from a given array 805. This "average" can be calculated by the processor of the display device 420.

Figure 14D:
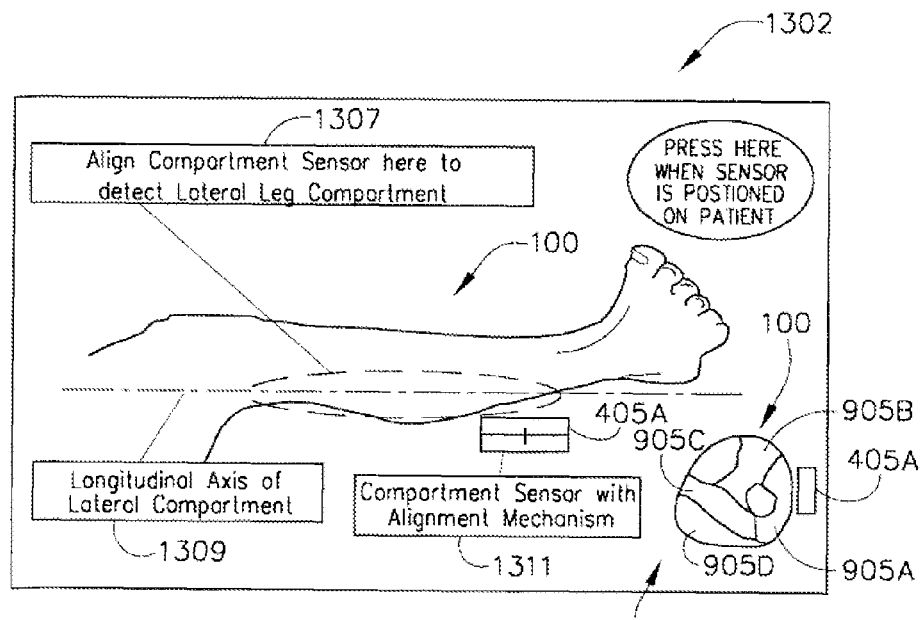
FIG. 14D illustrates an exemplary display of providing users with guidance for properly orienting a single compartment sensor over a compartment of an animal, such as a human leg, according to one exemplary embodiment of the invention.

Referring now to FIG. 14D, this Figure illustrates an exemplary display 1302 of providing users with guidance for properly orienting a single compartment sensor 405 over a compartment of an animal, such as a human leg, according to one exemplary embodiment of the invention. The display 1302 can be generated by display device 420 so that a medical practitioner is provided with instructions and graphical information on how to mount and operate the compartment sensors 405 of the system. The display may provide an illustration of the body part having the compartment of interest. In the exemplary embodiment of FIG. 14D, the compartment of interest is located within the lower human leg 100.

An illustration of the lower human leg 100 is provided in display 1302. On the body part having the compartment of interest, the display device 420 can identify the longitudinal axis 450 by marking or flagging this axis 450 with a text box label 1309. The display 1302 can also identify an illustration of the compartment sensor 405A by marking or flagging this illustration with another text box label 1311. The display 1302 can also identify a general region for a compartment of interest by encapsulating the region with a geometric outline such as an ellipse and marking this ellipse with another text box label 1307.

The display 1302 can also include a miniaturized view 1301 of a cross-section of the compartment of interest, similar to the views illustrated in FIGS. 9A and 9B for this exemplary embodiment that is assessing a lower leg compartment 905. The display 1302 may also allow the user to expand the cross-sectional view 1301 of the compartment of interest by allowing the user to double-click or touch the actual display of the cross-section. Multiple sections including an axial, coronal and/or sagittal view may be included in the on-screen instructions for placement. Upon such action by the user, the display device 420 may enlarge the cross-sectional view 1301 to a size comparable or equivalent to that illustrated in FIG. 9A. Once the medical practitioner has positioned the sensor 405 on the patient over the desired compartment of interest, the display 1302 can be refreshed to include the next compartment of interest.

Figure 15A:
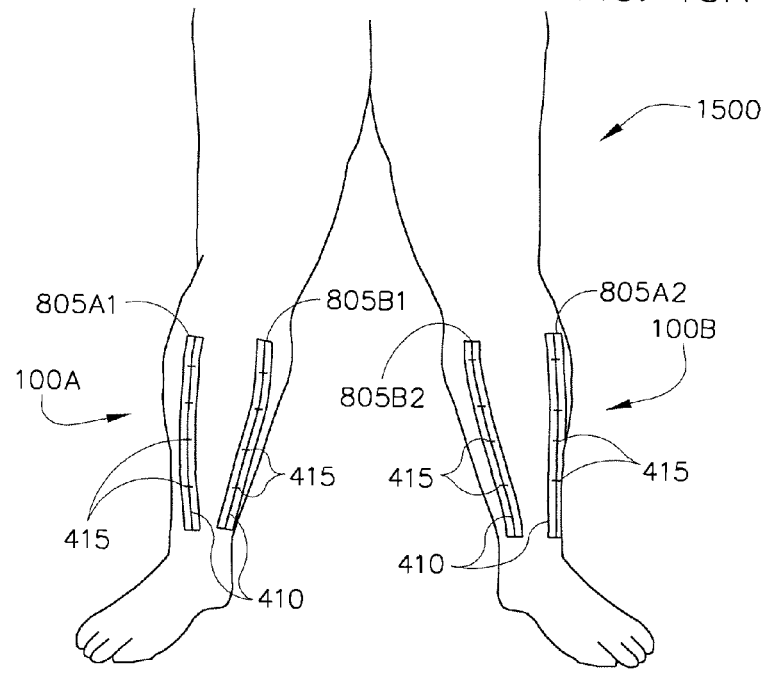
FIG. 15A illustrates a front view of lower limbs, such as two lower legs of a human body, that are being monitored by four compartment sensor arrays according to an exemplary embodiment of the invention.

Referring now to FIG. 15A, this Figure illustrates a front view 1500 of lower limbs, such as two lower legs of a human body, that are being monitored by four compartment sensor arrays 805 according to an exemplary embodiment of the invention. The four sensor arrays 805 can be positioned along compartments of interest by orienting the alignment mechanism 410 along the longitudinal axis of a respective compartment. Multiple central scan depth markers 415 and numerical depths (not illustrated in FIG. 15A) can be positioned over each light source/receptor set of a sensor array 805 to locate where each measurement is obtained for identifying sites of a hematoma, which will be described in more detail in connection with FIGS. 15B-16 below.

Figure 15B:
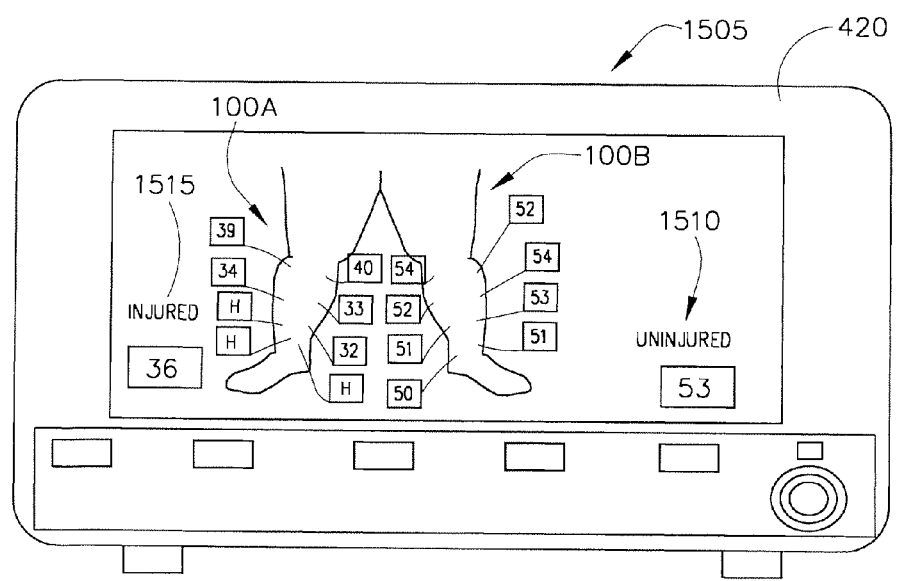
FIG. 15B illustrates a display of the display device that can be used to monitor hematomas and/or blood flow according to one exemplary embodiment of the invention.

Referring now to FIG. 15B, this Figure illustrates a display 1505 of the display device 420 that can be used to monitor hematomas and/or blood flow according to one exemplary embodiment of the invention. The display 1505 can include an average oxygenation level 1515 of thirty-six at an instant of time that is determined from the two compartment sensor arrays 805A1, 805B1 of a patient's right leg 100A which is injured in this exemplary case. Meanwhile, the display 1505 can also include an average oxygenation level 1510 of fifty-three at the same instant of time that is determined from the two compartment sensor arrays 805A2, 805B2 of a patient's left leg 100B which is uninjured in this exemplary case.

The display 1505 can also provide oxygenation values that it is receiving from each of the individual sensors 405 in a first sensor array 805 not illustrated. For the injured right leg 100A illustrated in the display, the oxygenation levels vary between thirty-two and forty-four. However, in the exemplary embodiment illustrated in FIG. 15B, there are three individual sensors 405 (not illustrated in this Figure) of the sensor array 805A1 that are not producing any oxygenation values which have been provided with the letter "H" to denote a possible hematoma. For the uninjured leg 100B, the individual compartment sensors 405 (not illustrated) of the two sensor arrays 805A2, 805B2 have provided oxygenation levels that range between 50 and 54 which are believed to be in the normal range for normal blood flow. Also, While individual sensors 405 that are not illustrated here (such as those described in connection with FIG. 4A above), one of ordinary skill recognizes that such individual compartment sensors 405 can be substituted anywhere were the compartment array sensors 805 are shown.

Figure 16:
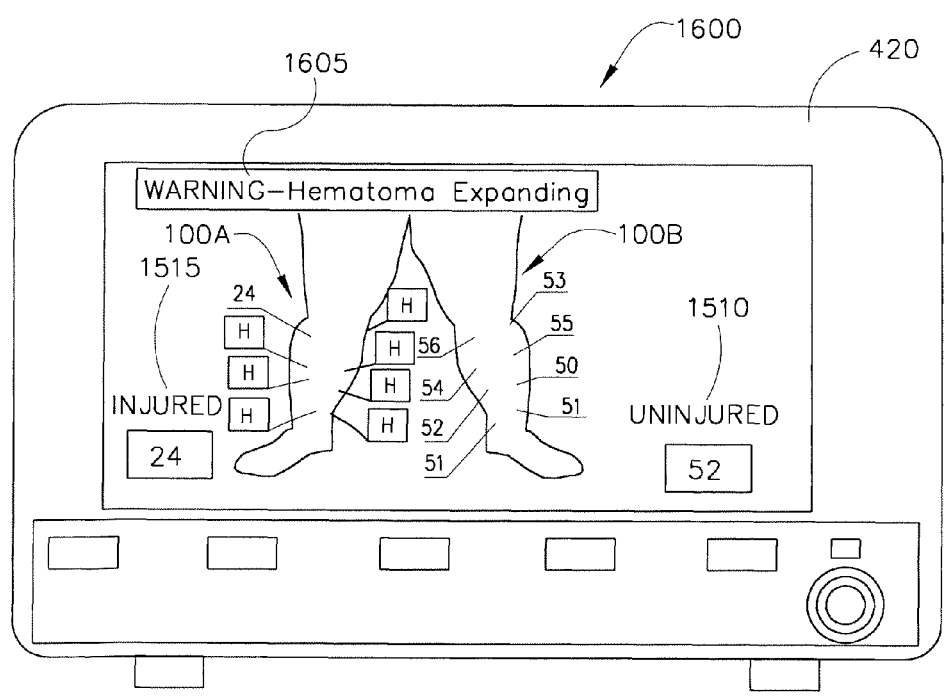
FIG. 16 illustrates a display of the display device for an instant of time after the display of FIG. 15B and which can be used to monitor hematomas and/or blood flow according to one exemplary embodiment of the invention.

Referring now to FIG. 16, this Figure illustrates a display 1600 of the display device 420 for an instant of time after the display of FIG. 15B and which can be used to monitor hematomas and/or blood flow according to one exemplary embodiment of the invention. The display 1600 illustrates that the hematoma or absence of healthy blood flow condition being tracked by sensor arrays 805A1, 805B1 (of FIG. 15A) is expanding. The display 1600 can include a warning message 1605 such as "WARNING—HEMATOMA EXPANDING!" to alert the medical practitioner of the changing conditions of the compartments 905 of interest in the injured or traumatized area. In FIG. 16, the average oxygenation level 1510 of the injured leg 100A decreased in value from thirty-six to twenty-four. Further, the number of individual sensors 405 (not illustrated but values shown) detecting a hematoma or lack of healthy blood flow condition increased from two sensors detecting the condition in FIG. 15B to seven sensors detecting the condition in FIG. 16 as indicated by the "H" values on display 1505. Meanwhile, the average oxygenation level 1515 of the uninjured left leg 100B changed slightly from fifty-three to fifty-two.

With the display 1600 that provides the compartment sensors 405 with "H" values in combination with the central scan depth markers 415 provided on the sensor arrays 805, the medical practitioner can easily locate the physical sites on the leg 100 that contain the hematoma or lack of healthy blood flow. These positions can also be used by the medical practitioner to locate appropriate amputation level for diabetics or peripheral vascular disease, since peripheral vascular disease is typically worse distally (closer to the toes) and gradually improves closer to the knee. The compartment sensor 405 or more specifically the array system 805 can be used to aid a clinician or surgeon in determining the level of amputation for peripheral vascular disease and or diabetes mellitus. By obtaining multiple readings at different levels from the knee to the ankle, the surgeon can determine the appropriate level for amputation. The level of amputation is important since if the tissue is not well perfused, the surgical wound will not heal and require revision surgery and more of the patient's leg must be removed.

Figure 17:
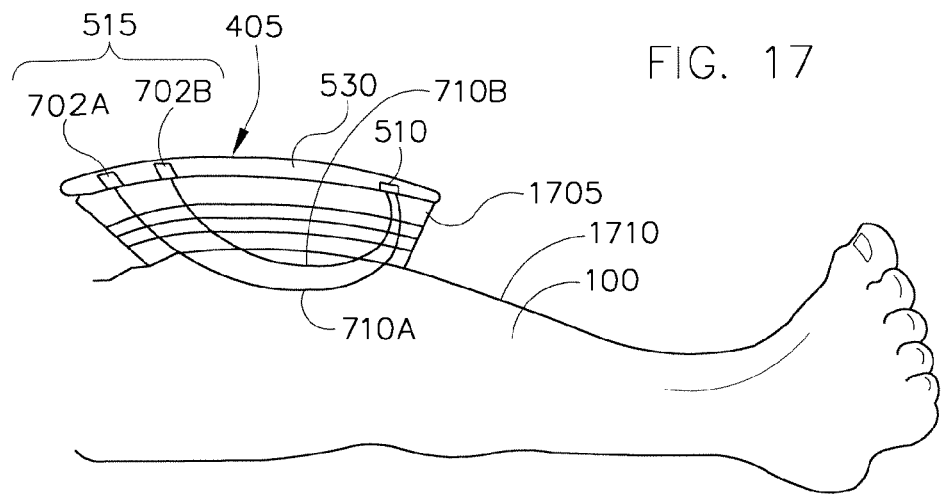
FIG. 17 illustrates a sensor design for measuring the optical density of skin according to one exemplary embodiment of the invention.

Referring now to FIG. 17, this Figure illustrates a sensor design for measuring the optical density of skin according to one exemplary embodiment of the invention. The depth of tissue measurement using NIRS is based on separation of the optical transmitter 510 and the optical receiver (see FIGS. 18A-B). In order to obtain readings of only the skin (very shallow depths), the separation between the optical transmitter 510 and optical receiver 515 would have to be very small and which may not be feasible. In this exemplary embodiment, the sensor 405 can comprise a material 1705 of known optical density that can be positioned between the substrate 530 and the skin 1710. In this way, the light mean paths 710A, 710B will only penetrate upper layers of the leg 100, such as the skin layers 1710. The thickness of the known material 1705 can be varied to adjust for different desired scan depths made by the light mean paths 710A, 710B. Since the optical density of the material 1705 is known, then any near infrared light absorption will be attributable to the layers of tissue of interest. And in this case, the optical density of the skin 1710 can be determined. According to a further exemplary embodiment, one of the photoreceptors 702A, 702B can be removed from the optical receiver 515 in order to decrease the depth of the scan. For example, if the second photoreceptor 702A was removed, the depth of the scan would only extend as deep as the light mean path 710B for the photoreceptor 702B.

The inventor has recognized that skin pigmentation can affect the oxygenation values of a patient that uses near-infrared compartment sensors 405. This effect on oxygenation levels is also acknowledged in the art. See an article published by Wassenar et al. in 2005 on near-infrared system (NIRS) values. As with solar light, skin pigmentation caused by the biochemical melanin is a major factor in light absorption. In the inventor's research, skin pigmentation has been demonstrated to be a significant factor in measuring oxygenation levels among patients. The inventor has discovered that there was approximately a ten point difference when comparing low pigmentation subjects (Caucasians, Hispanics & Asians) with higher pigmented subjects (African American). The pigmented subjects had average scores of approximately ten points lower when compared to non-pigmented subjects.

See Table 1 below that lists data on the difference between measured oxygenation levels of uninjured patients due to skin pigmentation.

TABLE #1

Difference in measured oxygenation levels between White and Dark Pigmentation Skinned Subjects

| Avg | White | Dark | Diff | p value |
|---|---|---|---|---|
| Anterior | 60 | 51 | 9 | <0.0001 |
| Lateral | 61 | 52 | 9 | <0.0001 |
| Deep Post | 66 | 53 | 13 | <0.0001 |
| Sup Post | 66 | 52 | 14 | <0.0001 |

N = 10 (White) and 17 (Dark) (This study compared 10 white subjects to 17 darker pigmented subjects)
Statistics used a non paired, two tail student t-test for p-values
P values show very statistically significant differences between white (Caucasian, Asian & Hispanic) vs. Dark (African American) subjects The p-value can be described as the chance that these findings were due to chance alone. In all four compartments, the chance of finding the difference (9-14) in average value between the two groups (dark and white) was less than 0.01% or less than 1 out of 10,000. In other words the likelihood of these findings occurring by chance alone is very unlikely. By convention, statistically significant findings are considered to be less than 5% or a p-value of <0.05 in comparison. See APPENDIX A for the raw data that supports this data.

Conventional studies (Wassenar et al., 2005 and Kim et al., 2000) have showed that when subjects increase their activity, dark pigmented people tend to have higher rates of loss of signal.

There have been no attempts as of this writing to account for skin pigmentation, or optical density, in oxygenation levels detected with sensors like the compartment sensor 405 discussed above. Therefore, the design illustrated in FIGS. 17-18 have been developed by the inventor to account for pigmentation optical density. With the embodiments of FIGS. 17-18, skin pigmentation influences can be calibrated and accounted for when measuring oxygenation levels with sensors 405 that use near infrared light absorption principles. In this way, true or more accurate oxygenation levels of subcutaneous tissue such as muscle, cerebral matter or organ tissue may be obtained. This calibration or pigmentation accounting would also allow for comparison of values between different patients, since each individual will likely have different skin pigmentation values.

Figure 18A:
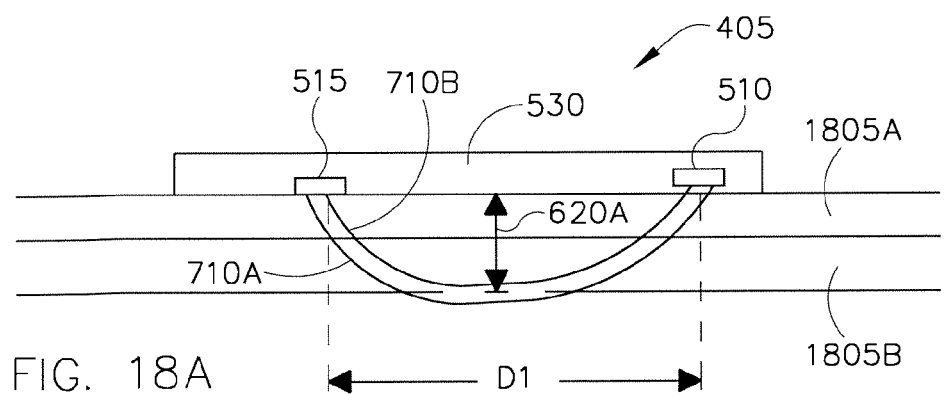
FIG. 18A illustrates a sensor that can penetrate two layers of skin to obtain optical density values according to one exemplary embodiment of the invention.

Referring now to FIG. 18A, this Figure illustrates a sensor 405 that can penetrate two layers of skin 1805A, 1805B to obtain optical density values according to one exemplary embodiment of the invention. The distance D1 between the optical transmitter 510 and optical receiver 515 can be predetermined based on the scan depth 620A that is desired.

Figure 18B:
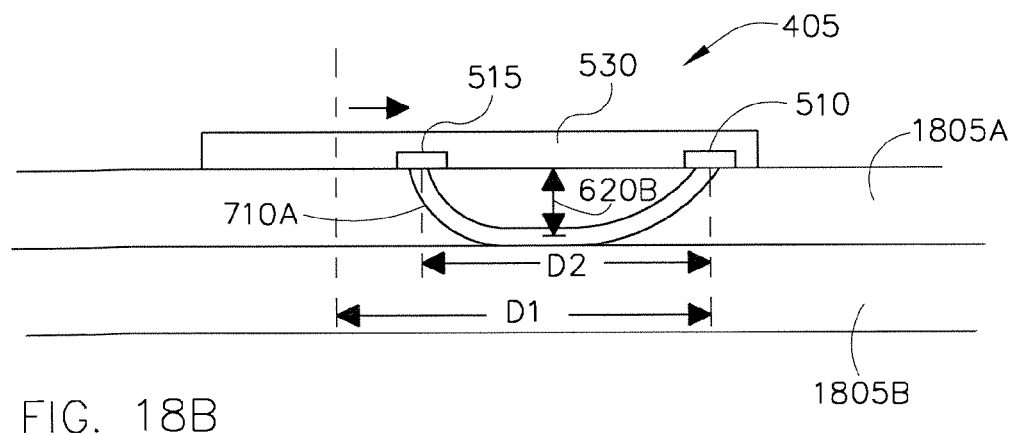
FIG. 18B illustrates a sensor that can penetrate one layer of skin according to one exemplary embodiment of the invention.

Referring now to FIG. 18B, this Figure illustrates a sensor 405 that can penetrate one layer of skin 1805A according to one exemplary embodiment of the invention. This figure demonstrates how the depth of measurement for oxygenation levels using the sensors 405 that operate according to near infrared light absorption principles is usually directly proportional to the optical transmitter and optical receiver separation distance D. In FIG. 18B, the separation distance D2 is smaller than that of the separation distance D1 of FIG. 18A. Accordingly, the central scan depth 620B of FIG. 18B is also shorter than the central scan depth 620A of FIG. 18A.

According to one exemplary embodiment of the invention, the separation D1 and D2 between the optical transmitter 510 and optical receiver 515 can range between approximately five millimeters to two centimeters. This separation distance D can be optimized to obtain an accurate reading of only the skin in the particular area of interest. One of ordinary skill in the art recognizes that skin is not a constant depth or thickness throughout a human body. Therefore, the depth 620 of the scan of a sensor 405 for which it is designed (ie. the leg for compartment syndromes) may preferably be designed to vary to obtain an accurate optical density value for skin in that specific body location.

Figure 18C:
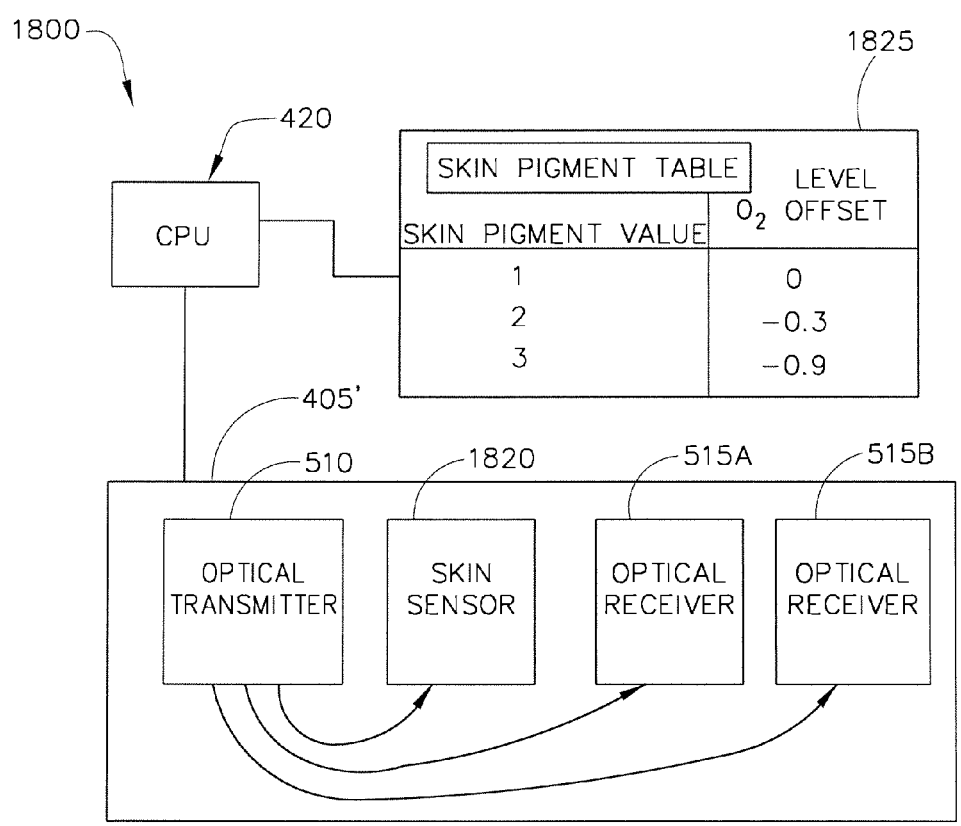
FIG. 18C illustrates a modified compartment monitoring system that can correlate skin pigmentation values with skin optical density values in order to provide offset values for oxygenation levels across different subjects who have different skin pigmentation according to one exemplary embodiment of the invention.

Referring now to FIG. 18C, this figure illustrates a modified compartment monitoring system 1800 that can correlate skin pigmentation values with skin optical density values in order to provide offset values for oxygenation levels (derived from near infrared light absorption principles) across different subjects who have different skin pigmentation according to one exemplary embodiment of the invention. The system 1800 can comprise a central processing unit of the display device 420 or any general purpose computer. The CPU of the display device 420 can be coupled to a compartment sensor 405' that has been modified to include a skin pigment sensor 1820.

The skin pigment sensor 1820 may be provided with a known reflectance and that can be used to calibrate the compartment sensor 405' based on relative reflectance of skin pigment which can affect data generated from oxygenation scans. For example, the skin sensor 1820 can comprise a narrow-band simple reflectance device, a tristimulus colorimetric device, or scanning reflectance spectrophotometer. Conventional skin sensors available as of this writing include mexameter-18 (CK-electronic, Koln, Germany), chromameters, and DermaSpectrometers. Other devices appropriate and well suited for the skin sensor 1820 are found in U.S. Pat. No. 6,070,092 issued in the name of Kazama et al; U.S. Pat. No. 6,308,088 issued in the name of MacFarlane et al; and U.S. Pat. No. 7,221,970 issued in the name of Parker, the entire contents of these patents are hereby incorporated by reference.

The skin sensor 1820 can determine a standardized value for skin pigmentation of a patient by evaluating the melanin and hemoglobin in the patient's skin. Once the skin melanin or pigment value is determined it can be correlated to its calculated absorption or reflectance (effect) on the oxygenation levels using a predetermined calibration system, such as the skin pigment table 1825 illustrated in FIG. 18C. From the skin pigment table 1825, the CPU 420 can identify or calculate an oxygenation offset value that can be incorporated in tissue hemoglobin concentration calculations for deep tissue oxygenation scans. Accounting for skin pigmentation will usually allow for information or values to be compared across different subjects with different skin pigmentation as well as using the number as an absolute value instead of monitoring simple changes in value over time.

Figure 19:
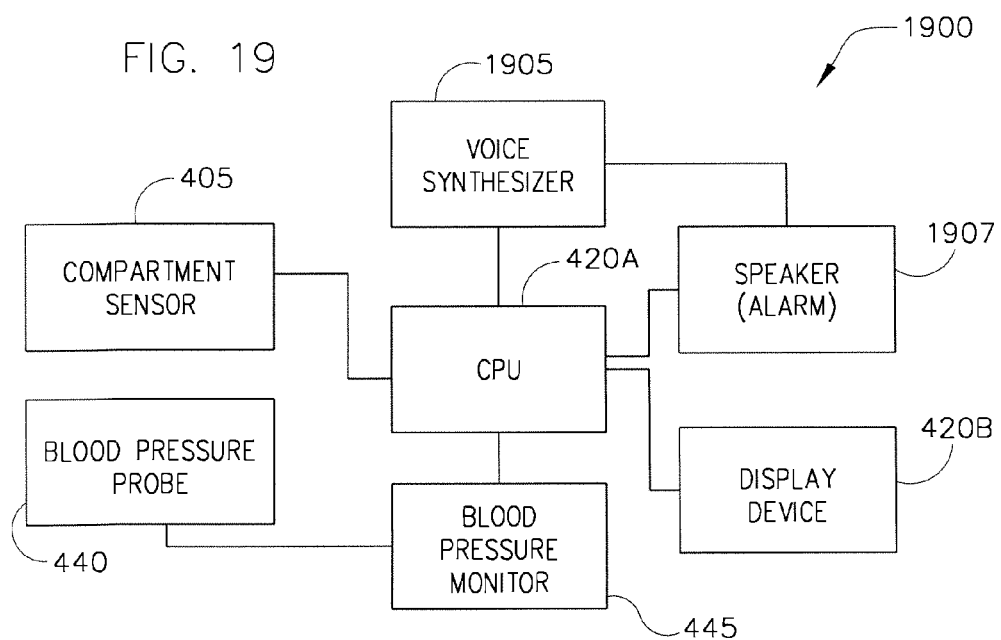
FIG. 19 is a functional block diagram of the major components of a compartment monitoring system that can monitor a relationship between blood pressure and oxygenation values according to one exemplary embodiment of the invention.

Referring now to FIG. 19, this figure is a functional block diagram of the major components of a compartment monitoring system 1900 that can monitor a relationship between blood pressure and oxygenation values according to one exemplary embodiment of the invention. The compartment monitoring system 1900 can include a CPU 420A of a display device 420B that is coupled to compartment sensors 405, a blood pressure probe 440, and a blood pressure monitor 445. The CPU 420A may also be coupled to a voice synthesizer 1905 and a speaker 1907 for providing status information and alarms to a medical practitioner.

The CPU 420A can receive data from the blood pressure monitor 445 in order to correlate oxygenation levels with blood pressure. The CPU 420A can activate an alarm, such as an audible or visual alarm (or both) with the voice synthesizer 1905 and speaker or displaying a warning message on the display device 420B when the diastolic pressure of a patient drops. It has been discovered by the inventor that perfusion can be significantly lowered or stopped at low diastolic pressures and when compartment pressures are greater than the diastolic pressure. According to one exemplary embodiment, in addition to activating an alarm, the CPU 420A of the compartment monitoring system 1900 can increase a frequency of data collection for oxygenation levels and/or blood pressure readings when a low blood pressure condition is detected by the system 1900.

Figure 20:
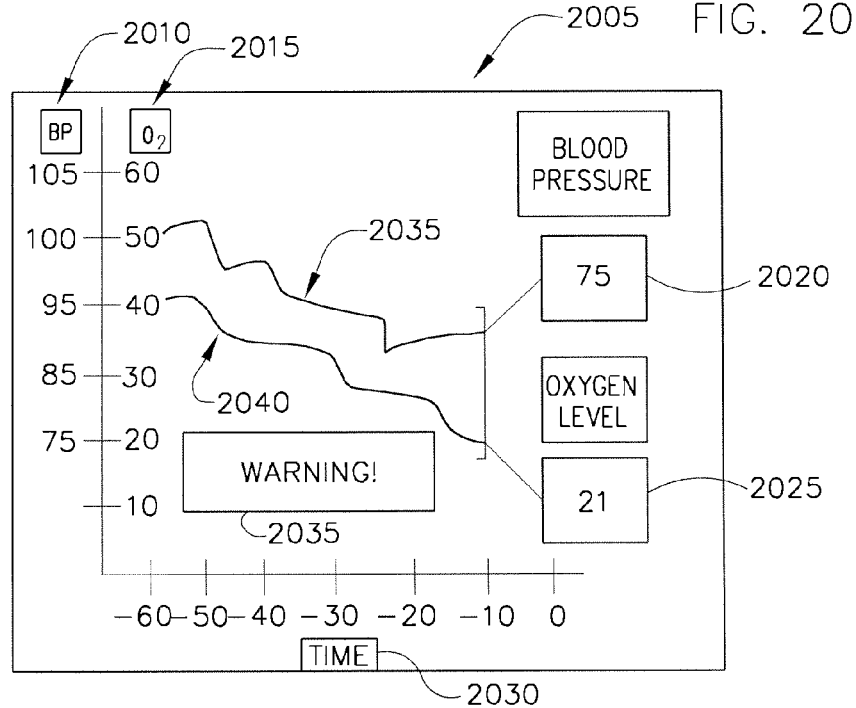
FIG. 20 is an exemplary display that can be provided on the display device and which provides current blood pressure values and oxygenation levels of a compartment of interest according to one exemplary embodiment of the invention.

Referring now to FIG. 20, this figure is an exemplary display 2005 that can be provided on the display device 420 and which provides current blood pressure values 2020 and oxygenation levels 2025 of a compartment of interest according to one exemplary embodiment of the invention. Display 2005 can be accessed by activation of the mode switch 1305 of FIG. 14.

In addition to displaying current blood pressure values 2020 and oxygenation levels 2025, the display 2005 can further include graphs that plot a blood pressure curve 2035 and an oxygenation level curve 2040. The blood pressure curve 2035 can represent blood pressure data taken over time that is plotted against the time axis 2030 (X-axis) and the blood pressure axis 2010 (first Y-axis values). The oxygenation level curve 2040 can represent oxygenation levels taken over time that is plotted against the time axis 2030 (X-axis) and the oxygenation level axis 2015 (second Y-axis values).

In this way, the relationship between blood pressure and potential compartment pressure based on the oxygenation levels can be directly tracked and monitored by a medical practitioner. As noted above, it has been discovered by the inventor that perfusion can be significantly lowered or stopped at low diastolic pressures and when compartment pressures are greater than the diastolic pressure. So when the blood pressure of a patient starts to drop and if the oxygenation levels of a compartment being tracked also start to drop, the CPU 420A can sound an audible alarm and display a warning message 2035 to the medical practitioner to alert him or her of this changing condition. This correlation between hemoglobin concentration (oxygenation levels) and diastolic pressure can be used to estimate intra-compartmental pressures without having to use invasive, conventional needle measurements.

Additionally, a running average of oxygenation values over a certain time period can be calculated and displayed. The time period could be altered between multiple time periods from seconds to minutes to even hours. The purpose of the running average would be to limit the amount of variability of the oxygenation values displayed on the screen. The current instantaneous value that is displayed in existing models is very labile. By using a running average, the trends can be monitored and the instantaneous changes can be smoothed out. This ability to decrease volatility would be important to prevent continual alert triggering if an alarm value was set by the medical practitioner.

In addition, with blood pressure input as described above, the diastolic, systolic and/or mean arterial pressure (MAP) can be displayed (not illustrated) against time on the same graph. Using the two data series of oxygenation and diastolic blood pressure, an estimate of perfusion pressure (diastolic pressure minus intra-compartmental pressure) can also be estimated by the CPU 420A.

Figure 21:
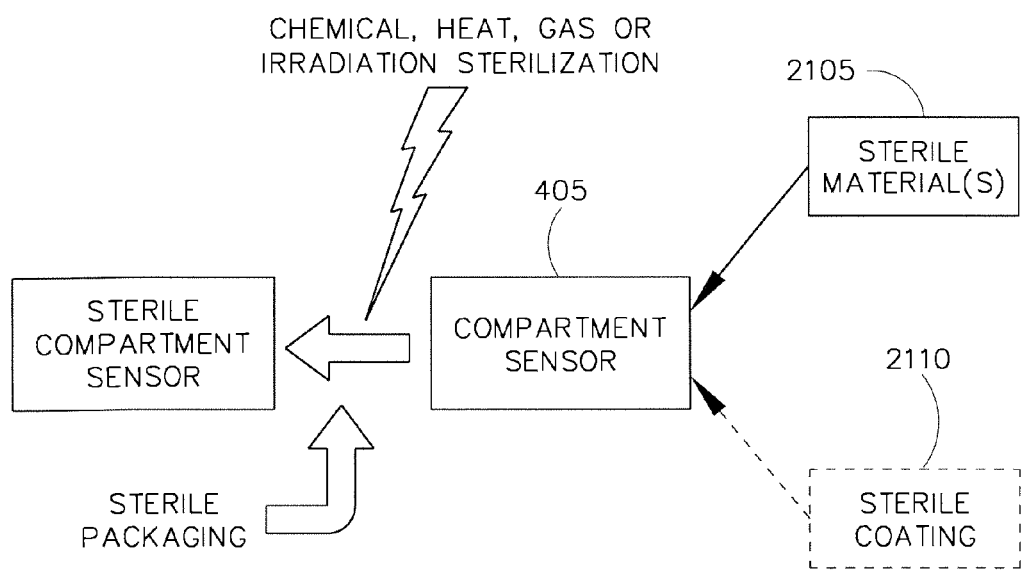
FIG. 21 is a functional block diagram that illustrates sterilized material options for a compartment sensor according to one exemplary embodiment of the invention.

Referring now to FIG. 21, this figure is a functional block diagram that illustrates material options for a compartment sensor 405 according to one exemplary embodiment of the invention. Functional block 2105 indicates that the structure of the compartment sensor can be made with sterile materials. For example, the substrate 530 (not illustrated) of the sensor 405 may be made of anyone or combination of the following materials: various polymers such as the polyurethanes, polyethylenes, polyesters, and polyethers or the like may be used. Alternatively, each compartment sensor can be made with a sterile coating 2110 that encapsulates the compartment sensor 405. The sterile coating can be applied during manufacturing of the sensor 405 or it can be applied after manufacturing and provided as a container or sealable volume. Additionally, once the unit is constructed and finished, the device can be sterilized using one or more off multiple processes including but not limited to chemical, heat, gas or irradiation sterilization.

Figure 22:
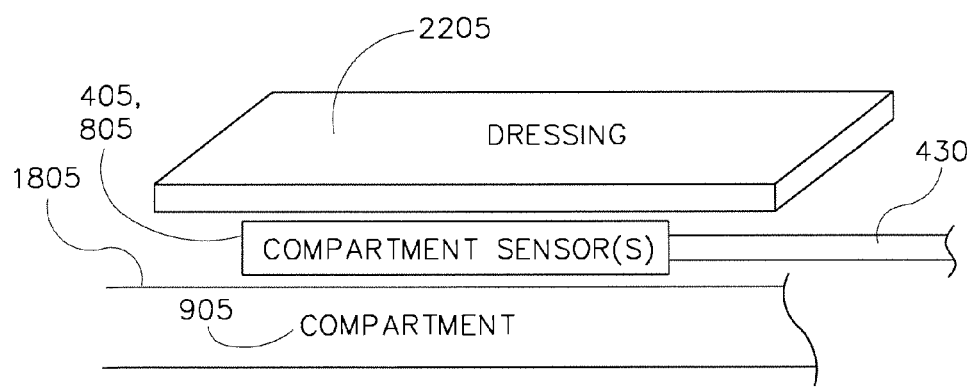
FIG. 22 illustrates an exemplary clinical environment of a compartment sensor where the sensor can be positioned within or between a dressing and the skin of a patient according to one exemplary embodiment of the invention.

Referring now to FIG. 22, this figure illustrates an exemplary clinical environment of a compartment sensor 405 where the sensor 405 can be positioned within or between a dressing 2205 and the skin 1805 of a patient according to one exemplary embodiment of the invention. Since the inventive compartment sensor 405 can be made with or enclosed by sterile materials as noted in FIG. 21 above, the compartment sensor 405 or an sensor array 805 can be positioned between a dressing 2205 and a skin layer 1805 of a patient intraoperatively. In this way, a medical practitioner can monitor a compartment 905 of interest without the need to remove the dressing 2205 or adjust the position of the compartment sensor 405.

Case Studies Using Compartment Sensors 405 and Conventional Pressure Measuring Methods Case I In 2007, a 44 year old Caucasian male fell 20 feet sustaining an isolated closed proximal tibia fracture with extension into the knee. Initial treatment included external fixation for stabilization on the day of injury. During surgery the compartments were firm but compressible. At post operative check revealed that the compartments were more firm. There was mild pain with passive stretch, though the patient was diffusely painful throughout both lower extremities. Intra-compartmental pressures were measured for all four compartments using a conventional needle method with a Striker device (Stryker Surgical, Kalamazoo, Mich.). The anterior and lateral pressures measured 50 mm Hg and the superficial and deep posterior compartments were 48 mm Hg. The diastolic pressure was 90 mm Hg resulting in a 40 mm Hg perfusion pressure.

Tissue oxygenation ($StO_2$) or oxygenation levels were evaluated using two compartment sensors 405. The oxygenation levels were approximately 80% in all four compartments. The compartment sensors 405 were placed on the lateral and deep posterior compartments for continual monitoring, which maintained oxygenation values near 80%. Higher percentage oxygenation levels indicate more perfusion and higher oxy-hemoglobin concentrations.

All clinical decisions were based of the clinical symptoms and pressure measurements and not on the oxygenation levels. Two hours passed and compartment pressures were repeated. The anterior and lateral compartments remained at 50 mm Hg. The superficial and deep posterior compartments rose to 50 mm Hg as well. The patient's diastolic pressure remained at 90 mm Hg maintaining 40 mm Hg of perfusion pressure. The oxygenation values remained near 80% for both the lateral and deep posterior compartments. Clinical symptoms were monitored closely throughout the night.

Approximately 24 hours after the initial injury, the patient became more symptomatic and began requiring more pain medication. Intra-compartmental measurements were repeated. The anterior and lateral compartments remained at 51 mm Hg. The superficial and deep posterior compartments measured 61 mm Hg and 63 mm Hg respectively. However, the diastolic pressure dropped to 74 mm Hg decreasing the perfusion pressure to 11 mm Hg. Based on the pressure measurements and clinical symptoms, the patient underwent fasciotomy and was found to have no gross evidence of muscle necrosis or neuromuscular sequelae at late follow up.

Throughout the monitoring period, the lateral compartment maintained an oxygenation level of approximately 80%. The oxygenation levels in the deep posterior compartment began in the eighties and started to drop approximately three hours after the second compartment pressure measurement. At time of fasciotomy, the oxygenation level for the deep posterior compartment was 58%. The gradual decline in muscle oxygenation mirrored the decrease in perfusion pressure over an extended period of time.

This first case suggests that the compartment sensors 405 can be used to continually monitor an injured extremity. Initially, the patient had elevated intra-compartmental pressures, but the perfusion pressure was greater than 30 mm Hg. The ensuing increase in clinical symptoms and decrease in perfusion pressure correlated with the gradual decrease in oxygenation levels. Impaired perfusion was reflected in a decline in the oxygenation levels. These results are consistent with a previous study by Garr et al. who showed a strong correlation between oxygenation levels and perfusion pressures in a pig model. This case also demonstrates the ability of compartment sensors 405 to differentiate between compartments in the leg since the oxygenation levels in the lateral compartment remained elevated while the deep posterior values declined.

Case II

Also in 2007, a 32 year old Hispanic male sustained an isolated, closed Schatzker VI tibial plateau fracture after falling from a scaffold. On initial evaluation, the patient had tight compartments, but there were no clinical symptoms of compartment syndrome. Active and passive range of motion resulted in no significant pain. Based on the concerns for the tense leg, intra-compartmental pressure measurements were obtained using a Stryker device.

All compartments were greater than 110 mm Hg. The patient's blood pressure was 170/112 mm Hg. The decision to perform a four compartment fasciotomy was made. The compartment sensors 405 were placed on the deep posterior compartment as well as the lateral compartment for continual monitoring. The lateral compartment was unable to give a consistent reading due to hematoma interference. The initial reading for the deep posterior was an oxygenation level of 65%. The deep posterior tissue oxygenation level steadily declined from 65% to 55% over the hour of preoperative preparation.

Upon intubation, a sharp drop in the oxygenation levels from 55% to 43% was observed. The anesthesia record showed a concomitant drop in blood pressure at the time of induction from 171/120 mm Hg to 90/51 mm Hg. The patient underwent an uneventful fasciotomy and external fixation. Tissue examination showed no gross signs of muscle necrosis and at nine months follow-up there were no signs of sequelea. The oxygenation level monitoring of the compartment was acutely responsive and showed real time changes to a decline in perfusion pressure in an injured extremity.

The responsiveness of the compartment sensors 405 to intra-compartmental perfusion pressure is demonstrated by this second case study. This patient was initially asymptomatic even though his compartments were over 110 mm Hg in all compartments. The oxygenation levels from the compartment sensors 405 were able to detect gradual perfusion declines over the hour prior to fasciotomy. Prior to induction of anesthesia, the patient was able to maintain some tissue oxygenation by maintaining a high diastolic blood pressure. Once the patient was anesthetized during intubation, the diastolic pressure was significantly reduced. The oxygenation levels of the compartments dropped within thirty seconds of induction because the slight perfusion gradient was completely abolished by the induced hypotension.

Case III

In 2007, a 62 year old Asian male suffered a closed mid-shaft tibia fracture in a motor vehicle crash. The patient was unresponsive and hypotensive at the scene of the accident and intubated prior to arrival. Upon presentation, the patient was hypotensive with a blood pressure of 90/55 mm Hg. The injured leg was clinically tight on examination.

Oxygenation levels were measured for all four compartments. The oxygenation levels were approximately at 50% for the anterior and lateral compartments while the two posterior compartments were approximately at 80%. The compartment sensors 405 were placed on the anterior and superficial posterior compartments for continued monitoring. Intra-compartmental pressures were measured at 50 mm Hg and 52 mm Hg in the anterior and lateral compartments respectively using the conventional Striker device (needle pressure measuring method). The superficial and deep compartment pressures were 19 mm Hg and 20 mm Hg respectively. After the patient was stabilized by the trauma team, he underwent fasciotomy. There were no gross signs of muscle necrosis and no complications at 7 months follow-up. Muscle oxygenation was able to differentiate between compartments with hypoperfusion and adequate perfusion in a hypotensive and intubated patient.

This third case is evidence that the compartment sensors 405 are useful in assessing established or existing compartment syndromes. The compartment sensors 405 can provide useful information in patients that are unable to give feedback during a clinical examination such as this patient who was intubated and hypotensive upon examination. These findings correlate with the findings by Arbabi et al. who demonstrated oxygenation levels to be responsive in hypotensive and hypoxic pigs in a laboratory setting. The compartment sensors 405 can distinguish between different compartments and their respective perfusions. Clinically, in this case, the whole leg was tense, but intra-compartmental pressures were only elevated in the anterior and lateral compartments. The oxygenation levels measured by the compartment sensors 405 were proportional to the perfusion pressure with low values in the anterior and lateral compartments, but elevated values in the two posterior compartments.

Conclusion for Three Case Studies:

These three cases suggest that compartment sensors 405 are responsive and proportional to perfusion pressures within the injured extremity. These findings support previous studies documenting the importance of perfusion pressure and not an absolute value in the diagnosis of compartment syndrome. The compartment sensors can distinguish between compartments and is useful in the unresponsive, intubated and hypotensive patient. Lastly, the compartment sensors 404 have the potential to offer a continual, noninvasive and real time monitoring system that is sensitive in the early compartment syndrome setting. In all three cases, a difference in oxygenation levels was demonstrated prior to any irreversible tissue injury.

Case IV

A 60 year old Middle Eastern male was shot in the right thigh. Initially the thigh was swollen but the patient was comfortable. After approximately 12 hours after the initial injury the patient began to complain of increasing pain and required more pain medication. The thigh was more tense upon clinical exam. The patient was taken to the OR for fracture fixation and potential fasciotomy of the thigh.

NIRS sensors were placed on the anterior, posterior and medial (adductors) compartments of the thigh. Values for the injured side were similar or decrease when compared to the uninjured side. As previously described, injured tissue should show increased values due to hyperemia. The injured side anterior, posterior and medial values were 54, 53 and 63 respectively. The uninjured values for the anterior, posterior and medial were 51, 55 and 63 respectively.

The compartment pressures were measured in all three compartments. The intra-compartmental pressures for the anterior, posterior and adductors were 44, 59 and 30 respectively. Once the patient was induced for anesthesia and the patient's blood pressure dropped from 159/90 to 90/61, the patients NIRS values dropped within in 30 seconds of the his blood pressure drop. Once the blood pressure was dropped and the perfusion pressure was eliminated, the new values for the anterior, posterior and medial compartments were 29, 40 and 35.

Study: Sphygmomanometer Model & Invention's Sensitivity & Responsiveness

A study was conducted to determine the sensitivity and responsiveness of the inventive compartment monitoring system 400. Specifically, the purpose of the study was to evaluate the invention over the anterior compartment with a cuff around the thigh at different pressures (simulating a compartment Syndrome) to show responsiveness to increasing pressures in the leg.

The inventor's hypothesis was that the inventive compartment monitoring system 400 will show normal oxygenation at levels below pressures equivalent to compartment syndrome. Once pressures become equal to the diastolic blood pressure, it was believed the inventive system 400 would show significant deoxygenation because the capillary perfusion pressure will be passed. Continued monitoring will be obtained until a plateau or nadir is obtained.

Materials & Methods:

Thigh Cuff Pressures: 0 mmHg: Baseline; Increase cuff by 10 mmHg and hold for 10 minutes; At the end of each ten minute period blood pressure and NIRS values were obtained; Repeat incremental increases until obtain decreased oxygenation level readings; and Observe post release response & time to return to baseline Outcomes:

It was confirmed that the compartment monitoring system 400 is sensitive to changing pressures. A correlation with decreased perfusion was discovered once the pressure approaches diastolic pressure. The inventive system 400 does not reflect complete vascular compromise until tourniquet pressure supersedes systolic blood pressure because of venous congestion. These findings are consistent with previously described studies.

Statistical Analysis:

A significant difference is observed once tourniquet pressure equals the diastolic pressure (Perfusion pressure of zero). The venous congestion phenomenon which has been described with the tourniquet model for compartment syndromes maintains some flow until cuff pressure is raised to above systolic pressure (no flow). Venous congestion is the phenomenon when the higher systolic blood pressure is able to overcome the tourniquet pressure applied to the leg during that burst of pressure created by the heart's contraction when the tourniquet compression is above diastolic pressure but below systolic pressure.

Figure 23:
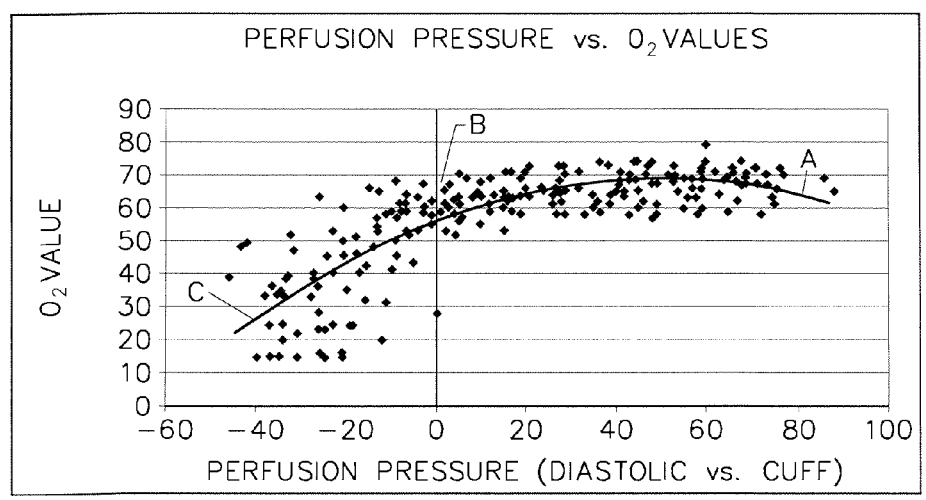
FIG. 23 is a graph of perfusion pressure plotted against oxygenation levels of a study conducted to determine the sensitivity and responsiveness of the inventive compartment monitoring system according to one exemplary embodiment of the invention.

Referring now to FIG. 23, this figure is a graph 2300 of perfusion pressure plotted against oxygenation levels ($O_2$) of the study conducted to determine the sensitivity and responsiveness of the inventive compartment monitoring system 400. The section between points A and B show the combined points of all subjects studied during the study when the tourniquet pressure was below the diastolic pressure. As shown in the graph, the grouping is mostly flat and does not show any decrease as the tourniquet pressure is increased. After point B between point B and C, the tourniquet pressure is above the diastolic pressure and the perfusion pressure becomes zero or negative. During this section of the graph, there is a significant drop in muscle oxygenation. The data points in FIG. 23 use the actual compartment monitoring values, which as described above, can vary based on skin pigmentation. Therefore, there is a wider range of values in oxygenation numbers and a wider spread of data points. See APPENDIX B for the raw data that supports this graph 2300.

Figure 24:
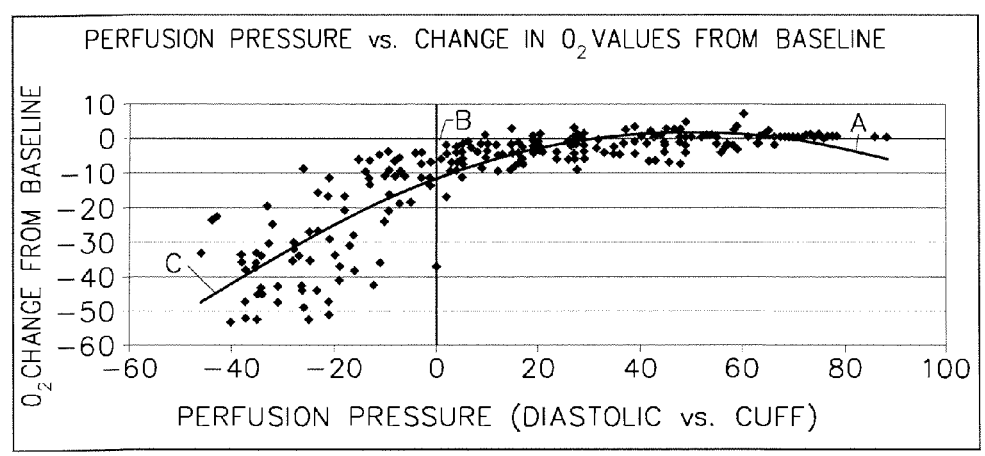
FIG. 24 is a graph of perfusion pressure plotted against a change in the oxygenation levels from a baseline for each subject of the study conducted to determine the sensitivity and responsiveness of the inventive compartment monitoring system according to one exemplary embodiment of the invention.

Referring now to FIG. 24, this figure is a graph 2400 of perfusion pressure plotted against a change in the oxygenation levels ($O_2$) from a baseline for each subject of the study conducted to determine the sensitivity and responsiveness of the inventive compartment monitoring system 400.

In the FIG. 24, the change from baseline was used instead of the absolute number presented by the compartment sensor. The effects of pigment were removed when change from baseline values was used. Baseline was defined as the value before the tourniquet was placed. The spread between data points is much less. As shown again between points A and B, there is a very small and gradual decrease in tissue oxygenation until point B (moving from high perfusion pressures to lower perfusion pressures or from right to left). Once the perfusion pressure, becomes zero or negative, the change from baseline was much larger and more rapid. Both graphs show how the tissue oxygenation is highly sensitive to perfusion pressure and the critical point is when the perfusion pressure changes from positive to negative. As described above, the diagnosis of compartment syndrome is based on the perfusion pressure (diastolic pressure minus compartment pressure). Therefore, the compartment monitoring system 400 has the capability to show real-time changes in perfusion prior to any irreversible tissue damage. See APPENDIX B for the raw data that supports this graph 2300.

This study supports the theory that oxygenation levels measure with the compartment sensors 405 decrease as perfusion pressure also decreases (Perfusion pressure=diastolic-cuff pressure). The study also indicates that there are no significant changes in measured oxygenation levels until there is increase above the diastolic pressure. The findings of this study as illustrated in FIGS. 23 and 24 correlate with previous studies using other determinants of flow (Xenon clearance; Clayton, 1977; Dahn, 1967; Heppenstall, 1986; Matava, 1994).

Study of Established Acute Compartment Syndromes:

Based on the clinical evaluation in established acute compartment syndrome patients the diagnosis of compartment syndrome was made. Its purpose was to evaluate the ability of the inventive compartment monitoring system 400 to detect hypoperfusion in the different compartments of the lower leg. This evaluation was made to demonstrate the invention's sensitivity to increased pressures versus uninjured legs.

Hypothesis:

There will be a significant difference between the injured and uninjured values of the compartment monitoring system 400. There will also be an inverse relationship between compartment pressures and measured oxygenation levels by the sensors 405. In other words, the oxygenation values would be directly proportional to perfusion pressures.

Material & Methods:

Oxygenation levels and pressure measurements for each compartment in established compartment syndromes were obtained. Readings for both legs were compared for each compartment.

Unknowns:

How will thick subcutaneous fat affect the compartment sensors 405?

What values will we obtain for the posterior compartments?

Preliminary Results:

Hyperemia (increased oxygenation levels) for fractures without any compartment syndrome symptoms has been demonstrated by the inventors studies (Table #3 and #4). In early compartment syndromes, the oxygenation values were equal between the two different legs. Once the compartment syndrome became advanced, and the perfusion pressure was decreased or eliminated, the oxygenation values in the injured leg dropped below the uninjured leg. There was some difficulty in obtaining oxygenation levels over a hematoma. Therefore, when oxygenation values between the two legs become equal, there should be concern for a compartment syndrome and fasciotomy should be considered. Once the injured levels drop below the uninjured leg, a fasciotomy should be performed.

Oxygenation levels are extremely responsive to changes in perfusion in regards to pressure changes. Compartment sensors 405 can differentiate between compartments. Oxygenation levels can work and are accurate in intubated patients. Oxygenation levels do respond over extended time periods and over very short periods of time and rapid changes in intra-compartmental pressures.

Oxygenation levels and hyperemia are maintained at least two to three days post injury or surgery. Post-operative values are also high in the operated on leg—.about.69-72 (Standard deviation of 9-12) with an average difference of 15-17%. The compartment sensors 405 work as a noninvasive tool. Oxygenation levels can be monitored by sensors 405 over extended periods of time. Compartment sensors 405 do respond to changes in perfusion both gradual and sudden. The sensors 405 can differentiate between different compartments.

TABLE #2

Comparison of Oxygenation Levels between Injured Limb and Non-injured Limb

| Avg | Injured | Uninjured | Diff | p value |
|---|---|---|---|---|
| Anterior | 46 | 54 | −6 | 0.07 |
| Lateral | 45 | 54 | −9 | 0.01 |
| Deep Post | 54 | 68 | −14 | 0.05 |
| Sup Post | 50 | 60 | −10 | 0.04 |

Significant difference using one tailed, paired student t-test was used for statistical analysis.

In three out of four compartments, the p-value showed statistical significance (p-value<0.05). The one compartment that was not less than 0.05, the anterior compartment, the p-value was 0.07 which is very close to 0.05. As described below, the normal situation should be the opposite. The injured side should be and is shown to be significantly higher when compared to the uninjured side. The p-value can be described as the chance that these findings were due to chance alone. By convention, statistically significant findings are considered to be less than 5% or a p-value of <0.05 in comparison. This means that there is a 5% chance that these findings are due to chance alone and that there is no difference between the two groups. See APPENDIX A for the raw data that supports this data.

Study of Fracture Hyperemia with Inventive Compartment Monitoring System 400

A study of fracture hyperemia with the inventive compartment monitoring system 400 was made. The purpose of this study was to examine non compartment syndrome patients with fractures of the lower leg.

Hypothesis:

The injured leg will show a hyperemic response to injury and have elevated blood flow causing an increase in oxygenation values.

Materials & Methods:

Compare uninjured leg to injured leg to see if there is a statistical and reproducible increase at time of injury. The data is important to describe normal fracture response to compare with compartment syndrome response.

Results:

Patients have approximately 15 pts higher on the injured side compared to the uninjured side. Time of measurement was approximately 16 hours post injury (range 2, 52).

TABLE #3

Oxygenation Values for Injured versus Uninjured Lower Leg Measurements.

| Avg | Injured | Uninjured | Diff | p value |
|---|---|---|---|---|
| Anterior | 69 | 55 | 14 | <0.0001 |
| Lateral | 70 | 55 | 15 | <0.0001 |
| Deep Post | 74 | 57 | 17 | <0.0001 |
| Sup Post | 70 | 56 | 14 | <0.0001 |

N = 26 (there were 26 subjects examined in this study.)

Statistical Analysis Calculated p-Values Using a Two Tailed, Paired Student t-Test.

In normal lower leg fracture situations without vascular injury or compartment syndrome, comparison between injured and uninjured legs show that the injured leg should be significantly higher with and average elevation of between 14 and 17 points. This finding is consistent with the hyperemia associated with injury. This effect is a long lasting effect that lasts over 48 hours after injury and surgery as seen by these results. The p-value can be described as the chance that these findings were due to chance alone. In all four compartments, the chance of finding the difference (14-17) in average value between the two groups (injured and uninjured) was less than 0.01% or less than 1 out of 10,000. In other words the likelihood of these findings occurring by chance alone is very unlikely. By convention, statistically significant findings are considered to be less than 5% or a p-value of <0.05 in comparison. See APPENDIX A for the raw data that supports this data.

TABLE #4

Oxygenation Values for Injured versus Uninjured
Lower Leg Measurements 2 Days After Surgery.

| Avg | Injured | Uninjured | Diff | p value |
|---|---|---|---|---|
| Anterior | 71 | 55 | 16 | <0.0001 |
| Lateral | 70 | 54 | 16 | <0.0001 |
| Deep Post | 73 | 58 | 15 | <0.0001 |
| Sup Post | 73 | 56 | 17 | <0.0001 |

N = 17 (This study included 17 patients)
Average time of measurement was 71 hours after injury and 44 hours after operation The p-value can be described as the chance that these findings were due to chance alone. In all four compartments, the chance of finding the difference (15-17) in average value between the two groups (injured and uninjured) was less than 0.01% or less than 1 out of 10,000. In other words the likelihood of these findings occurring by chance alone is very unlikely. By convention, statistically significant findings are considered to be less than 5% or a p-value of <0.05 in comparison. See APPENDIX A for the raw data that supports this data.

TABLE #5

Uninjured Controls Comparing Right and Left Leg Differences.

| Avg | Right | Left | Diff | Avg Val |
|---|---|---|---|---|
| Anterior | 55 | 54 | 1 | 55 |
| Lateral | 56 | 54 | 2 | 56 |
| Deep Post | 60 | 58 | 2 | 59 |
| Sup Post | 59 | 58 | 1 | 58 |

N = to 25 (There were 25 patients included in this study.)
No difference was found between right and left sides.

These findings are important for two different reasons. First, the difference between the two legs was very small (on average between 1 or 2 points). Therefore, the other findings that show significant differences between legs cannot be explained as normal variance. Uninjured patients have oxygenation values between the two legs that are typically very similar (within 1-5 points of each other). Second, normal oxygenation values for uninjured subjects were in the high 50's. This value varied based on pigmentation of the skin as showed above. See APPENDIX A for the raw data that supports this data.

Exemplary Method for Monitoring Oxygenation Levels of a Compartment

Referring now to FIG. 25, this figure is logic flow diagram illustrating an exemplary method 2500 for monitoring oxygenation levels of a compartment according to one exemplary embodiment of the invention. The processes and operations of the inventive compartment monitoring system 400 described below with respect to the logic flow diagram may include the manipulation of signals by a processor and the maintenance of these signals within data structures resident in one or more memory storage devices. For the purposes of this discussion, a process can be generally conceived to be a sequence of computer-executed steps leading to a desired result.

These steps usually require physical manipulations of physical quantities. Usually, though not necessarily, these quantities take the form of electrical, magnetic, or optical signals capable of being stored, transferred, combined, compared, or otherwise manipulated. It is convention for those skilled in the art to refer to representations of these signals as bits, bytes, words, information, elements, symbols, characters, numbers, points, data, entries, objects, images, files, or the like. It should be kept in mind, however, that these and similar terms are associated with appropriate physical quantities for computer operations, and that these terms are merely conventional labels applied to physical quantities that exist within and during operation of the computer.

It should also be understood that manipulations within the computer are often referred to in terms such as listing, creating, adding, calculating, comparing, moving, receiving, determining, configuring, identifying, populating, loading, performing, executing, storing etc. that are often associated with manual operations performed by a human operator. The operations described herein can be machine operations performed in conjunction with various input provided by a human operator or user that interacts with the computer.

In addition, it should be understood that the programs, processes, methods, etc. described herein are not related or limited to any particular computer or apparatus. Rather, various types of general purpose machines may be used with the following process in accordance with the teachings described herein.

The present invention may comprise a computer program or hardware or a combination thereof which embodies the functions described herein and illustrated in the appended flow charts. However, it should be apparent that there could be many different ways of implementing the invention in computer programming or hardware design, and the invention should not be construed as limited to any one set of computer program instructions.

Further, a skilled programmer would be able to write such a computer program or identify the appropriate hardware circuits to implement the disclosed invention without difficulty based on the flow charts and associated description in the application text, for example. Therefore, disclosure of a particular set of program code instructions or detailed hardware devices is not considered necessary for an adequate understanding of how to make and use the invention. The inventive functionality of the claimed computer implemented processes will be explained in more detail in the following description.

Further, certain steps in the processes or process flow described in the logic flow diagram must naturally precede others for the present invention to function as described. However, the present invention is not limited to the order of the steps described if such order or sequence does not alter the functionality of the present invention. That is, it is recognized that some steps may be performed before, after, or in parallel other steps without departing from the scope and spirit of the present invention.

Referring again to FIG. 25, Step 2501 is the first step in the process 2500 for monitoring oxygenation levels of a compartment according to one exemplary embodiment of the invention. In step 2501, a compartment sensor 405 may be manufactured from sterile materials as described above in connection with FIG. 21. Alternatively, a compartment sensor 405 can be encapsulated with sterile materials so that it can be used in a surgical environment or so that it can be place adjacent to wounds (or both).

In step 2503, a central scan depth marker 415 can be provided on a compartment sensor 405. In step 2506, an alignment mechanism 410 can also be provided on the compartment sensor 405 to allow a medical practitioner to orient a sensor 405 along a longitudinal axis of a compartment of interest.

In step 2509, an expansion device 535 may be provided between two or more grouped compartment sensors 405 as illustrated in FIG. 5A. In step 2512, the processor and display device 420 may receive input from a user on the type of compartment that is to be monitored by the inventive system 400.

In step 2515 and in response to the input of step 2512, the display device 420 can display a location of the selected compartment of interest such as illustrated in FIG. 14D. The display device 420 can also display the longitudinal axis 450 of the compartment of interest. Next, in step 2518, the display device 420 may display an ideal or optimal position for the compartment sensor 405 along the longitudinal axis of the compartment of interest as illustrated in FIG. 14D.

In step 2521, with the information from steps 2515-2518, the medical practitioner can identify a proper position of the compartment sensor on a patient through orienting the alignment mechanism 410 with the longitudinal axis of the compartment and by using the central scan depth marker 415.

In step 2527, the compartment sensor 405 can be placed on the patient. In step 2530, the compartment sensor can obtain a skin pigment value of the patient's skin through using a skin sensor 1820 as illustrated in FIG. 18C or thorough using a shallow sensor 405 as illustrated in FIG. 17. In step 2533, the processor 420A can determine an oxygenation offset value based on the skin pigment value obtained in step 2530.

Next, in step 2536, the offset value from step 2533 can be used during oxygenation level monitoring. In step 2539, the blood pressure of the patient can be monitored with a probe 440 and blood pressure monitor as illustrated in FIGS. 4 and 19. In step 2542, the system 400 can monitor the oxygenation levels of one or more compartments of interest over time. In step 2545, the system 400 can also monitor the oxygenation levels of healthy compartments to obtain a baseline while monitoring the compartments adjacent to an injury or trauma as illustrated in FIG. 15B.

In step 2547, the oxygenation levels of compartments of interest can be displayed on the display device 420 as illustrated in FIGS. 10, 14C, 15B-C, 16, and 20. In step 2550, the blood pressure of the patient can also be displayed on the display device as illustrated in FIG. 20. In step 2553, the display device 420 and its processor can monitor the relationship between the blood pressure values and oxygenation levels as illustrated in FIG. 20.

In step 2556, the display device 420 can activate an alarm in the form of an audible or visual message (or both), when the oxygenation levels drop below a predetermined value or if a significant change in the levels is detected as illustrated in FIG. 20. In step 2559, the display device can also activate an alarm in the form of an audible or visual message (or both), when both the oxygenation levels and blood pressure drop simultaneously or if one of them falls below a predetermined threshold value as described in connection with FIG. 20.

In step 2562, the display device 420 and its processor can increase a frequency of data collection for oxygenation levels and blood pressure values if both values drop. The exemplary process then ends.

Alternative Exemplary Embodiments

The inventive compartment monitoring system 400 could also be used for free flap as well as tissue transfer monitoring. Currently skin color and capillary refill are used to evaluate flap viability. This practice requires repeated examinations and subjective criteria. The conventional method requires leaving skin exposed or taking down dressings which can be very labor intensive. As a solution to the conventional approach, a sensor 405 can be sterilized and it can record average oxygenation levels over time. The sensor 405 can be placed on the flap (free or transferred).

The compartment sensor 405 can also be used to monitor oxygenation of tissue transferred for vascular patency. Specifically, for hand or any upper extremity surgery, the compartment sensor can be used to monitor the progress of revascularization of fingers, hands and arms based on measured oxygenation levels. The sensor 405 can be applied to the injured extremity once vascular repair has been performed in order to continue monitoring of vascular repair. A baseline of a corresponding uninjured or healthy extremity can be made once repair to the injured extremity is done—before closure—in order to get a baseline value while looking at the repair. Sensors 405 for this application will also need to be sterilized and be able to conduct scans with depths of at least 0.5 centimeters.

It should be understood that the foregoing relates only to illustrate the embodiments of the invention, and that numerous changes may be made therein without departing from the scope and spirit of the invention as defined by the following claims.

| | Compartment Syndrome Patients | | | | | | | | | |
|---|---|---|---|---|---|---|---|---|---|---|
| | Anterior | | | | | Lateral | | | | |
| Pt | Injur | Unin | Diff | ICP | PP | Injur | Unin | Diff | ICP | PP |
| 1 | 66 | 58 | 8 | 78 | −13 | 58 | 65 | −7 | 79 | −14 |
| 2 | 35 | 50 | −15 | 170 | −70 | 41 | 49 | −8 | 176 | −76 |
| 3 | 15 | 41 | −26 | 107 | −37 | 15 | 40 | −25 | 104 | −34 |
| 4 | 46 | 44 | 2 | 72 | 4 | 34 | 49 | −15 | 82 | −6 |
| 5 | 45 | 47 | −2 | 71 | 18 | 53 | 53 | 0 | 71 | 18 |
| 6 | 56 | 64 | −6 | 59 | −4 | 55 | 61 | −6 | 57 | −2 |
| 7 | | | | | | | | | | |
| 8 | 58 | 66 | −8 | 142 | −44 | 51 | 64 | −13 | 142 | −44 |
| 9 | 50 | 51 | −1 | 57 | 1 | | 53 | 54 | −1 | 55 |
| Avg | 46.4 | 52.6 | −6 | 94.5 | −18.1 | 45 | 54.4 | −9.38 | 95.8 | −19.4 |
| Std D | 15.8 | 9.16 | 10.6 | 41.6 | 29.5 | 14.5 | 8.58 | 8.16 | 42.9 | 30.3 |
| pVal | 0.07 | | | | | | 0.01 | | | |
| Rang | 66,15 | 41,66 | 8,−26 | | | | 15,58 | 40,65 | 0,−25 | |

Compartment Syndrome Patients

| | Deep Posterior | | | | | Superficial Posterior | | | | |
|---|---|---|---|---|---|---|---|---|---|---|
| Pt | Injur | Unin | Diff | ICP | PP | Injur | Unin | Diff | ICP | PP |
| 1 | | | | 76 | −11 | 58 | 57 | 1 | 84 | −19 |
| 2 | | | | 116 | −16 | 43 | 67 | −24 | 115 | −15 |
| 3 | | | | 104 | −34 | 47 | 45 | 2 | 99 | −29 |
| 4 | | | | 57 | 19 | 32 | 56 | −24 | 71 | 5 |
| 5 | | | | 56 | 33 | 56 | 55 | 1 | 61 | 28 |
| 6 | 46 | 67 | −21 | 63 | −8 | 55 | 64 | −9 | 62 | −7 |
| 7 | 56 | 61 | −5 | 61 | 10 | 62 | 59 | 3 | 59 | 12 |
| 8 | 59 | 75 | −16 | 135 | −37 | 50 | 77 | −27 | 110 | −12 |
| 9 | | | 3 | | | | | | | |
| Avg | 53.7 | 67.7 | −14 | 83.5 | −5.5 | 50.4 | 60 | −9.63 | 82.6 | −4.63 |
| Std D | 6.81 | 7.02 | 8.19 | 30.6 | 24.7 | 9.64 | 9.49 | 13.3 | 22.8 | 18.5 |
| pVal | | | 0.05 | | | | | 0.04 | | |
| Rang | | | 46,59 | 61,75 | −5,−21 | 32,62 | 45,77 | 3,−27 | | |

Initial Injury Study

Non Compartment Syndrome

| | Anterior | | | Lateral | | | Deep Post | | | Sup Posterior | | |
|---|---|---|---|---|---|---|---|---|---|---|---|---|
| Pt | Injured | Uninjured | Diff | Injured | Uninjured | Diff | Injured | Uninjured | Diff | Injured | Uninjured | Diff |
| 1 | 70 | 65 | 5 | 70 | 58 | 12 | | | | 77 | 68 | 9 |
| 2 | 64 | 54 | 10 | 61 | 56 | 5 | | | | 72 | 57 | 15 |
| 3 | 58 | 47 | 11 | 49 | 44 | 5 | | | | 49 | 43 | 6 |
| 4 | 77 | 63 | 14 | 82 | 66 | 16 | 83 | 61 | 22 | 79 | 66 | 13 |
| 5 | 82 | 58 | 24 | 78 | 59 | 19 | 72 | 63 | 9 | 73 | 56 | 17 |
| 6 | 62 | 54 | 8 | 61 | 53 | 8 | 66 | 49 | 17 | 63 | 51 | 12 |
| 7 | 64 | 48 | 16 | 68 | 46 | 22 | 76 | 52 | 24 | 64 | 44 | 20 |
| 8 | 70 | 62 | 8 | 73 | 57 | 16 | 80 | 59 | 21 | 87 | 64 | 23 |
| 9 | 62 | 47 | 15 | 71 | 53 | 18 | 74 | 52 | 22 | 66 | 53 | 13 |
| 10 | 73 | 60 | 13 | 75 | 52 | 23 | 71 | 52 | 19 | 72 | 56 | 16 |
| 11 | 73 | 58 | 15 | 88 | 51 | 37 | 88 | 62 | 26 | 80 | 52 | 28 |
| 12 | 63 | 53 | 10 | 61 | 50 | 11 | 72 | 57 | 15 | 73 | 61 | 12 |
| 13 | 78 | 73 | 5 | 82 | 75 | 7 | 86 | 70 | 16 | 81 | 71 | 10 |
| 14 | 67 | 57 | 10 | 70 | 62 | 8 | 74 | 64 | 10 | 71 | 62 | 9 |
| 15 | 71 | 46 | 25 | 63 | 43 | 20 | 71 | 43 | 28 | 69 | 46 | 23 |
| 16 | 77 | 47 | 30 | 66 | 55 | 11 | 66 | 54 | 12 | 62 | 57 | 5 |
| 17 | 55 | 46 | 9 | 62 | 48 | 14 | 62 | 51 | 11 | 63 | 45 | 18 |
| 18 | 82 | 58 | 24 | 79 | 64 | 15 | 90 | 75 | 15 | 79 | 74 | 5 |
| 19 | 54 | 49 | 5 | 60 | 47 | 13 | 54 | 52 | 2 | 57 | 50 | 7 |
| 20 | 79 | 71 | 8 | 90 | 81 | 9 | 87 | 72 | 15 | 86 | 69 | 17 |
| 21 | 70 | 49 | 21 | 65 | 47 | 18 | 64 | 45 | 19 | 61 | 52 | 9 |
| 22 | 78 | 44 | 34 | 76 | 43 | 33 | 82 | 54 | 28 | 69 | 48 | 21 |
| 23 | 74 | 65 | 9 | 76 | 63 | 13 | 78 | 61 | 17 | 73 | 65 | 8 |
| 24 | 68 | 53 | 15 | 66 | 56 | 10 | 77 | 58 | 19 | 70 | 55 | 15 |
| 25 | 62 | 51 | 11 | 68 | 53 | 15 | 60 | 51 | 9 | 60 | 50 | 10 |
| 26 | 68 | 53 | 15 | 66 | 56 | 10 | 77 | 58 | 19 | 70 | 55 | 15 |
| Avg | 69.3 | 55 | 14.2 | 70.2 | 55.3 | 14.9 | 74.3 | 57.2 | 17.2 | 70.2 | 56.5 | 13.7 |
| Med | 70 | 53.5 | 12 | 69 | 54 | 13.5 | 74 | 57 | 17 | 70.5 | 55.5 | 13 |
| Std D | 7.93 | 7.94 | 7.75 | 9.47 | 9.27 | 7.69 | 9.48 | 8.14 | 6.5 | 8.99 | 8.72 | 6.03 |
| pVal | 0.000000 | | | 0.000000 | | | 0.000000 | | | 0.000000 | | |

Non Compartment Syndrome 2 Days Post-Op

| | Anterior | | | Lateral | | | Deep Post | | | Sup Posterior | | |
|---|---|---|---|---|---|---|---|---|---|---|---|---|
| Pt | Injured | Uninjured | Diff | Injured | Uninjured | Diff | Injured | Uninjured | Diff | Injured | Uninjured | Diff |
| 1 | 79 | 51 | 28 | 75 | 54 | 21 | 69 | 47 | 22 | 67 | 43 | 24 |
| 2 | 56 | 47 | 9 | 51 | 45 | 6 | 58 | 46 | 12 | 56 | 48 | 8 |
| 3 | 82 | 52 | 30 | 78 | 47 | 31 | 82 | 59 | 23 | 88 | 50 | 38 |
| 4 | 63 | 55 | 8 | 65 | 54 | 11 | 74 | 58 | 16 | 70 | 58 | 12 |
| 5 | 62 | 50 | 12 | 63 | 47 | 16 | 63 | 58 | 5 | 62 | 54 | 8 |
| 6 | 61 | 50 | 11 | 62 | 54 | 8 | 68 | 60 | 8 | 81 | 55 | 26 |
| 7 | 69 | 61 | 8 | 71 | 64 | 7 | 79 | 69 | 10 | 75 | 68 | 7 |
| 8 | 68 | 42 | 26 | 65 | 39 | 26 | 75 | 41 | 34 | 62 | 44 | 18 |
| 9 | 85 | 73 | 12 | 79 | 62 | 17 | 95 | 75 | 20 | 93 | 73 | 20 |
| 10 | 71 | 62 | 9 | 72 | 58 | 14 | 66 | 61 | 5 | 74 | 61 | 13 |
| 11 | 83 | 70 | 13 | 82 | 67 | 15 | 87 | 71 | 16 | 88 | 72 | 16 |
| 12 | 77 | 47 | 30 | 66 | 55 | 11 | 66 | 54 | 12 | 62 | 57 | 5 |
| 13 | 64 | 56 | 8 | 62 | 50 | 12 | 67 | 56 | 11 | 63 | 51 | 12 |

-continued

| | | | | | Initial Injury Study | | | | | | | |
|---|---|---|---|---|---|---|---|---|---|---|---|---|
| 14 | 70 | 49 | 21 | 80 | 55 | 25 | 73 | 63 | 10 | 65 | 54 | 11 |
| 15 | 84 | 64 | 20 | 90 | 63 | 27 | 88 | 64 | 24 | 88 | 63 | 25 |
| 16 | 60 | 47 | 13 | 63 | 51 | 12 | 64 | 51 | 13 | 76 | 43 | 33 |
| 17 | 71 | 63 | 8 | 61 | 57 | 4 | 87 | 62 | 25 | 63 | 60 | 3 |
| Avg | 70.9 | 55.2 | 15.6 | 69.7 | 54.2 | 15.5 | 74.2 | 58.5 | 15.6 | 72.5 | 56.1 | 16.4 |
| Med | 70 | 52 | 12 | 66 | 54 | 14 | 73 | 59 | 13 | 70 | 55 | 13 |
| Std D | 9.3 | 8.84 | 8.31 | 9.85 | 7.37 | 8 | 10.5 | 8.97 | 7.95 | 11.5 | 9.35 | 10 |
| pVal | 0.00000 | | | 0.00000 | | | 0.00000 | | | 0.00000 | | |

| | Uninjured Subjects (Normal NIRS Values) | | | | | | | | | | | | | | | |
|---|---|---|---|---|---|---|---|---|---|---|---|---|---|---|---|---|
| | Anterior | | | | Lateral | | | | Deep Post | | | | Sup Posterior | | | |
| Pt | R | L | Diff | AV | R | L | Diff | AV | R | L | Diff | AV | R | L | Diff | AV |
| 1 | 50 | 46 | 4 | 4 | 46 | 48 | −2 | 2 | 48 | 49 | −1 | 1 | 40 | 40 | 0 | 0 |
| 2 | 58 | 56 | 2 | 2 | 60 | 60 | 0 | 0 | 63 | 60 | 3 | 3 | 64 | 57 | 7 | 7 |
| 3 | 49 | 47 | 2 | 2 | 48 | 50 | −2 | 2 | 47 | 44 | 3 | 3 | 47 | 44 | 3 | 3 |
| 4 | 59 | 60 | −1 | 1 | 60 | 57 | 3 | 3 | 58 | 61 | −3 | 3 | 58 | 61 | −3 | 3 |
| 5 | 54 | 51 | 3 | 3 | 51 | 48 | 3 | 3 | 55 | 51 | 4 | 4 | 55 | 52 | 3 | 3 |
| 6 | 55 | 52 | 3 | 3 | 58 | 53 | 5 | 5 | 68 | 65 | 3 | 3 | 69 | 63 | 6 | 6 |
| 7 | 56 | 57 | −1 | 1 | 52 | 58 | −6 | 6 | 52 | 62 | −10 | 10 | 64 | 67 | −3 | 3 |
| 8 | 54 | 57 | −3 | 3 | 56 | 57 | −1 | 1 | 61 | 61 | 0 | 0 | 55 | 60 | −5 | 5 |
| 9 | 49 | 42 | 7 | 7 | 50 | 43 | 7 | 7 | 55 | 49 | 6 | 6 | 52 | 52 | 0 | 0 |
| 10 | 48 | 44 | 4 | 4 | 51 | 46 | 5 | 5 | 72 | 60 | 12 | 12 | 51 | 46 | 5 | 5 |
| 11 | 71 | 65 | 6 | 6 | 73 | 68 | 5 | 5 | 75 | 76 | −1 | 1 | 69 | 75 | −6 | 6 |
| 12 | 48 | 50 | −2 | 2 | 48 | 53 | −5 | 5 | 49 | 54 | −5 | 5 | 47 | 49 | −2 | 2 |
| 13 | 45 | 50 | −5 | 5 | 46 | 51 | −5 | 5 | 47 | 46 | 1 | 1 | 54 | 53 | 1 | 1 |
| 14 | 59 | 51 | 8 | 8 | 60 | 52 | 8 | 8 | 59 | 55 | 4 | 4 | 61 | 57 | 4 | 4 |
| 15 | 48 | 56 | −8 | 8 | 50 | 55 | −5 | 5 | 56 | 58 | −2 | 2 | 49 | 55 | −6 | 6 |
| 16 | 42 | 43 | −1 | 1 | 44 | 43 | 1 | 1 | 43 | 42 | 1 | 1 | 46 | 37 | 9 | 9 |
| 17 | 54 | 56 | −2 | 2 | 55 | 60 | −5 | 5 | 64 | 60 | 4 | 4 | 67 | 62 | 5 | 5 |
| 18 | 54 | 54 | 0 | 0 | 51 | 47 | 4 | 4 | 52 | 54 | −2 | 2 | 59 | 53 | 6 | 6 |
| 19 | 42 | 43 | −1 | 1 | 48 | 42 | 6 | 6 | 52 | 47 | 5 | 5 | 42 | 48 | −6 | 6 |
| 20 | 68 | 65 | 3 | 3 | 70 | 67 | 3 | 3 | 73 | 68 | 5 | 5 | 74 | 71 | 3 | 3 |
| 21 | 62 | 61 | 1 | 1 | 61 | 55 | 6 | 6 | 68 | 67 | 1 | 1 | 68 | 70 | −2 | 2 |
| 22 | 49 | 46 | 3 | 3 | 52 | 48 | 4 | 4 | 66 | 55 | 11 | 11 | 64 | 66 | −2 | 2 |
| 23 | 67 | 62 | 5 | 5 | 70 | 65 | 5 | 5 | 88 | 81 | 7 | 7 | 77 | 70 | 7 | 7 |
| 24 | 74 | 68 | 6 | 6 | 74 | 69 | 5 | 5 | 68 | 65 | 3 | 3 | 76 | 67 | 9 | 9 |
| 25 | 66 | 64 | 2 | 2 | 74 | 71 | 3 | 3 | 70 | 71 | −1 | 1 | 71 | 66 | 5 | 5 |
| Avg | 55.2 | 53.8 | 1.4 | 3.32 | 56.3 | 54.6 | 1.68 | 4.16 | 60.4 | 58.4 | 1.92 | 3.92 | 59.2 | 57.6 | 1.52 | 4.32 |
| T avg | 54.5 | | | | 55.5 | | | | 59.4 | | | | 58.4 | | | |
| Std D | 8.81 | 7.73 | 3.83 | 2.29 | 9.4 | 8.5 | 4.35 | 1.95 | 10.9 | 9.83 | 4.74 | 3.21 | 10.8 | 10.2 | 4.81 | 2.48 |

| | White vs. Dark Pigmented Skin Comparison | | | | | | | | | | | | | | | |
|---|---|---|---|---|---|---|---|---|---|---|---|---|---|---|---|---|
| | African American | | | | | | | | | | | | | | | |
| | Anterior | | | | Lateral | | | | Deep Post | | | | Sup Posterior | | | |
| Pt | R | L | Diff | AV | R | L | Diff | AV | R | L | Diff | AV | R | L | Diff | AV |
| 1 | 50 | 46 | 4 | 4 | 46 | 48 | −2 | 2 | 48 | 49 | −1 | 1 | 40 | 40 | 0 | 0 |
| 3 | 49 | 47 | 2 | 2 | 48 | 50 | −2 | 2 | 47 | 44 | 3 | 3 | 47 | 44 | 3 | 3 |
| 7 | 56 | 57 | −1 | 1 | 52 | 58 | −6 | 6 | 52 | 62 | −10 | 10 | 64 | 67 | −3 | 3 |
| 8 | 54 | 57 | −3 | 3 | 56 | 57 | −1 | 1 | 61 | 61 | 0 | 0 | 55 | 60 | −5 | 5 |
| 9 | 49 | 42 | 7 | 7 | 50 | 43 | 7 | 7 | 55 | 49 | 6 | 6 | 52 | 52 | 0 | 0 |
| 10 | 48 | 44 | 4 | 4 | 51 | 46 | 5 | 5 | 72 | 60 | 12 | 12 | 51 | 46 | 5 | 5 |
| 11 | 71 | 65 | 6 | 6 | 73 | 68 | 5 | 5 | 75 | 76 | −1 | 1 | 69 | 75 | −6 | 6 |
| 12 | 48 | 50 | −2 | 2 | 48 | 53 | −5 | 5 | 49 | 54 | −5 | 5 | 47 | 49 | −2 | 2 |
| 13 | 45 | 50 | −5 | 5 | 46 | 51 | −5 | 5 | 47 | 46 | 1 | 1 | 54 | 53 | 1 | 1 |
| 14 | 59 | 51 | 8 | 8 | 60 | 52 | 8 | 8 | 59 | 55 | 4 | 4 | 61 | 57 | 4 | 4 |
| 15 | 48 | 56 | −8 | 8 | 50 | 55 | −5 | 5 | 56 | 58 | −2 | 2 | 49 | 55 | −6 | 6 |
| 16 | 42 | 43 | −1 | 1 | 44 | 43 | 1 | 1 | 43 | 42 | 1 | 1 | 46 | 37 | 9 | 9 |
| 17 | 54 | 56 | −2 | 2 | 55 | 60 | −5 | 5 | 64 | 60 | 4 | 4 | 67 | 62 | 5 | 5 |
| 18 | 54 | 54 | 0 | 0 | 51 | 47 | 4 | 4 | 52 | 54 | −2 | 2 | 59 | 53 | 6 | 6 |
| 19 | 42 | 43 | −1 | 1 | 48 | 42 | 6 | 6 | 52 | 47 | 5 | 5 | 42 | 48 | −6 | 6 |

-continued

| | | | | | White vs. Dark Pigmented Skin Comparison | | | | | | | | | | |
|---|---|---|---|---|---|---|---|---|---|---|---|---|---|---|---|
| 26 | 49 | 46 | 3 | 3 | 49 | 48 | 1 | 1 | 42 | 41 | 1 | 1 | 44 | 42 | 2 | 2 |
| 27 | 60 | 53 | 7 | 7 | 52 | 54 | −2 | 2 | 42 | 48 | −6 | 6 | 46 | 46 | 0 | 0 |
| Avg | 51.3 51 | 50.7 | 0.53 | 51.9 | 51.5 51.7 | 0.33 | | 1 | 55.5 55 | 53.5 | 53.2 | 0.33 | 53.4 | | | |

| | | Anterior | | | | Lateral | | | | Deep Post | | | | Sup Posterior | | |
|---|---|---|---|---|---|---|---|---|---|---|---|---|---|---|---|---|
| | | | | | | White | | | | | | | | | | |
| Pt | R | L | Diff | AV | R | L | Diff | AV | R | L | Diff | AV | R | L | Diff | AV |
| 2 | 58 | 56 | 2 | 2 | 60 | 60 | 0 | 0 | 63 | 60 | 3 | 3 | 64 | 57 | 7 | 7 |
| 4 | 59 | 60 | −1 | 1 | 60 | 57 | 3 | 3 | 58 | 61 | −3 | 3 | 58 | 61 | −3 | 3 |
| 5 | 54 | 51 | 3 | 3 | 51 | 48 | 3 | 3 | 55 | 51 | 4 | 4 | 55 | 52 | 3 | 3 |
| 6 | 55 | 52 | 3 | 3 | 58 | 53 | 5 | 5 | 68 | 65 | 3 | 3 | 69 | 63 | 6 | 6 |
| 20 | 68 | 65 | 3 | 3 | 70 | 67 | 3 | 3 | 73 | 68 | 5 | 5 | 74 | 71 | 3 | 3 |
| 21 | 62 | 61 | 1 | 1 | 61 | 55 | 6 | 6 | 68 | 67 | 1 | 1 | 68 | 70 | −2 | 2 |
| 22 | 49 | 46 | 3 | 3 | 52 | 48 | 4 | 4 | 66 | 55 | 11 | 11 | 64 | 66 | −2 | 2 |
| 23 | 67 | 62 | 5 | 5 | 70 | 65 | 5 | 5 | 88 | 81 | 7 | 7 | 77 | 70 | 7 | 7 |
| 24 | 74 | 68 | 6 | 6 | 74 | 69 | 5 | 5 | 68 | 65 | 3 | 3 | 76 | 67 | 9 | 9 |
| 25 | 66 | 64 | 2 | 2 | 74 | 71 | 3 | 3 | 70 | 71 | −1 | 1 | 71 | 66 | 5 | 5 |
| Avg | 61.2 59.9 | 58.5 | 2.7 | 2.9 | 63 61.2 | 59.3 | 3.7 | 3.7 | 67.7 66.1 | 64.4 | 3.3 | 4.1 | 67.6 66 | 64.3 | 3.3 | 4.7 |
| Diff | 8.85 | | | | 9.45 | | | | 11.1 | | | | 12.6 | | | |
| Test | 0.000070 | | | | 0.000091 | | | | 0.000068 | | | | 0.000005 | | | |

| | | | | | | | Compartment Syndrome Patients Demographics | | | | | | |
|---|---|---|---|---|---|---|---|---|---|---|---|---|---|
| Pt | Diast | Early | Late | Fx | Location | Mech | Time p Injured | Ht | Wt | BMI | Side | Sex | Race | Age |
| 1 | 65 | 1 | | T/F | P | MVC | 6 | 66 | 165 | 26.629 | L | M | B | 15 |
| 2 | 100 | | 1 | T/F | M | PvA | 8 | 68 | 210 | 31.927 | R | M | B | 22 |
| 3 | 70 | | 1 | T/F | P | GSW | 5 | 73 | 170 | 22.426 | L | M | B | 19 |
| 4 | 76 | | 1 | T/F | M | PvA | 10 | 71 | 165 | 23.01 | R | M | B | 59 |
| 5 | 89 | 1 | | P | | MVC | 4 | 74 | 220 | 28.243 | L | M | B | 59 |
| 6 | 55 | | 1 | P | | MVC | 10 | 69 | 210 | 31.008 | L | M | B | 23 |
| 7 | 71 | 1 | | P | | Fall | 28 | 67 | 155 | 24.274 | L | M | W | 44 |
| 8 | 98 | | 1 | P | | Fall | 6 | 68 | 200 | 30.407 | L | M | H | 32 |
| 9 | 58 | 1 | | T/F | M | MVC | 13 | 66 | 150 | 24.208 | L | M | A | 62 |
| Avg | 75.8 | | | | | | 10 | 69.111 | 182.78 | 26.904 | | | | 37.222 |
| Std D | 16.5 | | | | | | 7.3314 | 2.9345 | 26.939 | 3.6333 | | | | 19.025 |

| | | | | | | | | | Initial Injury Study | | | | | | | | | |
|---|---|---|---|---|---|---|---|---|---|---|---|---|---|---|---|---|---|---|
| | | | | | | | | | Non Compartment Syndrome Demographics | | | | | | | | | |
| Pt | Mech | Ht | Wt | BMI | Side | Sex | Race | Age | %O2 | Time injur | Time p op | Syst | Diast | Fx | Open | Tsch | Location |
| 1 | MVC | 71 | 185 | 25.799 | R | M | B | 18 | 0 | 12 | | | | T/F | | 1 | M |
| 2 | MVC | 60 | 165 | 32.221 | R | F | B | 45 | 0 | 52 | | | | T/F | | 2 | M |
| 3 | MVC | 68 | 202 | 30.711 | R | F | B | 35 | 0 | 7 | | | | T/F | 3A | 3 | M |
| 4 | MVC | 67 | 230 | 36.019 | R | M | W | 45 | 0 | 10 | | 123 | 67 | T/F | | 2 | M |
| 5 | MVC | 67 | 130 | 20.359 | L | M | B | 45 | 0 | 31 | | 125 | 56 | T/F | | 1 | M |
| 6 | Fall | 72 | 205 | 27.8 | R | M | W | 18 | 0 | 15 | | 134 | 79 | SchVI | | 2 | P |
| 7 | Fall | 69 | 161 | 23.773 | R | M | B | 60 | 0 | 16 | | 120 | 69 | Pilon | | 2 | D |
| 8 | PvA | 71 | 170 | 23.708 | L | M | W | 26 | 0 | 11 | | 129 | 76 | T/F | | 2 | M |
| 9 | Fall | 67 | 215 | 33.67 | R | M | B | 31 | 0 | 18 | | 141 | 59 | T/F | | 1 | D |
| 10 | Fall | 66 | 195 | 31.47 | R | M | B | 45 | 0 | 5 | | 151 | 95 | Pilon | | 2 | D |
| 11 | MVC | 67 | 140 | 21.925 | L | M | B | 30 | 0 | 48 | | 117 | 58 | Pilon | | 3 | P |
| 12 | MVC | 72 | 210 | 28.478 | R | M | B | 52 | 0 | 9 | | 183 | 113 | T/F | 1 | 2 | D |
| 13 | MVC | 66 | 175 | 28.243 | L | F | W | 55 | 0 | 12 | | 106 | 58 | T/F | 3A | 3 | M |
| 14 | MVC | 73 | 280 | 36.938 | R | M | B | 46 | 0 | 17 | | 129 | 65 | T/F | | 2 | P |
| 15 | Fall | 67 | 155 | 24.274 | L | M | W | 27 | 0 | 14 | | 133 | 76 | T/F | | 3 | M |
| 16 | Fall | 73 | 205 | 27.044 | L | M | B | 44 | 0 | 2 | | 114 | 60 | T/F | 2 | 2 | P |
| 17 | MVC | 72 | 175 | 23.732 | R | M | W | 28 | 100 | 8 | | 80 | 24 | T/F | | 1 | M |
| 18 | MVC | 75 | 345 | 43.117 | R | F | B | 21 | 0 | 14 | | 131 | 85 | SchV | | 2 | D |
| 19 | MVC | 68 | 175 | 26.606 | R | M | W | 42 | 0 | 9 | | 163 | 88 | Pilon | 2 | 2 | D |
| 20 | MVC | 70 | 190 | 27.259 | R | M | B | 42 | 0 | 21 | | 153 | 93 | Pilon | 2 | 3 | M |
| 21 | PvA | 70 | 170 | 24.39 | R | M | W | 22 | 0 | 32 | | 140 | 75 | T/F | 3A | 2 | M |
| 22 | PvA | 68 | 168 | 25.542 | L | M | B | 54 | 100 | 2 | | 131 | 78 | T/F | | 3 | M |
| 23 | Blow | 71 | 195 | 27.194 | L | M | H | 38 | 0 | 19 | | 137 | 67 | T/F | | 1 | P |
| 24 | MVC | 68 | 165 | 25.085 | R | M | B | 29 | 0 | 13 | | 148 | 87 | SchV | | 2 | M |
| 25 | MVC | 64 | 210 | 36.042 | L | F | B | 26 | 0 | 5 | | 123 | 49 | T/F | | 1 | P |
| 26 | MVC | 68 | 165 | 25.085 | L | M | B | 23 | 2 | 13 | | 148 | 87 | SchV | | 2 | P |
| Avg | | 68.8 | 191.58 | 28.326 | 10-L | 5 | 8 | 35.692 | | 15.962 | | 133 | 72.348 | 3-Plat | 7 | 7-1's | 5-P |
| Med | | | | | 15-R | 20 | 17 | | | | | | | 17-T/F | | 13-2's | 14-M |
| Std D | | 3.21 | 43.706 | 5.3403 | | | | 12.315 | | 12.389 | | 20.596 | 18.527 | 5-pilon | | 5-3's | 6-D |
| pVal | | | | | | | | | | | | | | | | | |

| | | | | | | | | Non Compartment Syndrome 2 Days Post-Op Demographics | | | | | | | | | |
|---|---|---|---|---|---|---|---|---|---|---|---|---|---|---|---|---|---|
| Pt | Mech | Ht | Wt | BMI | Side | Sex | Race | Age | Surgery | Time injur | Time p op | Syst | Diast | Fx | Open | Tsch | Location |
| 1 | GSW | 71 | 212 | 29.565 | L | M | B | 32 | IMN | 60 | 36 | 148 | 84 | T/F | 3 | M | |
| 2 | PvA | 69 | 175 | 25.84 | R | M | H | 34 | IMN | 130 | 119 | 116 | 65 | T/F | 3A | 3 | M |
| 3 | MVC | 67 | 130 | 20.359 | L | M | B | 18 | IMN | 75 | 43 | 135 | 73 | T/F | 1 | M | |
| 4 | Fall | 72 | 205 | 27.8 | R | M | W | 60 | ExF | 48 | 35 | 101 | 57 | SkVI | 2 | P | |
| 5 | MVC | 74 | 200 | 25.676 | R | M | B | 48 | ORIF | 96 | 45 | 148 | 103 | F | 2 | 1 | D |
| 6 | Fall | 69 | 161 | 23.773 | L | F | W | 26 | ORIF | 133 | 40 | 134 | 77 | Pilon | 2 | D | |
| 7 | PvA | 62 | 115 | 21.031 | L | F | W | 22 | ORIF | 90 | 44 | 107 | 67 | Pilon | 1 | D | |
| 8 | PvA | 75 | 170 | 21.246 | R | M | B | 47 | IMN | 43 | 31 | 131 | 86 | T/F | 2 | 2 | M |
| 9 | Fall | 64 | 170 | 29.177 | R | F | W | 51 | ExF | 47 | 41 | 144 | 79 | Pilon | 2 | D | |
| 10 | PvA | 71 | 170 | 23.708 | L | M | W | 31 | IMN | 82 | 40 | 148 | 84 | T/F | 1 | M | |
| 11 | MVC | 66 | 175 | 28.243 | R | F | W | 46 | IMN | 60 | 42 | 112 | 61 | T/F | 3A | 3 | M |

-continued

| | | | | | | | | | | Initial Injury Study | | | | | |
|---|---|---|---|---|---|---|---|---|---|---|---|---|---|---|---|
| 12 | Fall | 73 | 205 | 27.044 | L | M | B | 28 | IMN | 42 | 32 | 135 | 71 | T/F | 2 | 3 | M |
| 13 | MVC | 68 | 175 | 26.606 | R | F | B | 42 | ExF | 64 | 37 | 122 | 79 | Pilon | 1 | D | |
| 14 | PvA | 70 | 170 | 24.39 | R | M | B | 54 | ExF | 56 | 33 | 119 | 55 | T/F | 3A | 3 | M |
| 15 | MVC | 70 | 190 | 27.259 | R | M | W | 22 | ExF | 58 | 46 | 105 | 68 | T/F | 2 | 3 | D |
| 16 | PvA | 68 | 168 | 25.542 | L | M | B | 38 | IMN | 53 | 42 | 115 | 65 | T/F | 3 | m | |
| 17 | MVC | 68 | 165 | 25.085 | L | M | B | 26 | ExF | 87 | 27 | 137 | 85 | SchV | 2 | P | |
| Avg | | 69.2 | 173.88 | 25.432 | | | | 36.765 | | 72 | 43.118 | 126.88 | 74.059 | | | | |
| Med | | | | | | | | | | | | | | | | | |
| Std D | 3.4 | 25.085 | 2.7582 | | | | 12.612 | | 27.868 | 20.285 | 15.898 | 12.351 | | | | | |
| pVal | | | | | | | | | | | | | | | | | |

| | | | | | | | | Time p Inj | | |
|---|---|---|---|---|---|---|---|---|---|---|
| Pt | Ht | Wt | BMI | Sex | Race | Age | Injury | wk | Syst | Diast |

Uninjured Subjects (Normal NIRS Values) Demographics

| Pt | Ht | Wt | BMI | Sex | Race | Age | Injury | Time p Inj wk | Syst | Diast |
|---|---|---|---|---|---|---|---|---|---|---|
| 1 | 64 | 130 | 22.312 | F | B | 18 | none | | 108 | 67 |
| 2 | 72 | 175 | 23.732 | M | W | 28 | none | | 117 | 65 |
| 3 | 69 | 180 | 26.578 | M | B | 33 | fing Fx | 10 | 139 | 87 |
| 4 | 67 | 185 | 28.972 | M | W | 36 | none | | 124 | 78 |
| 5 | 60 | 110 | 21.481 | F | H | 28 | none | | 124 | 78 |
| 6 | 70 | 175 | 25.107 | M | W | 32 | none | | 125 | 71 |
| 7 | 66 | 200 | 32.277 | M | B | 29 | none | | 144 | 92 |
| 8 | 68 | 200 | 30.407 | M | B | 32 | none | | 125 | 65 |
| 9 | 68 | 188 | 28.582 | M | B | 58 | none | | 150 | 81 |
| 10 | 69 | 192 | 28.35 | M | B | 48 | Clav fx | 6 | 149 | 51 |
| 11 | 66 | 200 | 32.277 | F | B | 58 | none | | 143 | 81 |
| 12 | 71 | 180 | 25.102 | M | B | 28 | none | | 125 | 85 |
| 13 | 66 | 142 | 22.917 | F | B | 34 | none | | 126 | 89 |
| 14 | 62 | 196 | 35.845 | F | B | 24 | none | | 124 | 75 |
| 15 | 69 | 186 | 27.464 | F | B | 42 | none | | 132 | 90 |
| 16 | 63 | 138 | 24.443 | M | B | 39 | none | | 119 | 70 |
| 17 | 57 | 132 | 28.561 | F | B | 43 | none | | 151 | 91 |
| 18 | 71 | 175 | 24.405 | M | B | 21 | none | | 123 | 68 |
| 19 | 69 | 160 | 23.625 | M | B | 21 | none | | 133 | 78 |
| 20 | 76 | 265 | 32.253 | M | W | 26 | none | | 144 | 87 |
| 21 | 67 | 160 | 25.057 | M | W | 25 | none | | 146 | 70 |
| 22 | 63 | 117 | 20.723 | F | W | 51 | none | | 120 | 73 |
| 23 | 74 | 230 | 29.527 | M | W | 32 | none | | 123 | 69 |
| 24 | 72 | 195 | 26.444 | M | W | 33 | none | | 118 | 77 |
| 25 | 72 | 205 | 27.8 | M | W | 23 | none | | 124 | 98 |
| Avg | 67.6 | 176.64 | 26.97 | | | 33.68 | | 8 | 130.24 | 77.44 |
| T avg | | | | | | | | | | |
| Std D | 4.43 | 35.222 | 3.7986 | | | 11.022 | | 2.8284 | 12.011 | 10.863 |

White vs. Dark Pigmented Skin Comparison Demographics

*African American*

| Pt | Ht | Wt | BMI | Sex | Race | Age | Injury | Time p Inj wk | Syst | Diast |
|---|---|---|---|---|---|---|---|---|---|---|
| 1 | 64 | 130 | 22.312 | F | B | 18 | none | | 108 | 67 |
| 3 | 69 | 180 | 26.578 | M | B | 33 | fing Fx | 10 | 139 | 87 |
| 7 | 66 | 200 | 32.277 | M | B | 29 | none | | 144 | 92 |
| 8 | 68 | 200 | 30.407 | M | B | 32 | none | | 125 | 65 |
| 9 | 68 | 188 | 28.582 | M | B | 58 | none | | 150 | 81 |
| 10 | 69 | 192 | 28.35 | M | B | 48 | Clav fx | 6 | 149 | 51 |
| 11 | 66 | 200 | 32.277 | F | B | 58 | none | | 143 | 81 |
| 12 | 71 | 180 | 25.102 | M | B | 28 | none | | 125 | 85 |
| 13 | 66 | 142 | 22.917 | F | B | 34 | none | | 126 | 89 |
| 14 | 62 | 196 | 35.845 | F | B | 24 | none | | 124 | 75 |
| 15 | 69 | 186 | 27.464 | F | B | 42 | none | | 132 | 90 |
| 16 | 63 | 138 | 24.443 | M | B | 39 | none | | 119 | 70 |
| 17 | 57 | 132 | 28.561 | F | B | 43 | none | | 151 | 91 |
| 18 | 71 | 175 | 24.405 | M | B | 21 | none | | 123 | 68 |
| 19 | 69 | 160 | 23.625 | M | B | 21 | none | | 133 | 78 |
| 5 | 69 | 150 | 22.149 | M | H | 24 | ROH arm | 2 | 120 | 80 |
| 8 | 63 | 98 | 17.358 | F | B | 25 | MC fx | 2 | 120 | 81 |
| Avg | 66.5 | 173.27 | 27.543 | | | | | | 132.73 | 78 |

*White*

| Pt | Ht | Wt | BMI | Sex | Race | Age | Injury | Time p Inj wk | Syst | Diast |
|---|---|---|---|---|---|---|---|---|---|---|
| 2 | 72 | 175 | 23.732 | M | W | 28 | none | | 117 | 65 |
| 4 | 67 | 185 | 28.972 | M | W | 36 | none | | 124 | 78 |
| 5 | 60 | 110 | 21.481 | F | H | 28 | none | | 124 | 78 |
| 6 | 70 | 175 | 25.107 | M | W | 32 | none | | 125 | 71 |
| 20 | 76 | 265 | 32.253 | M | W | 26 | none | | 144 | 87 |
| 21 | 67 | 160 | 25.057 | M | W | 25 | none | | 146 | 70 |
| 22 | 63 | 117 | 20.723 | F | W | 51 | none | | 120 | 73 |
| 23 | 74 | 230 | 29.527 | M | W | 32 | none | | 123 | 69 |
| 24 | 72 | 195 | 26.444 | M | W | 33 | none | | 118 | 77 |
| 25 | 72 | 205 | 27.8 | M | W | 23 | none | | 124 | 98 |
| Avg | 69.3 | 181.7 | 26.11 | | | | | | 126.5 | 76.6 |
| Diff | | | | | | | | | | |
| Test | | | | | | | | | | |

APPENDIX B

Tourniquet Study Data

| Subject | INVOS | Perfusion pressure | INVOS Diff from Baseline (PP) |
|---|---|---|---|
| 1 | 67 | 71 | 0 |
|   | 69 | 65 | 2 |
|   | 63 | 56 | −4 |
|   | 62 | 36 | −5 |
|   | 61 | 26 | −6 |
|   | 59 | 17 | −8 |
|   | 56 | 5 | −11 |
|   | 55 | −1 | −12 |
|   | 31 | −11 | −36 |
|   | 16 | −21 | −51 |
|   | 15 | −35 | −52 |
| 2 | 65 | 88 | 0 |
|   | 66 | 75 | 1 |
|   | 64 | 63 | −1 |
|   | 63 | 58 | −2 |
|   | 57 | 48 | −8 |
|   | 58 | 43 | −7 |
|   | 60 | 35 | −5 |
|   | 60 | 15 | −5 |
|   | 58 | 4 | −7 |
|   | 53 | −13 | −12 |
|   | 28 | 0 | −37 |
|   | 20 | −34 | −45 |
| 3 | 63 | 74 | 0 |
|   | 66 | 59 | 3 |
|   | 67 | 49 | 4 |
|   | 65 | 42 | 2 |
|   | 66 | 27 | 3 |
|   | 65 | 15 | 2 |
|   | 64 | 10 | 1 |
|   | 61 | 2 | −2 |
|   | 58 | −11 | −5 |
|   | 52 | −6 | −11 |
|   | 33 | −28 | −30 |
|   | 20 | −34 | −43 |
| 4 | 72 | 71 | 0 |
|   | 79 | 60 | 7 |
|   | 74 | 48 | 2 |
|   | 71 | 41 | −1 |
|   | 71 | 32 | −1 |
|   | 73 | 21 | 1 |
|   | 71 | 20 | −1 |
|   | 70 | 5 | −2 |
|   | 68 | −9 | −4 |
|   | 65 | −13 | −7 |
|   | 63 | −26 | −9 |
|   | 47 | −32 | −25 |
|   | 39 | −46 | −33 |
| 5 | 69 | 86 | 0 |
|   | 70 | 73 | 1 |
|   | 72 | 59 | 3 |
|   | 69 | 55 | 0 |
|   | 69 | 43 | 0 |
|   | 66 | 32 | −3 |
|   | 66 | 20 | −3 |
|   | 64 | 13 | −5 |
|   | 62 | −1 | −7 |
|   | 59 | −7 | −10 |
|   | 35 | −20 | −34 |
|   | 22 | −31 | −47 |
| 6 | 58 | 72 | 0 |
|   | 60 | 59 | 2 |
|   | 58 | 49 | 0 |
|   | 61 | 39 | 3 |
|   | 58 | 27 | 0 |
|   | 58 | 19 | 0 |
|   | 57 | 6 | −1 |
|   | 53 | −4 | −5 |
|   | 48 | −14 | −10 |
|   | 23 | −25 | −35 |
|   | 15 | −31 | −43 |
| 7 | 67 | 73 | 0 |
|   | 68 | 64 | 1 |
|   | 68 | 64 | 1 |
|   | 68 | 44 | 1 |
|   | 68 | 28 | 1 |
|   | 66 | 27 | −1 |
|   | 65 | 9 | −2 |
|   | 63 | 4 | −4 |
|   | 61 | −7 | −6 |
|   | 46 | −18 | −21 |
|   | 15 | −25 | −52 |
| 8 | 65 | 54 | 0 |
|   | 65 | 40 | 0 |
|   | 64 | 26 | −1 |
|   | 63 | 15 | −2 |
|   | 62 | 4 | −3 |
|   | 59 | 1 | −6 |
|   | 41 | −10 | −24 |
|   | 24 | −19 | −41 |
|   | 16 | −26 | −49 |
| 9 | 68 | 67 | 0 |
|   | 71 | 59 | 3 |
|   | 70 | 47 | 2 |
|   | 67 | 41 | −1 |
|   | 65 | 27 | −3 |
|   | 64 | 19 | −4 |
|   | 64 | 10 | −4 |
|   | 63 | −4 | −5 |
|   | 61 | −8 | −7 |
|   | 51 | −18 | −17 |
|   | 24 | −23 | −44 |
|   | 15 | −40 | −53 |
| 10 | 69 | 69 | 0 |
|    | 66 | 57 | −3 |
|    | 62 | 46 | −7 |
|    | 64 | 39 | −5 |
|    | 64 | 27 | −5 |
|    | 63 | 17 | −6 |
|    | 61 | 5 | −8 |
|    | 62 | −1 | −7 |
|    | 57 | −13 | −12 |
|    | 53 | −23 | −16 |
|    | 39 | −33 | −30 |
|    | 33 | −38 | −36 |
| 11 | 62 | 67 | 0 |
|    | 60 | 55 | −2 |
|    | 60 | 45 | −2 |
|    | 58 | 33 | −4 |
|    | 58 | 29 | −4 |
|    | 53 | 15 | −9 |
|    | 52 | 4 | −10 |
|    | 43 | −5 | −19 |
|    | 20 | −12 | −42 |
|    | 15 | −21 | −47 |
| 12 | 71 | 66 | 0 |
|    | 69 | 57 | −2 |
|    | 68 | 49 | −3 |
|    | 64 | 42 | −7 |
|    | 65 | 29 | −6 |
|    | 62 | 28 | −9 |
|    | 61 | 12 | −10 |
|    | 58 | −1 | −13 |
|    | 50 | −9 | −21 |
|    | 40 | −17 | −31 |
|    | 28 | −26 | −43 |
|    | 24 | −37 | −47 |
| 13 | 67 | 69 | 0 |
|    | 69 | 59 | 2 |
|    | 67 | 48 | 0 |
|    | 68 | 41 | 1 |
|    | 65 | 28 | −2 |
|    | 64 | 21 | −3 |
|    | 63 | 8 | −4 |
|    | 63 | 5 | −4 |
|    | 57 | −9 | −10 |

APPENDIX B-continued

Tourniquet Study Data

| Subject | INVOS | Perfusion pressure | INVOS Diff from Baseline (PP) |
|---|---|---|---|
|  | 50 | −21 | −17 |
|  | 23 | −26 | −44 |
|  | 15 | −37 | −52 |
| 14 | 67 | 68 | 0 |
|  | 68 | 53 | 1 |
|  | 65 | 45 | −2 |
|  | 64 | 35 | −3 |
|  | 63 | 21 | −4 |
|  | 63 | 16 | −4 |
|  | 61 | 5 | −6 |
|  | 59 | −3 | −8 |
|  | 54 | −13 | −13 |
|  | 40 | −23 | −27 |
|  | 34 | −35 | −33 |
|  | 33 | −38 | −34 |
| 15 | 70 | 52 | 0 |
|  | 70 | 43 | 0 |
|  | 70 | 29 | 0 |
|  | 69 | 19 | −1 |
|  | 68 | 10 | −2 |
|  | 65 | 2 | −5 |
|  | 59 | −10 | −11 |
|  | 42 | −16 | −28 |
|  | 36 | −27 | −34 |
|  | 34 | −35 | −36 |
|  | 33 | −35 | −37 |
| 16 | 72 | 77 | 0 |
|  | 71 | 63 | −1 |
|  | 68 | 49 | −4 |
|  | 68 | 45 | −4 |
|  | 66 | 27 | −6 |
|  | 66 | 24 | −6 |
|  | 63 | 9 | −9 |
|  | 60 | −3 | −12 |
|  | 53 | −7 | −19 |
|  | 45 | −25 | −27 |
|  | 40 | −28 | −32 |
|  | 38 | −34 | −34 |
| 17 | 61 | 76 | 0 |
|  | 59 | 66 | −2 |
|  | 58 | 59 | −3 |
|  | 61 | 50 | 0 |
|  | 59 | 37 | −2 |
|  | 58 | 29 | −3 |
|  | 58 | 19 | −3 |
|  | 59 | 12 | −2 |
|  | 55 | 10 | −6 |
|  | 45 | −9 | −16 |
|  | 24 | −19 | −37 |
| 18 | 74 | 69 | 0 |
|  | 74 | 61 | 0 |
|  | 73 | 48 | −1 |
|  | 73 | 39 | −1 |
|  | 73 | 28 | −1 |
|  | 71 | 17 | −3 |
|  | 69 | 12 | −5 |
|  | 67 | 3 | −7 |
|  | 64 | −7 | −10 |
|  | 45 | −21 | −29 |
|  | 39 | −28 | −35 |
|  | 36 | −37 | −38 |
| 19 | 72 | 67 | 0 |
|  | 73 | 54 | 1 |
|  | 74 | 45 | 2 |
|  | 74 | 37 | 2 |
|  | 73 | 29 | 1 |
|  | 71 | 16 | −1 |
|  | 69 | 7 | −3 |
|  | 67 | −3 | −5 |
|  | 66 | −15 | −6 |
|  | 60 | −21 | −12 |
|  | 52 | −33 | −20 |
|  | 49 | −43 | −23 |
|  | 48 | −44 | −24 |
| 20 | 70 | 78 | 0 |
|  | 70 | 70 | 0 |
|  | 70 | 54 | 0 |
|  | 69 | 45 | −1 |
|  | 68 | 28 | −2 |
|  | 66 | 24 | −4 |
|  | 62 | 16 | −8 |
|  | 60 | 3 | −10 |
|  | 59 | −8 | −11 |
|  | 53 | 2 | −17 |
|  | 32 | −16 | −38 |
|  | 25 | −35 | −45 |

What is claimed is:

1. A computer-implemented method for automatically monitoring oxygenation levels of a compartment of injured tissue of a human body for automatically detecting conditions of a compartment syndrome, comprising:
   automatically monitoring oxygenation levels of the compartment of injured tissue in a continuous manner with a first non-invasive sensor;
   automatically monitoring oxygenation levels of healthy tissue in a continuous manner with a second non-invasive sensor, the second non-invasive sensor detecting systemic perfusion of the human body from the healthy tissue;
   automatically monitoring blood pressure of the human body in a continuous manner with a non-invasive blood pressure device, the blood pressure comprising diastolic and systolic blood pressure values; and
   automatically activating an alarm with a computing device when both the blood pressure of the human body comprising the diastolic and systolic blood pressure values decreases and oxygenation levels of the first non-invasive sensor for the compartment start decreasing in value compared to the oxygenation levels of the second non-invasive sensor for the healthy tissue, the second non-invasive sensor providing a basis for comparison for relative oxygenation levels of injured tissue.

2. The method of claim 1, further comprising displaying oxygenation levels of the compartment on a display device.

3. The method of claim 1, further comprising providing an alignment mechanism on the first non-invasive sensor.

4. The method of claim 1, further comprising calculating, with the computing device, a running average for the blood pressure and oxygenation levels.

5. The method of claim 1, wherein activating an alarm with the computing device further comprises activating an alarm that produces one or more alerts on a display device.

6. The method of claim 1, further comprising calculating, with the computing device, a mean arterial pressure (MAP) and displaying the mean arterial pressure (MAP) on a display device.

7. A system for automatically monitoring oxygenation levels of a compartment of a human body for automatically detecting conditions of a compartment syndrome, the system comprising:
   a plurality of non-invasive sensors for automatically detecting oxygenation levels of the human body in a continuous manner;
   a non-invasive blood pressure device for automatically sensing blood pressure of the human body in a continuous manner, the blood pressure comprising diastolic and systolic blood pressure values; and a computing device coupled to the non-invasive sensors and non-invasive blood pressure device, wherein the computing device is configured for:
monitoring oxygenation levels of injured tissue of a compartment from a first non-invasive sensor of the plurality of non-invasive sensors;
monitoring oxygenation levels of healthy tissue from a second non-invasive sensor of the plurality of non-invasive sensors;
monitoring the blood pressure of the human body; and
automatically activating an alarm when both the blood pressure comprising the diastolic and systolic blood pressure values of the human body decreases and oxygenation levels of the first non-invasive sensor start decreasing in value compared to the oxygenation levels of the second non-invasive sensor, the second non-invasive sensor providing a basis for comparison for relative oxygenation levels of injured tissue.

8. The system of claim 7, wherein the computing device is further configured for increasing a frequency at which the oxygenation levels and blood pressure are monitored when the oxygenation levels and blood pressure fall within a predetermined range of values.

9. The system of claim 7, further comprising a display device configured for simultaneously displaying the oxygenation levels and diastolic and systolic blood pressure values of the human body.

10. The system of claim 9, wherein one or more of the first non-invasive sensor and the second non-invasive sensor each comprises an array of non-invasive sensing elements.

11. The system of claim 10, wherein the computing device is further configured for controlling a timing for activating respective non-invasive sensors of the array in order to provide scans of different portions of the human body.

12. The system of claim 11, wherein the computing device is further configured for calculating a running average for the blood pressure and oxygenation levels.

13. The system of claim 12, wherein the alarm comprises at least one of an audible alarm and visual alarm.

14. The system of claim 13, wherein the computing device is further configured for calculating a mean arterial pressure (MAP) that is displayed on the display device.

15. A system for automatically monitoring oxygenation levels of a compartment of a human body for automatically detecting conditions of a compartment syndrome, the system comprising:

a plurality of non-invasive sensors for automatically detecting oxygenation levels of the human body in a continuous manner;

a non-invasive blood pressure device for automatically sensing blood pressure of the human body in a continuous manner, the blood pressure comprising diastolic and systolic blood pressure values; and a computing device coupled to the non-invasive sensors and non-invasive blood pressure device, wherein the computing device is configured for:
monitoring oxygenation levels of an injured portion of the human body from a first non-invasive sensor of the plurality of non-invasive sensors;
monitoring oxygenation levels of an uninjured portion of the human body from a second non-invasive sensor of the plurality of non-invasive sensors;
monitoring the blood pressure of the human body;
comparing oxygenation levels between the injured portion of the human body and the uninjured portion of the human body; and
automatically activating at least one of an audible alarm and visual alarm when both the blood pressure comprising the diastolic and systolic blood pressure values of the human body decreases and when the oxygenation levels of the first non-invasive sensor start decreasing compared to the oxygenation levels of the second non-invasive sensor, the second non-invasive sensor providing a basis for comparison for relative oxygenation levels of injured tissue.

16. The system of claim 15, further comprising a display device configured for simultaneously displaying the oxygenation levels and diastolic and systolic blood pressure values of the human body.

17. The system of claim 15, wherein the computing device is further configured for activating an alarm when the blood pressure and oxygenation levels approach predefined levels.

18. The system of claim 17, wherein the computing device is further configured for controlling a timing for activating respective non-invasive sensors in order to provide scans of different portions of the human body.

19. The system of claim 18, wherein the computing device is further configured for calculating a running average for the blood pressure and oxygenation levels.

* * * * *